(12) United States Patent
Funaya

(10) Patent No.: US 9,796,799 B2
(45) Date of Patent: Oct. 24, 2017

(54) TRANSITION METAL COMPOUND, OLEFIN POLYMERIZATION CATALYST, AND OLEFIN POLYMER PRODUCTION PROCESS

(71) Applicant: MITSUI CHEMICALS, INC., Tokyo (JP)

(72) Inventor: Munehito Funaya, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 15/195,340

(22) Filed: Jun. 28, 2016

(65) Prior Publication Data

US 2016/0304640 A1 Oct. 20, 2016

Related U.S. Application Data

(62) Division of application No. 14/429,842, filed as application No. PCT/JP2013/075713 on Sep. 24, 2013, now Pat. No. 9,458,261.

(30) Foreign Application Priority Data

Sep. 25, 2012 (JP) ................. 2012-211233

(51) Int. Cl.
| | |
|---|---|
| *C08F 110/06* | (2006.01) |
| *C08F 10/06* | (2006.01) |
| *C08F 4/6592* | (2006.01) |
| *C07F 17/00* | (2006.01) |
| *C08F 210/06* | (2006.01) |
| *C08F 4/659* | (2006.01) |

(52) U.S. Cl.
CPC ............ *C08F 110/06* (2013.01); *C07F 17/00* (2013.01); *C08F 4/65927* (2013.01); *C08F 10/06* (2013.01); *C08F 210/06* (2013.01); *C08F 4/65912* (2013.01); *C08F 4/65916* (2013.01)

(58) Field of Classification Search
CPC .............................. C08F 10/06; C08F 110/06
See application file for complete search history.

(56) References Cited

U.S. PATENT DOCUMENTS

| | | |
|---|---|---|
| 4,960,878 A | 10/1990 | Crapo et al. |
| 4,990,640 A | 2/1991 | Tsutsui |
| 5,036,034 A | 7/1991 | Ewen |
| 5,041,584 A | 8/1991 | Crapo et al. |
| 5,155,080 A | 10/1992 | Elder et al. |
| 5,321,106 A | 6/1994 | LaPointe |
| 5,387,568 A | 2/1995 | Ewen |
| 5,416,228 A | 5/1995 | Elder |

(Continued)

FOREIGN PATENT DOCUMENTS

| | | |
|---|---|---|
| CA | 2350563 | 5/2001 |
| CN | 1327448 | 12/2001 |

(Continued)

OTHER PUBLICATIONS

Korean Office Action dated Jan. 31, 2017 issued in the corresponding Korean patent application No. 10-2015-7008904.
Angew. Chem. Int. Ed. Engl., vol. 24, No. 6, pp. 507-508 (1985).
J. Am. Chem. Soc., vol. 110, No. 18, pp. 6255-6256 (1988).
Organometallics, vol. 21, No. 5, pp. 934-945 (2002).
Kaminsky et al., Metalorganic Catalysts for Synthesis and Polymerization, Springer-Verlag: Berlin, 1999, pp. 170-179.
Polypropylene Handbook, Kogyo Chosakai Publishing Co., Ltd., 1998, pp. 135-143.
Polymer, 1993, vol. 34, No. 19, pp. 4083-4088.
J. Macromol. Sci. Part B Phys. vol. 41, Nos. 4-6, (2002), p. 1121-1171.
Chem. Rev. vol. 100, No. 4, (2000), pp. 1253-1345.
Polypropylene Handbook, Kogyo Chosakai Publishing Co., Ltd., 1998, pp. 70-75.

(Continued)

*Primary Examiner* — Caixia Lu
(74) *Attorney, Agent, or Firm* — Rankin, Hill & Clark LLP

(57) ABSTRACT

[Object] To provide transition metal compounds with excellent catalytic activity which can afford olefin polymers such as propylene polymers that have high stereoregularity and high molecular weight and may be easily crystallized into a β-phase.
[Solution] The transition metal compound is represented by General Formula [I] or is an enantiomer thereof:

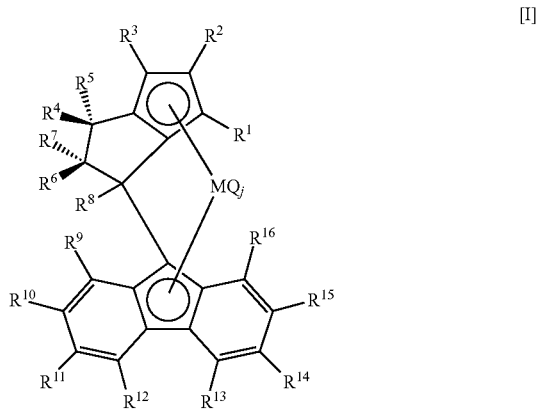

[in Formula [I], $R^1$, $R^3$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently a hydrogen atom, a hydrocarbon group, a hetero atom-containing hydrocarbon group, or a silicon-containing group; $R^2$ is a hydrocarbon group, a hetero atom-containing hydrocarbon group, or a silicon-containing group; $R^4$ is a hydrogen atom; any two substituents of the substituents $R^1$ to $R^{16}$ except $R^4$ may be bonded to each other to form a ring; M is a Group IV transition metal; Q is a structure such as a halogen atom; and j is an integer of 1 to 4].

2 Claims, 1 Drawing Sheet

(56) References Cited

U.S. PATENT DOCUMENTS

| | | | |
|---|---|---|---|
| 5,455,365 A | 10/1995 | Winter | |
| 5,519,100 A | 5/1996 | Ewen et al. | |
| 5,561,092 A | 10/1996 | Ewen | |
| 5,629,254 A | 5/1997 | Fukuoka et al. | |
| 5,731,254 A | 3/1998 | Spaleck | |
| 6,207,600 B1 * | 3/2001 | Nakajima | D04H 3/007 428/373 |
| 6,316,558 B1 | 11/2001 | Kaneko | |
| 6,559,089 B1 | 5/2003 | Bellia | |
| 6,984,743 B1 | 1/2006 | Schiemenz | |
| 2005/0228155 A1 | 10/2005 | Kawai | |
| 2008/0038498 A1 | 2/2008 | Itakura et al. | |
| 2008/0097055 A1 | 4/2008 | Funaya et al. | |
| 2009/0317615 A1 | 12/2009 | Itakura et al. | |
| 2010/0233398 A1 | 9/2010 | Nagao et al. | |
| 2011/0301309 A1 | 12/2011 | Tamura | |
| 2012/0049391 A1 | 3/2012 | Sakuma et al. | |
| 2015/0239996 A1 | 8/2015 | Funaya et al. | |

FOREIGN PATENT DOCUMENTS

| | | |
|---|---|---|
| CN | 101087821 | 12/2007 |
| CN | 101501128 | 8/2009 |
| EP | 0890664 | 1/1999 |
| EP | 1149120 | 10/2001 |
| EP | 1829903 | 9/2007 |
| JP | 01501950 | 7/1989 |
| JP | 01502036 | 7/1989 |
| JP | 02078687 | 3/1990 |
| JP | 02274703 | 11/1990 |
| JP | 03179005 | 8/1991 |
| JP | 03179006 | 8/1991 |
| JP | 03193796 | 8/1991 |
| JP | 03207703 | 9/1991 |
| JP | 03207704 | 9/1991 |
| JP | 04268304 | 9/1992 |
| JP | 06122718 | 5/1994 |
| JP | 06157661 | 6/1994 |
| JP | 07196734 | 8/1995 |
| JP | 10226694 | 8/1998 |
| JP | 2000219710 | 8/2000 |
| JP | 2001515911 | 9/2001 |
| JP | 2001526730 | 12/2001 |
| JP | 2003292518 | 10/2003 |
| JP | 2004051676 | 2/2004 |
| JP | 2008120931 | 5/2008 |
| JP | 2010111833 | 5/2010 |
| KR | 20070091148 A | 9/2007 |
| WO | 8805792 | 8/1988 |
| WO | 8805793 | 8/1988 |
| WO | 0027894 | 5/2000 |
| WO | 0127124 | 4/2001 |
| WO | 03/082879 | 10/2003 |
| WO | 2005066191 | 7/2005 |
| WO | 2006025540 | 3/2006 |
| WO | 2006068308 | 6/2006 |
| WO | 2007131010 | 11/2007 |
| WO | 2008032841 | 3/2008 |
| WO | 2009072505 | 6/2009 |
| WO | 2014050817 | 4/2014 |

OTHER PUBLICATIONS

J. Appl. Poly. Sci., vol. 109, No. 2, (2008), pp. 1338-1349.
Macromolecules., vol. 40, No. 19, (2007), pp. 6871-6878.
Chem. Eur. J., vol. 18, No. 14, (2012), pp. 4174-4178.
Macromolecules., vol. 29, No. 8, (1996), pp. 2729-2737.
J. Org. Chem., vol. 54, No. 21, 1989, pp. 4981-4982.
Angew. Chem. internal. Edit., vol. 9, No. 11, 1970, pp. 892-893.
J. Am. Chem. SOC., vol. 107, No. 18, 1985, 107, pp. 5308-5309.
J. Org. Chem., vol. 55, No. 15, 1990, pp. 4504-4506.
C. M. L. Atkinson, and R. Dietz., Die Makromol. Chem., 177, No. 1, (1976), pp. 212-231.
A. Zambelli, D. E. Dorman, A. I. Richard Brewster, and F. A. Bovey., Macromolecules, vol. 6, No. 6, pp. 925-926, (1973).
Turner Jones, A., Aizlewood, J. M., and Beckett, D. R., Die Makromol. Chem., 75, (1964), pp. 134-158.
International Search Report dated Nov. 5, 2013 filed in PCT/JP2013/075713.
Chinese Office Action dated Feb. 2, 2016 issued in Chinese patent application No. 201380049346.4.
Japanese Office Action dated Apr. 5, 2016 issued in Japanese patent application No. 2014-538493.
Extended European Search Report dated May 10, 2016 issued in European patent application No. 13842454.4.

* cited by examiner

[FIG. 1]
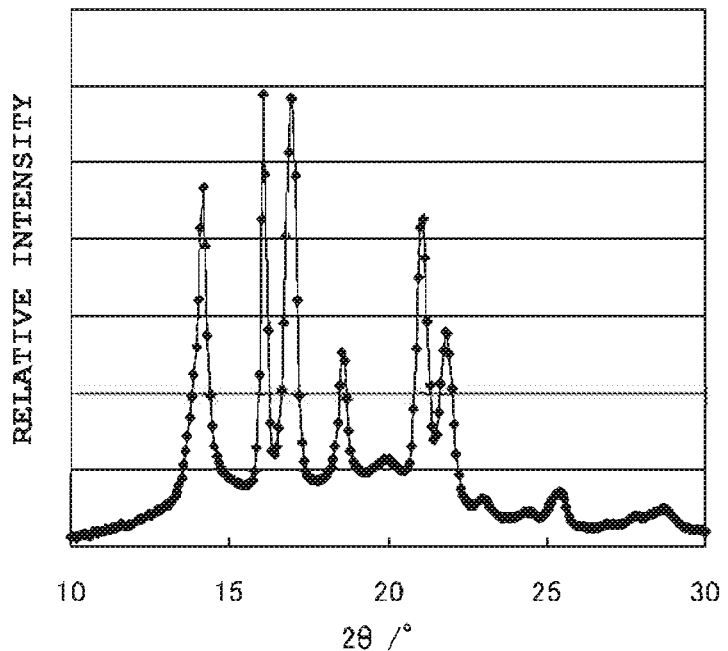
[FIG. 2]
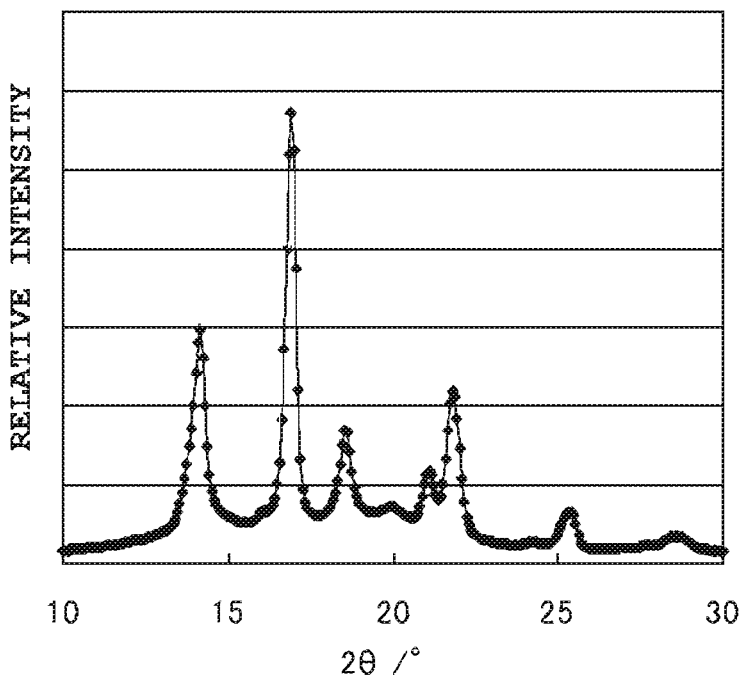

TRANSITION METAL COMPOUND, OLEFIN POLYMERIZATION CATALYST, AND OLEFIN POLYMER PRODUCTION PROCESS

TECHNICAL FIELD

The present invention relates to transition metal compounds having a useful and novel structure as an olefin polymerization catalyst component, olefin polymerization catalysts including the transition metal compound, and olefin polymer production processes involving the catalyst.

BACKGROUND ART

[Metallocene Compounds]

In recent years, metallocene compounds are well known as homogeneous catalysts for olefin polymerization. After the report of isotactic polymerization by W. Kaminsky et al. (see Non Patent Literature 1), many studies have been made on olefin polymerization, in particular, stereoregular α-olefin polymerization using metallocene compounds.

In α-olefin polymerization using metallocene compounds, it is known that the stereoregularity and the molecular weights of the obtainable α-olefin polymers are greatly varied by the introduction of substituents into the cyclopentadienyl ring ligands of the metallocene compounds or by the bridging of the two cyclopentadienyl rings.

[Bridged Metallocene Compounds]

For example, there are the following reports as to propylene polymerization catalyzed by metallocene compounds which have a ligand in which a cyclopentadienyl ring and a fluorenyl ring is bridged to each other.

From the viewpoint of stereoregularity, dimethylmethylene(cyclopentadienyl)(fluorenyl)zirconium dichloride affords syndiotactic polypropylene (see Non Patent Literature 2); dimethylmethylene(3-methylcyclopentadienyl)(fluorenyl)zirconium dichloride having a methyl group at the 3-position of the cyclopentadienyl ring affords hemiisotactic polypropylene (see Patent Literature 1); and dimethylmethylene(3-tert-butylcyclopentadienyl)(fluorenyl) zirconium dichloride having a tert-butyl group at the 3-position of the cyclopentadienyl ring affords isotactic polypropylene (see Patent Literature 2).

Dimethylmethylene(3-tert-butyl-5-ethylcyclopentadienyl) (3,6-di-tert-butylfluorenyl)zirconium dichloride having tert-butyl groups at the 3- and 6-positions of the fluorenyl ring affords polypropylene with higher isotactic stereoregularity than obtained with dimethylmethylene(3-tert-butyl-5-methylcyclopentadienyl)(fluorenyl)zirconium dichloride (see Patent Literature 3).

From the viewpoint of molecular weights, diphenylmethylene(cyclopentadienyl)(fluorenyl)zirconium dichloride having a cyclopentadienyl ring and a fluorenyl ring bridged via diphenylmethylene affords syndiotactic polypropylene having a higher molecular weight than obtained with dimethylmethylene(cyclopentadienyl)(fluorenyl)zirconium dichloride (see Patent Literature 4); diphenylmethylene(3-(2-adamantyl)-cyclopentadienyl)(fluorenyl)zirconium dichloride having a diphenylmethylene bridge affords isotactic-hemiisotactic polypropylene having a higher molecular weight than obtained with dimethylmethylene(3-(2-adamantyl)-cyclopentadienyl)(fluorenyl)zirconium dichloride (see Non Patent Literature 3); and dimethylmethylene(3-tert-butyl-5-methylcyclopentadienyl)(fluorenyl)zirconium dichloride having a methyl group at the 5-position of the cyclopentadienyl ring (the α-position relative to the bridge) affords isotactic polypropylene having a higher molecular weight than obtained with dimethylmethylene(3-tert-butyl-cyclopentadienyl)(fluorenyl) zirconium dichloride (see Patent Literature 5).

Further, dimethylmethylene(3-tert-butyl-2-methylcyclopentadienyl)(fluorenyl)zirconium dichloride and diphenylmethylene (3,4-dimethylcyclopentadienyl)(fluorenyl) zirconium dichloride having substituents at two adjacent positions on the cyclopentadienyl ring afford polypropylene having a lower molecular weight than obtained with dimethylmethylene(3-tert-butyl-5-methylcyclopentadienyl) (fluorenyl)zirconium dichloride and diphenylmethylene(3-methylcyclopentadienyl)(fluorenyl)zirconium dichloride, respectively (see Patent Literatures 5 and 6).

[5-Membered Ring-Bridged Metallocene Compounds]

A study reports the polymerization of propylene catalyzed by a metallocene compound in which a cyclopentadienyl ring and a fluorenyl ring are bridged via a 5-membered ring. However, such metallocene compounds have low usefulness in industry because of the fact that the stereoregularity of the obtainable polypropylenes is very low (see Non Patent Literature 4).

A recent study reports a metallocene compound having a cyclopentadienyl ring and a fluorenyl ring bridged via a 5-membered ring which can afford polypropylene having relatively high stereoregularity (see Patent Literature 7).

These metallocene compounds mentioned above exhibit excellent polymerization performance. In some applications, however, the catalysts are often required to afford polymers having still higher stereoregularity or still higher molecular weight with higher economic efficiency, namely, with high catalytic activity even under high-temperature polymerization conditions. Improvements are thus required.

[Metallocene Compounds Having Substituted Indenyl Ligands]

According to reports, metallocene compounds having substituted indenyl ligands afford relatively high stereoregularity or molecular weight (see Patent Literatures 8 and 9). However, such compounds are unsatisfactory in terms of performance under economically efficient polymerization conditions.

Because metallocene compounds are soluble in reaction media, they are generally used to catalyze polymerization in the form of supported catalyst systems in slurry polymerization or gas phase polymerization. Specifically, the metallocene compounds are supported on solid carriers. However, it is known that the polymerization performances such as stereoregularity control of the aforementioned compounds are markedly decreased when they are used in the supported form on carriers as compared to in the absence of carriers.

[Metallocene Compounds Having Substituted Azulenyl Groups]

To solve such problems, for example, a recent study reports a metallocene compound having a substituted azulenyl group as a ligand (see Patent Literature 10). However, even such catalysts do not achieve sufficient performances such as stereoregularity control when the polymerization temperature is elevated to obtain economic efficiency or when the compounds are supported on solid carriers.

Under these circumstances, there have been demands for further improvements in the catalytic performances such as polymerization activity, stereoregularity control and molecular weight control of polymerization catalysts including metallocene compounds (hereinafter, also written as "metallocene catalysts").

[Olefin Polymers]

Olefin polymers, in particular, crystalline isotactic polypropylenes are widely used in various forming fields because of their inexpensiveness and excellent mechanical properties and chemical resistance.

Isotactic polypropylenes are known to have various-phase structures such as α-structure, β-structure, γ-structure and mesophase structure (see Non Patent Literature 5). Of these, the α-phase is the most stable structure. On the other hand, the β-phase outperforms the α-phase in such properties as impact resistance (see Patent Literature 11). Methods have been disclosed in which the surface roughness of films is controlled or porous films are produced by utilizing the nature of the polypropylenes being transitioned from the β-phase to the α-phase upon treatment such as heating or stretching (Patent Literatures 12 and 13).

Because the β-phase is a metastable structure, this phase is scarcely formed in Ziegler-Natta-catalyzed polypropylene under usual crystallization conditions irrespective of the primary structure of the polymer (see Non Patent Literature 6), and is formed only under specific crystallization conditions. Specifically, the β-phase is obtained by a temperature gradient method or by adding a large amount of a β-phase nucleator (see Non Patent Literature 7). In, for example, Patent Literature 13, the occurrence of a β-phase is evaluated based on β-activity as the indicator using differential scanning calorimetry (DSC). However, the β-activity is exhibited as a result of the addition of a β-phase nucleator, and thus resins free from β-phase nucleators show no β-activity.

[Isotactic Polypropylenes]

As mentioned earlier, there have recently been active studies and developments of metallocene-catalyzed isotactic polypropylenes. Metallocene-catalyzed isotactic polypropylenes have a uniform primary structure and hence exhibit excellent properties. Thus, a success in allowing metallocene-catalyzed isotactic polypropylenes to be formed into a β-phase will highly increase the usefulness of the polymers.

Unlike Ziegler-Natta-catalyzed polypropylenes, metallocene-catalyzed isotactic polypropylenes contain regioerrors ascribed to 2,1-insertions and 1,3-insertions in the primary structure (see Non Patent Literatures 8 and 9). As a result, the metallocene-catalyzed polypropylenes are prone to take a γ-phase form as compared to the Ziegler-Natta-catalyzed polypropylenes (see Non Patent Literature 10), and there is a study reporting that a sufficient amount of β-phase is not formed even when a β-phase nucleator is added (see Non Patent Literature 11).

A further study reports a metallocene-catalyzed polypropylene which is obtained by polymerization at an extremely low temperature and which consequently has a meso pentad fraction of greater than 99.9% and a very small amount of regioerrors ascribed to 2,1-insertions and 1,3-insertions according to $^{13}$C-NMR (see Patent Literature 14). In Patent Literature 14, the melting point of the phases is measured by DSC, but there is no description as to whether any melting point assigned to a β-phase was observed.

A recent study reports a metallocene-catalyzed isotactic polypropylene having high stereoregularity and a relatively small amount of regioerrors ascribed to 2,1-insertions and 1,3-insertions (see Non Patent Literature 12). In Non Patent Literature 12, the melting point of the phases is measured by DSC, but there is no description as to whether any melting point assigned to a β-phase was observed.

CITATION LIST

Patent Literature

Patent Literature 1: JP-A-H03-193796
Patent Literature 2: JP-A-H06-122718
Patent Literature 3: WO 2001/027124
Patent Literature 4: JP-A-H02-274703
Patent Literature 5: JP-A-2001-526730
Patent Literature 6: JP-A-H10-226694
Patent Literature 7: WO 2006/068308
Patent Literature 8: JP-A-H04-268304
Patent Literature 9: JP-A-H06-157661
Patent Literature 10: JP-A-2003-292518
Patent Literature 11: WO 2008/032841
Patent Literature 12: JP-A-2008-120931
Patent Literature 13: JP-A-2010-111833
Patent Literature 14: JP-A-2000-219710

Non Patent Literature

Non Patent Literature 1: Angew. Chem. Int. Ed. Engl., 24, 507 (1985)
Non Patent Literature 2: J. Am. Chem. Soc., 110, 6255 (1988)
Non Patent Literature 3: Organometallics, 21, 934 (2002)
Non Patent Literature 4: Metalorganic Catalysts for Synthesis and Polymerization, Springer-Verlag: Berlin, 1999; p. 170.
Non Patent Literature 5: Polypropylene Handbook, Kogyo Chosakai Publishing Co., Ltd., 1998, p. 135
Non Patent Literature 6: Polymer, 4083 (1993)
Non Patent Literature 7: J. Macromol. Sci. Part B Phys. (2002), 1121
Non Patent Literature 8: Chem. Rev. (2000), 100, 1253
Non Patent Literature 9: Polypropylene Handbook, Kogyo Chosakai Publishing Co., Ltd., 1998, p. 72
Non Patent Literature 10: J. Appl. Poly. Sci., Vol. 109, 1338 (2008)
Non Patent Literature 11: Macromolecules (2007), 40, 6871
Non Patent Literature 12: Chem. Eur. J. (2012), 18, 4174-4178

SUMMARY OF INVENTION

Technical Problem

An object of the invention is to provide transition metal compounds with excellent catalytic activity which can afford olefin polymers such as propylene polymers that have high stereoregularity and high molecular weight and may be easily formed into a β-phase. Another object of the invention is to provide olefin polymerization catalysts including the transition metal compound which can afford olefin polymers under economically efficient polymerization conditions. A further object is to provide olefin polymer production processes using the polymerization catalyst.

A still further object of the invention is to provide novel propylene polymers that have high stereoregularity and high molecular weight and may be easily formed into a β-phase while having these properties.

Solution to Problem

The present inventors carried out extensive studies to achieve the above objects. As a result, the present inventors have found that the objects are achieved by the use of transition metal compounds having the following configurations, thereby accomplishing the present invention.

An aspect of the invention resides in a transition metal compound represented by General Formula [I] or an enantiomer thereof:

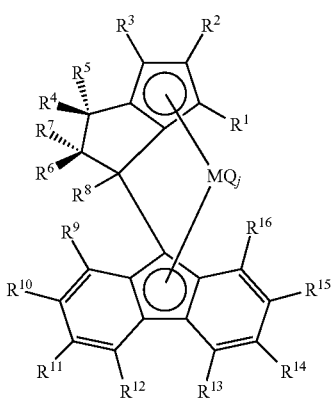

[in Formula [I], $R^1$, $R^3$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently a hydrogen atom, a hydrocarbon group, a hetero atom-containing hydrocarbon group, or a silicon-containing group; $R^2$ is a hydrocarbon group, a hetero atom-containing hydrocarbon group, or a silicon-containing group; $R^4$ is a hydrogen atom; any two substituents of the substituents $R^1$ to $R^{16}$ except $R^1$ may be bonded to each other to form a ring; M is a transition metal of Group IV; Q is a halogen atom, a hydrocarbon group, an anionic ligand, or a neutral ligand coordinatable with a lone electron pair; j is an integer of 1 to 4; and when j is an integer of 2 or greater, Qs may be the same or different from one another].

In General Formula [I], $R^1$ and $R^3$ are preferably hydrogen atoms; $R^2$ is preferably a hydrocarbon group having 1 to 20 carbon atoms; $R^2$ is more preferably a substituent in which a carbon bonded to the cyclopentadienyl ring is a tertiary carbon; $R^5$ and $R^7$ are preferably bonded to each other to form a ring; $R^9$, $R^{12}$, $R^{13}$ and $R^{16}$ are preferably hydrogen atoms; and $R^{10}$, $R^{11}$, $R^{14}$ and $R^{15}$ are preferably hydrocarbon groups, or $R^{10}$ and $R^{11}$ are preferably bonded to each other to form a ring and $R^{14}$ and $R^{15}$ are preferably bonded to each other to form a ring.

Another aspect of the invention resides in an olefin polymerization catalyst including at least one transition metal compound selected from the above transition metal compounds and enantiomers thereof.

Preferably, the olefin polymerization catalyst includes at least one transition metal compound (A) selected from the aforementioned transition metal compounds and enantiomers thereof, and at least one compound (B) selected from organometallic compounds (B-1), organoaluminum-oxy compounds (B-2), and compounds (B-3) capable of reacting with the transition metal compound (A) to form an ion pair.

Preferably, the olefin polymerization catalyst further includes a carrier (C), and the transition metal compound (A) is supported on the carrier (C).

Another aspect of the invention resides in a process for producing the aforementioned transition metal compound or an enantiomer thereof including a step of preparing a pentalene compound represented by General Formula (1a):

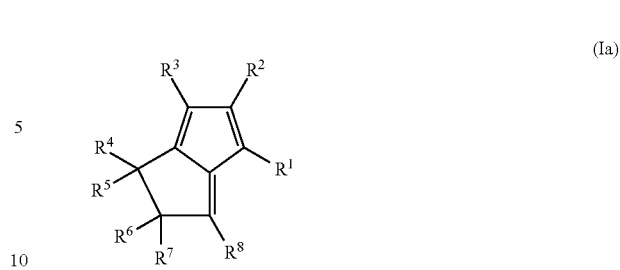

[in Formula (1a), $R^1$, $R^3$, $R^5$, $R^6$, $R^7$ and $R^8$ are each independently a hydrogen atom, a hydrocarbon group, a hetero atom-containing hydrocarbon group, or a silicon-containing group; $R^2$ is a hydrocarbon group, a hetero atom-containing hydrocarbon group, or a silicon-containing group; $R^4$ is a hydrogen atom; and any two substituents of the substituents $R^1$ to $R^8$ except $R^4$ may be bonded to each other to form a ring].

Another aspect of the invention resides in a process for producing an olefin polymer including a step of polymerizing propylene and optionally at least one olefin selected from ethylene and α-olefins having 4 to 30 carbon atoms in the presence of the aforementioned olefin polymerization catalyst, the olefin polymer including propylene-derived structural units in the range of 50 to 100 mol % (wherein the total of the content of structural units derived from propylene and the content of structural units derived from the olefin(s) is 100 mol %).

Another aspect of the invention resides in an olefin polymer obtained by the above production process.

Another aspect of the invention resides in a propylene polymer having a meso pentad fraction of 97.0% to 99.5% and a total fraction of 2,1-insertions and 1,3-insertions of propylene monomers of 0.01 mol % to 0.06 mol % relative to all the propylene-derived structural units as measured by $^{13}$C-NMR.

Another aspect of the invention resides in a shaped article including the propylene polymer.

Advantageous Effects of Invention

The transition metal compounds of the invention have excellent catalytic activity and can afford olefin polymers such as propylene polymers that have high stereoregularity and high molecular weight and may be easily formed into a β-phase. The olefin polymerization catalysts of the invention include the transition metal compound and can afford olefin polymers under economically efficient polymerization conditions. The olefin polymer production processes of the invention involve the polymerization catalyst.

The novel propylene polymers of the invention have high stereoregularity and high molecular weight and may be easily formed into a β-phase while having these properties.

BRIEF DESCRIPTION OF DRAWINGS

FIG. 1 illustrates an X-ray diffraction pattern of a propylene homopolymer in Example 7c.

FIG. 2 illustrates an X-ray diffraction pattern of a propylene homopolymer in Comparative Example 9c.

DESCRIPTION OF EMBODIMENTS

Hereinbelow, there will be sequentially described transition metal compounds represented by General Formula [I] and enantiomers thereof, processes for producing such compounds, olefin polymerization catalysts including at least one of such compounds, olefin polymer production processes using the olefin polymerization catalyst, olefin polymers, and shaped articles including the olefin polymer.

In the specification, compounds represented by Formula (X) (X: formula number) are also written as "compounds (X)". In the description of polymers, structural units derived from compound A are also written as "compound A units", and the content thereof may be written as "compound A content".

[Transition Metal Compounds]

The transition metal compounds of the invention are transition metal compounds represented by General Formula [I] or enantiomers thereof. Although the specification does not specifically mention the enantiomers, the transition metal compounds of the invention include all the enantiomers of the transition metal compounds [I], for example, transition metal compounds represented by General Formula [I'], without departing from the spirit of the invention.

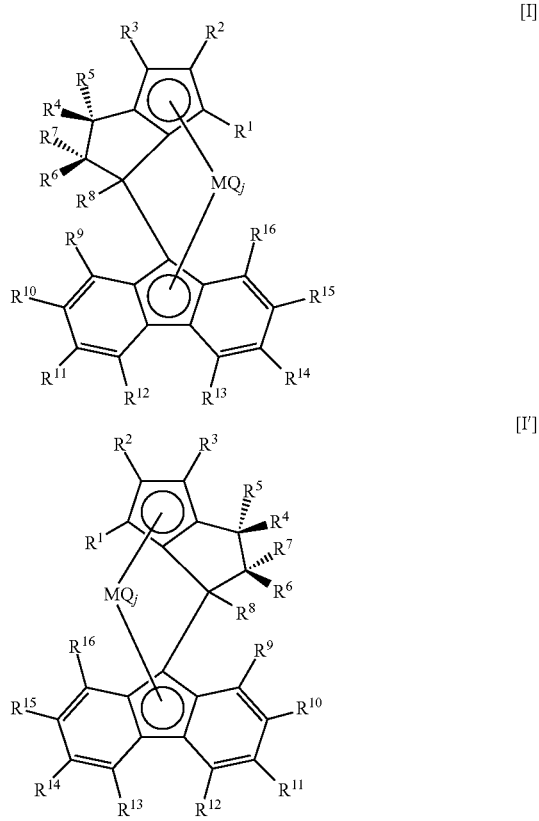

In Formula [I], $R^1$, $R^3$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently a hydrogen atom, a hydrocarbon group, a hetero atom-containing hydrocarbon group, or a silicon-containing group; $R^2$ is a hydrocarbon group, a hetero atom-containing hydrocarbon group, or a silicon-containing group; $R^4$ is a hydrogen atom; and any two substituents of the substituents $R^1$ to $R^{16}$ except $R^4$ may be bonded to each other to form a ring.

In Formula [I], M is a transition metal of Group IV; Q is a halogen atom, a hydrocarbon group, an anionic ligand, or a neutral ligand coordinatable with a lone electron pair; j is an integer of 1 to 4; and when j is an integer of 2 or greater, Qs may be the same or different from one another.

In Formulae [I] and [I'], the $MQ_j$ moiety comes out of the plane of the paper, and the bridge goes back behind the plane of the paper. Specifically, the transition metal compounds of the invention are such that the hydrogen atom ($R^4$) is bonded to the α-position relative to the cyclopentadiene ring (relative to the carbon atom substituted with the bridge) on the same side as the central metal.

The transition metal compounds [I] of the invention are such that $R^2$ is not a hydrogen atom and $R^4$ is a hydrogen atom. This configuration removes the difficulties encountered with the conventional metallocene compounds in producing olefin polymers which have high stereoregularity and an appropriate amount of regioerrors and further have a high molecular weight under economically efficient polymerization conditions.

The reasons why the transition metal compounds [I] of the invention exhibit excellent performance will be explained based on an estimated polymerization mechanism below. As an example, the influence on the molecular weights of polymers will be discussed.

Polymerization reaction produces a polymer having a high molecular weight when the insertion of a monomer between a central metal of a catalyst and a polymer chain, namely, the growth reaction takes place at a much higher rate than chain transfer reaction which stops the growth of the polymer chain. Two main chain transfer reactions that are known in metallocene-catalyzed olefin polymerization reaction are β-hydrogen transfer in which a hydrogen atom transfers to a central metal M of a catalyst, and β-hydrogen transfer in which a hydrogen atom transfers to a monomer, and the latter β-hydrogen transfer is said to be the main dominant transfer (see, for example, Chem. Rev. (2000), 100, 1253).

Transition states of these transfers are schematically illustrated in Formulae (i) to (iii). Ligands of the catalyst are omitted. In Formulae (i) to (iii), M' represents the active central metal of the catalyst, and P indicates the polymer chain.

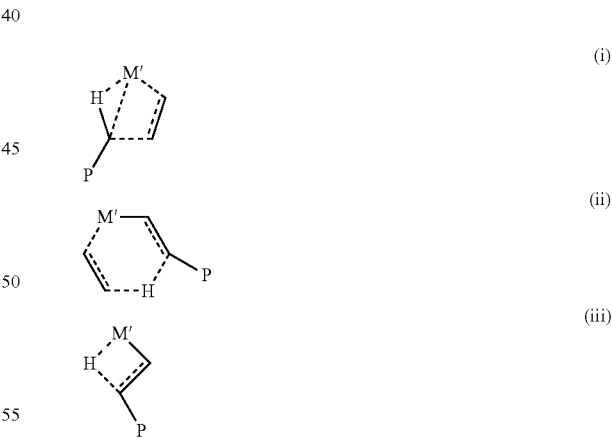

The structure in the transition state in the β-hydrogen transfer to the monomer is an M'-centered, six-membered ring structure (Formula (ii)). In the monomer insertion reaction, a five-membered ring structure is formed as a result of the coordination of the α-hydrogen to M' (Formula (i)). The narrowing of the space near M' by the ligands of the catalyst renders the six-membered ring structure in the transition state requiring a larger space less stable than the five-membered ring structure in the transition state. That is, the reaction rate of the β-hydrogen transfer to the monomer is decreased, and the reaction rate of the insertion of the monomer is relatively increased. As a result, the molecular weight of the resultant polymer is increased (see Macromolecules (1996), 29, 2729).

On the other hand, the structure in the transition state in the β-hydrogen transfer to the central metal M is a four-membered ring structure (Formula (iii)) occupying a smaller space than the structure in the transition state in the monomer insertion reaction. As a result, excessive narrowing of the space near M' by the ligands will cause a relative increase in the reaction rate of the β-hydrogen transfer to the central metal M, and consequently the molecular weight of the resultant polymer is expected to be low.

The above reaction mechanism is applied to the transition metal compound [I] of the invention. The transition metal compound [I] has a five-membered ring structure as the bridge between the cyclopentadiene ring and the fluorene ring. If the skeleton is such that $R^2$ is not a hydrogen atom and $R^4$ is a substituent larger than a hydrogen atom, namely, a substituent other than a hydrogen atom, the space near the central metal M is narrowed. Although such a structure may suppress the β-hydrogen transfer to the monomer which proceeds via the transition state with the six-membered ring structure, it is probable that the reaction rate of the monomer insertion reaction via the transition state with the five-membered ring structure will be decreased at the same time. As a result, the β-hydrogen transfer to the central metal M via the transition state with the four-membered ring structure is promoted, and the polymer is not grown to a sufficiently high molecular weight.

In contrast, a skeleton in which $R^2$ is not a hydrogen atom and $R^4$ is a hydrogen atom is considered to be able to suppress the β-hydrogen transfer to the monomer alone without inhibiting the monomer insertion reaction, and consequently the polymer may be grown to a higher molecular weight.

The mechanism described above is probably the reason why the catalyst exhibits excellent performance only when the bridge between the cyclopentadiene ring and the fluorene ring includes a five-membered ring stricture and $R^2$ is not a hydrogen atom while $R^4$ is a hydrogen atom.

Next, the influence on the regioregularity of polymers will be discussed. It is known that substituents on ligands of bridged metallocene compounds have influence on the regioregularity of polymers and, in particular, a substituent at an α-position relative to a cyclopentadiene (or a derivative thereof) moiety (relative to the carbon atom substituted with the bridge) has a larger influence (Chem. Rev. (2000), 100, 1253). The main factor of this influence is probably the steric hindrance of the substituent at the α-position. Based on this, $R^4$ in the transition metal compound [I] of the invention is limited to a hydrogen atom, and consequently the steric hindrance is reduced, namely, the regioregularity control is decreased as compared to when the substituent is other group such as an alkyl group. It is probably due to this effect that the obtainable polymer contains a very small amount of 2,1-insertions and 1,3-insertions which facilitate the polymer to be crystallized into a β-phase.

⟨ $R^1$ to $R^{16}$ ⟩

Examples of the hydrocarbon groups represented by any of $R^1$ to $R^6$ (except $R^4$) include linear hydrocarbon groups, branched hydrocarbon groups, cyclic saturated hydrocarbon groups, cyclic unsaturated hydrocarbon groups, and groups resulting from the substitution of one, or two or more hydrogen atoms in saturated hydrocarbon groups with cyclic unsaturated hydrocarbon groups. The number of carbon atoms in the hydrocarbon groups is usually 1 to 20, preferably 1 to 15, and more preferably 1 to 10.

Examples of the linear hydrocarbon groups include linear alkyl groups such as methyl group, ethyl group, n-propyl group, n-butyl group, n-pentyl group, n-hexyl group, n-heptyl group, n-octyl group, n-nonyl group and n-decanyl group; and linear alkenyl groups such as allyl group.

Examples of the branched hydrocarbon groups include branched alkyl groups such as isopropyl group, tert-butyl group, tert-amyl group, 3-methylpentyl group, 1,1-diethylpropyl group, 1,1-dimethylbutyl group, 1-methyl-1-propylbutyl group, 1,1-propylbutyl group, 1,1-dimethyl-2-methylpropyl group and 1-methyl-1-isopropyl-2-methylpropyl group.

Examples of the cyclic saturated hydrocarbon groups include cycloalkyl groups such as cyclopentyl group, cyclohexyl group, cycloheptyl group, cyclooctyl group and methylcyclohexyl group; and polycyclic groups such as norbornyl group, adamantyl group and methyladamantyl group.

Examples of the cyclic unsaturated hydrocarbon groups include aryl groups such as phenyl group, tolyl group, naphthyl group, biphenyl group, phenanthryl group and anthracenyl group; cycloalkenyl groups such as cyclohexenyl group; and polycyclic unsaturated alicyclic groups such as 5-bicyclo[2.2.1]hept-2-enyl group.

Examples of the groups resulting from the substitution of one, or two or more hydrogen atoms in saturated hydrocarbon groups with cyclic unsaturated hydrocarbon groups include groups resulting from the substitution of one, or two or more hydrogen atoms in alkyl groups with aryl groups, such as benzyl group, cumyl group, 1,1-diphenylethyl group and triphenylmethyl group.

Examples of the hetero atom-containing hydrocarbon groups represented by any of $R^1$ to $R^{16}$ (except $R^4$) include oxygen atom-containing hydrocarbon groups, for example, alkoxy groups such as methoxy group and ethoxy group, aryloxy groups such as phenoxy group, and furyl group; nitrogen atom-containing hydrocarbon groups, for example, amino groups such as N-methylamino group, N,N-dimethylamino group and N-phenylamino group, and pyrryl group; and sulfur atom-containing hydrocarbon groups, for example, thienyl group. The number of carbon atoms in the hetero atom-containing hydrocarbon groups is usually 1 to 20, preferably 2 to 18, and more preferably 2 to 15. Silicon-containing groups are excluded from the hetero atom-containing hydrocarbon groups.

Examples of the silicon-containing groups represented by any of $R^1$ to $R^{16}$ (except $R^4$) include groups represented by —$SiR_3$ (wherein Rs are each independently an alkyl group having 1 to carbon atoms or a phenyl group), such as trimethylsilyl group, triethylsilyl group, dimethylphenylsilyl group, diphenylmethylsilyl group and triphenylsilyl group.

Of the substituents $R^1$ to $R^{16}$ except $R^4$, any two adjacent substituents (for example: $R^1$ and $R^2$, $R^2$ and $R^3$, $R^5$ and $R^7$, $R^6$ and $R^8$, $R^7$ and $R^8$, $R^9$ and $R^{10}$, $R^{10}$ and $R^{11}$, $R^{11}$ and $R^{12}$, $R^{13}$ and $R^{14}$, $R^{14}$ and $R^{15}$, and $R^{15}$ and $R^{16}$) may be bonded to each other to form a ring. $R^6$ and $R^7$ may be bonded to each other to form a ring, $R^1$ and $R^8$ may be bonded to each other to form a ring, and $R^3$ and $R^5$ may be bonded to each other to form a ring. Two or more such rings may be present in the molecule.

In the specification, examples of the rings formed by the bonding of two substituents (the additional rings) include alicyclic rings, aromatic rings and hetero rings. Specific examples include a cyclohexane ring; a benzene ring; a hydrogenated benzene ring; a cyclopentene ring; and hetero rings such as a furan ring and a thiophene ring, and corresponding hydrogenated hetero rings. A cyclohexane ring; and a benzene ring and a hydrogenated benzene ring are preferable. Such a ring structure may further have a substituent such as an alkyl group on the ring.

From the viewpoint of stereoregularity control, $R^1$ and $R^3$ are preferably hydrogen atoms.

At least one selected from $R^5$, $R^6$ and $R^7$ is preferably a hydrocarbon group, a hetero atom-containing hydrocarbon group or a silicon-containing group. It is more preferable that $R^5$ be a hydrocarbon group. $R^5$ is more preferably an alkyl group having 2 or more carbon atoms such as a linear alkyl group or a branched alkyl group, or a cycloalkyl group or a cycloalkenyl group. Particularly preferably, $R^5$ is an alkyl group having 2 or more carbon atoms. From the viewpoint of synthesis, it is also preferable that $R^6$ and $R^7$ be hydrogen atoms. More preferably, $R^5$ and $R^7$ are bonded to each other to form a ring, and the ring is particularly preferably a six-membered ring such as a cyclohexane ring.

$R^8$ is preferably a hydrocarbon group, and is particularly preferably an alkyl group.

From the viewpoint of stereoregularity control, $R^2$ is preferably a hydrocarbon group, more preferably a hydrocarbon group having 1 to 20 carbon atoms, still more preferably a hydrocarbon group other than aryl groups, further preferably a linear hydrocarbon group, a branched hydrocarbon group or a cyclic saturated hydrocarbon group, and particularly preferably a substituent in which the free valence carbon (the carbon bonded to the cyclopentadienyl ring) is tertiary carbon.

Specific examples of $R^2$ include methyl group, ethyl group, isopropyl group, tert-butyl group, tert-pentyl group, tert-amyl group, 1-methylcyclohexyl group and 1-adamantyl group. More preferred substituents are those in which the free valence carbon is tertiary carbon, such as tert-butyl group, tert-pentyl group, 1-methylcyclohexyl group and 1-adamantyl group. Particularly preferred substituents are 1-adamantyl group and tert-butyl group.

In General Formula [I], the fluorene ring moiety is not particularly limited as long as the structure is formed of a known fluorene derivative. From the viewpoint of the controlling of stereoregularity and molecular weight, however, it is preferable that $R^9$, $R^{12}$, $R^{13}$ and $R^{16}$ be hydrogen atoms.

$R^{10}$, $R^{11}$, $R^{14}$ and $R^{15}$ are preferably hydrogen atoms, hydrocarbon groups, oxygen atom-containing hydrocarbon groups or nitrogen atom-containing hydrocarbon groups, more preferably hydrocarbon groups, and still more preferably hydrocarbon groups having 1 to 20 carbon atoms.

$R^{10}$ and $R^{11}$ may be bonded to each other to form a ring, and $R^{14}$ and $R^{15}$ may be bonded to each other to form a ring. Examples of such substituted fluorenyl groups include benzofluorenyl group, dibenzofluorenyl group, octahydrodibenzofluorenyl group, 1,1,4,4,7,7,10,10-octamethyl-2,3,4,7,8,9,10,12-octahydro-1H-dibenzo[b,h]fluorenyl group, 1,1,3,3,6,6,8,8-octamethyl-2,3,6,7,8,10-hexahydro-1H-dicyclopenta[b,h]fluorenyl group and 1',1',3',6',8',8'-hexamethyl-1'H,8'H-dicyclopenta[b,h]fluorenyl group, with 1,1,4,4,7,7,10,10-octamethyl-2,3,4,7,8,9,10,12-octahydro-1H-dibenzo[b,h]fluorenyl group being particularly preferable.

⟨M, Q and j⟩

M is a Group IV transition metal, preferably Ti, Zr or Hf, more preferably Zr or Hf, and particularly preferably Zr.

Examples of the halogen atoms which may be represented by Q include fluorine, chlorine, bromine and iodine.

Examples of the hydrocarbon groups which may be represented by Q include groups similar to the hydrocarbon groups represented by any of $R^1$ to $R^{16}$ (except $R^4$), with alkyl groups such as linear alkyl groups and branched alkyl groups being preferable.

Examples of the anionic ligands which may be represented by Q include alkoxy groups such as methoxy and tert-butoxy; aryloxy groups such as phenoxy; carboxylate groups such as acetate and benzoate; sulfonate groups such as mesylate and tosylate; and amide groups such as dimethylamide, diisopropylamide, methylanilide and diphenylamide.

Examples of the neutral ligands coordinatable with a lone electron pair which may be represented by Q include organophosphorus compounds such as trimethylphosphine, triethylphosphine, triphenylphosphine and diphenylmethylphosphine; and ethers such as tetrahydrofuran, diethyl ether, dioxane and 1,2-dimethoxyethane.

It is preferable that at least one Q be a halogen atom or an alkyl group.

The letter j is preferably 2.

Some preferred embodiments of the configurations of the inventive transition metal compounds [I], namely, $R^1$ to $R^{16}$, M, Q and j are described hereinabove. In the invention, any combinations of these preferred embodiments are also preferable.

⟨Examples of Preferred Transition Metal Compounds⟩

In the following examples, 1,1,4,4,7,7,10,10-octamethyl-2,3,4,7,8,9,10,12-octahydro-1H-dibenzo[b,h]fluorene is written as octamethylfluorene, and 1',1',3',6',8',8'-hexamethyl-1'H,8'H-dicyclopenta[b,h]fluorene as hexamethyldicyclopentafluorene.

Preferred examples of the transition metal compound of the present invention include:

[1-(fluorene-9'-yl)(1,2,3,4-tetrahydropentalene)]zirconium dichloride,

[1-(2',7'-di-tert-butylfluorene-9'-yl)(1,2,3,4-tetrahydropentalene)]zirconiumdichloride,

[1-(3',6'-di-tert-butylfluorene-9'-yl)(1,2,3,4-tetrahydropentalene)]zirconiumdichloride,

[1-(3',6'-di-(1-adamantyl)-fluorene-9'-yl)(1,2,3,4-tetrahydropentalene)]zirconiumdichloride,

[1-(3',6'-di-tert-butyl-2',7'-dimethylfluorene-9'-yl)(1,2,3,4-tetrahydropentalene)]zirconiumdichloride,

[1-(octamethylfluorene-12'-yl)(1,2,3,4-tetrahydropentalene)]zirconiumdichloride,

[1-(hexamethyldicyclopentafluorene-10'-yl)(1,2,3,4-tetrahydropentalene)]zirconiumdichloride,

[1-(fluorene-9'-yl)(5-tert-butyl-1-methyl-1,2,3,4-tetrahydropentalene)]zirconiumdichloride,

[1-(2',7'-di-tert-butylfluorene-9'-yl)(5-tert-butyl-1-methyl-1,2,3,4-tetrahydropentalene)]zirconiumdichloride,

[1-(3',6'-di-tert-butylfluorene-9'-yl)(5-tert-butyl-1-methyl-1,2,3,4-tetrahydropentalene)]zirconiumdichloride,

[1-(3',6'-di-(1-adamantyl)-fluorene-9'-yl)(5-tert-butyl-1-methyl-1,2,3,4-tetrahydropentalene)]zirconiumdichloride,

[1-(3',6'-di-tert-butyl-2',7'-dimethylfluorene-9'-yl)(5-tert-butyl-1-methyl-1,2, 3,4-tetrahydropentalene)]zirconiumdichloride,

[1-(octamethylfluorene-12'-yl)(5-tert-butyl-1-methyl-1,2,3,4-tetrahydropentalene)]zirconiumdichloride,

[1-(hexamethyldicyclopentafluorene-10'-yl)(5-tert-butyl-1-methyl-1,2,3,4-tetrahydropentalene)]zirconiumdichloride,

[1-(fluorene-9'-yl)(5-tert-butyl-1-phenyl-1,2,3,4-tetrahydropentalene)]zirconiumdichloride,

[1-(2',7'-di-tert-butylfluorene-9'-yl)(5-tert-butyl-1-phenyl-1,2,3,4-tetrahydropentalene)]zirconiumdichloride,

[1-(3',6'-di-tert-butylfluorene-9'-yl)(5-tert-butyl-1-phenyl-1,2,3,4-tetrahydropentalene)]zirconiumdichloride,
[1-(3',6-di-(1-adamantyl)-fluorene-9'-yl)(5-tert-butyl-1-phenyl-1,2,3,4-tetrahydropentalene)]zirconiumdichloride,
[1-(3,6-di-tert-butyl-2',7'-dimethylfluorene-9'-yl)(5-tert-butyl-1-phenyl-1,2,3,4-tetrahydropentalene)]zirconiumdichloride,
[1-(octamethylfluorene-12'-yl)(5-tert-butyl-1-phenyl-1,2,3,4-tetrahydropentalene)]zirconiumdichloride,
[1-(hexamethyldicyclopentafluorene-10'-yl)(5-tert-butyl-1-phenyl-1,2,3,4-tetrahydropentalene)]zirconiumdichloride,
[1-(fluorene-9'-yl)(5-adamantane-1-yl-1-methyl-1,2,3,4-tetrahydropentalene)]zirconiumdichloride,
[1-(2',7'-di-tert-butylfluorene-9'-yl)(5-adamantane-1-yl-1-methyl-1,2,3,4-tetrahydropentalene)]zirconiumdichloride,
[1-(3',6'-di-tert-butylfluorene-9'-yl)(5-adamantane-1-yl-1-methyl-1,2,3,4-tetrahydropentalene)]zirconiumdichloride,
[1-(3',6'-di-(1-adamantyl)-fluorene-9'-yl)(5-adamantane-1-yl-1-methyl-1,2,3,4-tetrahydropentalene)]zirconiumdichloride
[1-(3',6'-di-tert-butyl-2',7'-dimethylfluorene-9'-yl)(5-adamantane-1-yl-1-methyl-1,2,3,4-tetrahydropentalene)]zirconiumdichloride,
[1-(octamethylfluorene-12'-yl)(5-adamantane-1-yl-1-methyl-1,2,3,4-tetrahydropentalene)]zirconiumdichloride,
[1-(hexamethyldicyclopentafluorene-10'-yl)(5-adamantane-1-yl-1-methyl-1,2,3,4-tetrahydropentalene)]zirconiumdichloride,
[1-(fluorene-9'-yl)(5-(1-methylcyclohexyl)-1-methyl-1,2,3,4-tetrahydropentalene)]zirconiumdichloride,
[1-(2',7'-di-tert-butylfluorene-9'-yl)(5-(1-methylcyclohexyl)-1-methyl-1,2,3,4-tetrahydropentalene)]zirconiumdichloride,
[1-(3',6'-di-(1-adamantyl)-fluorene-9'-yl)(5-(1-methylcyclohexyl)-1-methyl-1,2,3,4-tetrahydropentalene)]zirconiumdichloride,
[1-(3',6'-di-tert-butyl-2',7'-dimethylfluorene-9'-yl)(5-(1-methylcyclohexyl)-1-methyl-1,2,3,4-tetrahydropentalene)]zirconiumdichloride,
[1-octamethylfluorene-12'-yl)(5-(1-methylcyclohexyl)-1-methyl-1,2,3,4-tetrahydropentalene)]zirconiumdichloride,
[1-(hexamethyldicyclopentafluorene-10'-yl)(5-(1-methylcyclohexyl)-1-methyl-1,2,3,4-tetrahydropentalene)]zirconiumdichloride,
[1-(fluorene-9'-yl)(5-tert-butyl-1-ethyl-1,2,3,4-tetrahydropentalene)]zirconiumdichloride,
[1-(2',7'-di-tert-butylfluorene-9'-yl)(5-tert-butyl-1-ethyl-1,2,3,4-tetrahydropentalene)]zirconiumdichloride,
[1-(3',6'-di-tert-butylfluorene-9'-yl)(5-tert-butyl-1-ethyl-1,2,3,4-tetrahydropentalene)]zirconiumdichloride,
[1-(3',6'-di-(1-adamantyl)-fluorene-9'-yl)(5-tert-butyl-1-ethyl-1,2,3,4-tetrahydropentalene)]zirconiumdichloride,
[1-(3',6'-di-tert-butyl-2',7'-dimethylfluorene-9'-yl)(5-tert-butyl-1-ethyl-1,2,3,4-tetrahydropentalene)]zirconiumdichloride,
[1-(octamethylfluorene-12'-yl)(5-tert-butyl-1-ethyl-1,2,3,4-tetrahydropentalene)]zirconiumdichloride,
[1-(hexamethyldicyclopentafluorene-10'-yl)(5-tert-butyl-1-ethyl-1,2,3,4-tetrahydropentalene)]zirconiumdichloride,
[1-(fluorene-9'-yl)(5-tert-butyl-1-iso-propyl-1,2,3,4-tetrahydropentalene)]zirconiumdichloride,
[1-(2',7'-di-tert-butylfluorene-9'-yl)(5-tert-butyl-1-iso-propyl-1,2,3,4-tetrahydropentalene)]zirconiumdichloride,
[1-(3',6'-di-tert-butylfluorene-9'-yl)(5-tert-butyl-1-iso-propyl-1,2,3,4-tetrahydropentalene)]zirconiumdichloride,
[1-(3',6'-di-(1-adamantyl)-fluorene-9'-yl)(5-tert-butyl-1-iso-propyl-1,2,3,4-tetrahydropentalene)]zirconiumdichloride,
[1-(3',6'-di-tert-buty-2',7'-dimethylfluorene-9'-yl)(5-tert-butyl-1-iso-propyl-1,2, 3,4-tetrahydropentalene)]zirconiumdichloride,
[1-(octamethylfluorene-12'-yl)(5-tert-butyl-1-iso-propyl-1,2,3,4-tetrahydropentalene)]zirconiumdichloride,
[1-(hexamethyldicyclopentafluorene-10'-yl)(5-tert-butyl-1-iso-propyl-1,2,3,4-tetrahydropentalene)]zirconiumdichloride,
[1-(fluorene-9'-yl)(5-adamantane-1-yl-1-iso-propyl-1,2,3,4-tetrahydropentalene)]zirconiumdichloride,
[1-(2',7'-di-tert-butylfluorene-9'-yl)(5-adamantane-1-yl-1-iso-propyl-1,2,3,4-tetrahydropentalene)]zirconiumdichloride,
[1-(3',6'-di-tert-butylfluorene-9'-yl)(5-adamantane-1-yl-1-iso-propyl-1,2,3,4-tetrahydropentalene)]zirconiumdichloride,
[1-(3',6'-di-(1-adamantyl)-fluorene-9'-yl)(5-adamantane-1-yl-1-iso-propyl-1,2,3,4-tetrahydropentalene)]zirconiumdichloride,
[1-(3',6'-di-tert-butyl-2',7'-dimethylfluorene-9'-yl)(5-adamantane-1-yl-1-iso-propyl-1,2,3,4-tetrahydropentalene)]zirconiumdichloride,
[1-(octamethylfluorene-12'-yl)(5-adamantane-1-yl-1-iso-propyl-1,2,3,4-tetrahydropentalene)]zirconiumdichloride,
[1-(hexamethyldicyclopentafluorene-10'-yl)(5-adamantane-1-yl-1-iso-propyl-1,2,3,4-tetrahydropentalene)]zirconiumdichloride,
[1-(fluorene-9'-yl)(1,5-di-tert-butyl-1,2,3,4-tetrahydropentalene)]zirconiumdichloride,
[1-(2',7'-di-tert-butylfluorene-9'-yl)(1,5-di-tert-butyl-1,2,3,4-tetrahydropentalene)]zirconiumdichloride,
[1-(3',6'-di-tert-butylfluorene-9'-yl)(1,5-di-tert-butyl-1,2,3,4-tetrahydropentalene)]zirconiumdichloride,
[1-(3',6'-di-(1-adamantyl)-fluorene-9'-yl)(1,5-di-tert-butyl-1,2,3,4-tetrahydropentalene)]zirconiumdichloride,
[1-(3',6'-di-tert-butyl-2',7'-dimethylfluorene-9'-yl)(1,5-di-tert-butyl-1,2,3,4-tetrahydropentalene)]zirconiumdichloride,
[1-(octamethylfluorene-12'-yl)(1,5-di-tert-butyl-1,2,3,4-tetrahydropentalene)]zirconiumdichloride,
[1-(hexamethyldicyclopentafluorene-10'-yl)(1,5-di-tert-butyl-1,2,3,4-tetrahydropentalene)]zirconiumdichloride,
[1-(fluorene-9'-yl)(5-tert-butyl-1-tert-butyl-1,2,3,4-tetrahydropentalene)]zirconiumdichloride,
[1-(2',7'-di-tert-butylfluorene-9'-yl)(5-tert-butyl-1-tert-butyl-1,2,3,4-tetrahydropentalene)]zirconiumdichloride,
[1-(3',6'-di-tert-butylfluorene-9'-yl)(5-tert-butyl-1-tert-butyl-1,2,3,4-tetrahydropentalene)]zirconiumdichloride,
[1-(3',6'-di-(1-adamantyl)-fluorene-9'-yl)(5-tert-butyl-1-tert-butyl-1,2,3,4-tetrahydropentalene)]zirconiumdichloride,
[1-(3',6'-di-tert-butyl-2',7-dimethylfluorene-9'-yl)(5-tert-butyl-1-tert-butyl-1,2,3,4-tetrahydropentalene)]zirconiumdichloride,
[1-(octamethylfluorene-12'-yl)(5-tert-butyl-1-tert-butyl-1,2,3,4-tetrahydropentalene)]zirconiumdichloride,
[1-(hexamethyldicyclopentafluorene-10'-yl)(5-tert-butyl-1-tert-butyl-1,2,3,4-tetrahydropentalene)]zirconiumdichloride,
[1-(fluorene-9'-yl)(5-tert-butyl-1,3-dimethyl-1,2,3,4-tetrahydropentalene)]zirconiumdichloride,

[1-(2',7'-di-tert-butylfluorene-9'-yl)(5-tert-butyl-1,3-dimethyl-1,2,3,4-tetrahydropentalene)]zirconiumdichloride,
[1-(3',6'-di-tert-butylfluorene-9'-yl)(5-tert-butyl-1,3-dimethyl-1,2,3,4-tetrahydropentalene)]zirconiumdichloride,
[1-(3',6'-di-(1-adamantyl)-fluorene-9'-yl)(5-tert-butyl-1,3-dimethyl-1,2,3,4-tetrahydropentalene)]zirconiumdichloride,
[1-(3',6'-di-tert-butyl-2',7'-dimethylfluorene-9'-yl)(5-tert-butyl-1,3-dimethyl-1,2,3,4-tetrahydropentalene)]zirconiumdichloride,
[1-(octamethylfluorene-12'-yl)(5-tert-butyl-1,3-dimethyl-1,2,3,4-tetrahydropentalene)]zirconiumdichloride,
[1-(hexamethyldicyclopentafluorene-10'-yl)(5-tert-butyl-1,3-dimethyl-1,2,3,4-tetrahydropentalene)]zirconiumdichloride,
[1-(fluorene-9'-yl)(5-tert-butyl-1-iso-propyl-3-methyl-1,2,3,4-tetrahydropentalene)]zirconiumdichloride,
[1-(2',7'-di-tert-butylfluorene-9'-yl)(5-tert-butyl-1-iso-propyl-3-methyl-1,2,3,4-tetrahydropentalene)]zirconiumdichloride,
[1-(3',6'-di-tert-butylfluorene-9'-yl)(5-tert-butyl-1-iso-propyl-3-methyl-1,2,3,4-tetrahydropentalene)]zirconiumdichloride,
[1-(3',6'-di-(1-adamantyl)-fluorene-9'-yl)(5-tert-butyl-1-iso-propyl-3-methyl-1,2,3,4-tetrahydropentalene)]zirconiumdichloride,
[1-(3',6'-di-tert-butyl-2',7'-dimethylfluorene-9'-yl)(5-tert-butyl-1-iso-propyl-3-methyl-1,2,3,4-tetrahydropentalene)]zirconiumdichloride,
[1-(hexamethyldicyclopentafluorene-10'-yl)(5-tert-butyl-1-iso-propyl-3-methyl-1,2,3,4-tetrahydropentalene)]zirconiumdichloride,
[1-(fluorene-9'-yl)(1,5-di-tert-butyl-3-methyl-1,2,3,4-tetrahydropentalene)]zirconiumdichloride,
[1-(2',7'-di-tert-butylfluorene-9'-yl)(1,5-di-tert-butyl-3-methyl-1,2,3,4-tetrahydropentalene)]zirconiumdichloride,
[1-(3',6'-di-tert-butylfluorene-9'-yl)(1,5-di-tert-butyl-3-methyl-1,2,3,4-tetrahydropentalene)]zirconiumdichloride,
[1-(3',6'-di-(1-adamantyl)-fluorene-9'-yl)(1,5-di-tert-butyl-3-methyl-1,2,3,4-tetrahydropentalene)]zirconiumdichloride,
[1-(3',6'-di-tert-butyl-2',7'-dimethylfluorene-9'-yl)(1,5-di-tert-butyl-3-methyl-1,2,3,4-tetrahydropentalene)]zirconiumdichloride,
[1-(octamethylfluorene-12'-yl)(1,5-di-tert-butyl-3-methyl-1,2,3,4-tetrahydropentalene)]zirconiumdichloride,
[1-(hexamethyldicyclopentafluorene-10'-yl)(1,5-di-tert-butyl-3-methyl-1,2,3,4-tetrahydropentalene)]zirconiumdichloride,
[1-(fluorene-9'-yl)(5-tert-butyl-1-methyl-3-iso-propyl-1,2,3,4-tetrahydropentalene)]zirconiumdichloride,
[1-(2',7'-di-tert-butylfluorene-9'-yl)(5-tert-butyl-1-methyl-3-iso-propyl-1,2,3,4-tetrahydropentalene)]zirconiumdichloride,
[1-(3',6'-di-tert-butylfluorene-9'-yl)(5-tert-butyl-1-methyl-3-iso-propyl-1,2,3,4-tetrahydropentalene)]zirconiumdichloride,
[1-(3',6'-di-(1-adamantyl)-fluorene-9'-yl)(5-tert-butyl-1-methyl-3-iso-propyl-1,2,3,4-tetrahydropentalene)]zirconiumdichloride,
[1-(3',6'-di-tert-butyl-2',7'-dimethylfluorene-9'-yl)(5-tert-butyl-1-methyl-3-iso-propyl-1,2,3,4-tetrahydropentalene)]zirconiumdichloride,
[1-(octamethylfluorene-12'-yl)(5-tert-butyl-1-methyl-3-iso-propyl-1,2,3,4-tetrahydropentalene)]zirconiumdichloride,
[1-(hexamethyldicyclopentafluorene-10'-yl)(5-tert-butyl-1-methyl-3-iso-propyl-1,2,3,4-tetrahydropentalene)]zirconiumdichloride,
[1-(fluorene-9'-yl)(5-adamantane-1-yl-1,3-di-iso-propyl-1,2,3,4-tetrahydropentalene)]zirconiumdichloride,
[1-(2',7'-di-tert-butylfluorene-9'-yl)(5-adamantane-1-yl-1,3-di-iso-propyl-1,2,3,4-tetrahydropentalene)]zirconiumdichloride,
[1-(3',6'-di-tert-butylfluorene-9'-yl)(5-adamantane-1-yl-1,3-di-iso-propyl-1,2,3,4-tetrahydropentalene)]zirconiumdichloride,
[1-(3',6'-di-(1-adamantyl)-fluorene-9'-yl)(5-adamantane-1-yl-1,3-di-iso-propyl-1,2,3,4-tetrahydropentalene)]zirconiumdichloride,
[1-(3',6'-di-tert-butyl-2',7'-dimethylfluorene-9'-yl)(5-adamantane-1-yl-1,3-di-iso-propyl-1,2,3,4-tetrahydropentalene)]zirconiumdichloride,
[1-(octamethylfluorene-12'-yl)(5-adamantane-1-yl-1,3-di-iso-propyl-1,2,3,4-tetrahydropentalene)]zirconiumdichloride,
[1-(hexamethyldicyclopentafluorene-10'-yl)(5-adamantane-1-yl-1,3-di-iso-propyl-1,2,3,4-tetrahydropentalene)]zirconiumdichloride,
[1-(fluorene-9'-yl)(5-tert-butyl-1-ethyl-3-iso-propyl-1,2,3,4-tetrahydropentalene)]zirconiumdichloride,
[1-(2',7'-di-tert-butylfluorene-9'-yl)(5-tert-butyl-1-ethyl-3-iso-propyl-1,2,3,4-tetrahydropentalene)]zirconiumdichloride,
[1-(3',6'-di-tert-butylfluorene-9'-yl)(5-tert-butyl-1-ethyl-3-iso-propyl-1,2,3,4-tetrahydropentalene)]zirconiumdichloride,
[1-(3',6'-di-(1-adamantyl)-fluorene-9'-yl)(5-tert-butyl-1-ethyl-3-iso-propyl-1,2,3,4-tetrahydropentalene)]zirconiumdichloride,
[1-(3',6'-di-tert-butyl-2',7'-dimethylfluorene-9'-yl)(5-tert-butyl-1-ethyl-3-iso-propyl-1,2,3,4-tetrahydropentalene)]zirconiumdichloride,
[1-(octamethylfluorene-12'-yl)(5-tert-butyl-1-ethyl-3-iso-propyl-1,2,3,4-tetrahydropentalene)]zirconiumdichloride,
[1-(hexamethyldicyclopentafluorene-10'-yl)(5-tert-butyl-1-ethyl-3-iso-propyl-1,2,3,4-tetrahydropentalene)]zirconiumdichloride,
[1-(fluorene-9'-yl)(5-tert-butyl-1,3-di-iso-propyl-1,2,3,4-tetrahydropentalene)]zirconiumdichloride,
[1-(2',7'-di-tert-butylfluorene-9'-yl)(5-tert-butyl-1,3-di-iso-propyl-1,2,3,4-tetrahydropentalene)]zirconiumdichloride,
[1-(3',6'-di-tert-butylfluorene-9'-yl)(5-tert-butyl-1,3-di-iso-propyl-1,2,3,4-tetrahydropentalene)]zirconiumdichloride,
[1-(3',6'-di-(1-adamantyl)-fluorene-9'-yl)(5-tert-butyl-1,3-di-iso-propyl-1,2,3,4-tetrahydropentalene)]zirconiumdichloride,
[1-(3',6'-di-tert-butyl-2',7'-dimethylfluorene-9'-yl)(5-tert-butyl-1,3-di-iso-propy-1,2,3,4-tetrahydropentalene)]zirconiumdichloride,
[1-(octamethylfluorene-12'-yl)(5-tert-butyl-1,3-di-iso-propyl-1,2,3,4-tetrahydropentalene)]zirconiumdichloride,
[1-(hexamethyldicyclopentafluorene-10'-yl)(5-tert-butyl-1,3-di-iso-propyl-1,2,3,4-tetrahydropentalene)]zirconiumdichloride,
[1-(fluorene-9'-yl)(1,5-di-tert-butyl-3-iso-propyl-1,2,3,4-tetrahydropentalene)]zirconiumdichloride,
[1-(2',7'-di-tert-butylfluorene-9'-yl)(1,5-di-tert-butyl-3-iso-propyl-1,2,3,4-tetrahydropentalene)]zirconiumdichloride,
[1-(3',6'-di-tert-butylfluorene-9'-yl)(1,5-di-tert-butyl-3-iso-propyl-1,2,3,4-tetrahydropentalene)]zirconiumdichloride,
[1-(3',6'-di-(1-adamantyl)-fluorene-9'-yl)(1,5-di-tert-butyl-3-iso-propyl-1,2,3,4-tetrahydropentalene)]zirconiumdichloride,

[1-(3',6'-di-tert-butyl-2',7'-dimethylfluorene-9'-yl)(1,5-di-tert-butyl-3-iso-propyl-1,2,3,4-tetrahydropentalene)]zirconiumdichloride,
[1-(octamethylfluorene-12'-yl)(1,5-di-tert-butyl-3-iso-propyl-1,2,3,4-tetrahydropentalene)]zirconiumdichloride,
[1-(hexamethyldicyclopentafluorene-10'-yl)(1,5-di-tert-butyl-3-iso-propyl-1,2,3,4-tetrahydropentalene)]zirconiumdichloride,
[1-(fluorene-9'-yl)(3, 5-tert-butyl-1-methyl-1,2, 3,4-tetrahydropentalene)]zirconiumdichloride,
[1-(2',7'-di-tert-butylfluorene-9'-yl)(3,5-tert-butyl-1-methyl-1,2,3,4-tetrahydropentalene)]zirconiumdichloride,
[1-(3',6'-di-tert-butylfluorene-9'-yl)(3,5-tert-butyl-1-methyl-1,2,3,4-tetrahydropentalene)]zirconiumdichloride,
[1-(3',6-di-(1-adamantyl)-fluorene-9'-yl)(3,5-tert-butyl-1-methyl-1,2,3,4'-tetrahydropentalene)]zirconiumdichloride,
[1-(3',6'-di-tert-butyl-2',7'-dimethylfluorene-9'-yl)(3,5-tert-butyl-1-methyl-1,2,3,4-tetrahydropentalene)]zirconiumdichloride,
[1-(octamethylfluorene-12'-yl)(3,5-tert-butyl-1-methyl-1,2,3,4-tetrahydropentalene)]zirconiumdichloride,
[1-(hexamethyldicyclopentafluorene-10'-yl)(3,5-tert-butyl-1-methyl-1,2,3,4-tetrahydropentalene)]zirconiumdichloride,
[1-(fluorene-9'-yl)(5-adamantane-1-yl-1-iso-propyl-3-tert-butyl-1,2,3,4-tetrahydropentalene)]zirconiumdichloride,
[1-(2',7'-di-tert-butylfluorene-9'-yl)(5-adamantane-1-yl-1-iso-propyl-3-tert-butyl-1,2,3,4-tetrahydropentalene)]zirconiumdichloride,
[1-(3',6'-di-tert-butylfluorene-9'-yl)(5-adamantane-1-yl-1-iso-propyl-3-tert-butyl-1,2,3,4-tetrahydropentalene)]zirconiumdichloride,
[1-(3',6'-di(1-adamantyl)-fluorene-9'-yl)(5-adamantane-1-yl-1-iso-propyl-3-tert-butyl-1,2,3,4-tetrahydropentalene)]zirconiumdichloride,
[1-(3',6'-di-tert-butyl-2',7'-dimethylfluorene-9'-yl)(5-adamantane-1-yl-1-iso-propyl-3-tert-butyl-1,2,3,4-tetrahydro pentalene)]zirconiumdichloride,
[1-(octamethylfluorene-12'-yl)(5-adamantane-1-yl-1-iso-propyl-3-tert-butyl-1,2,3,4-tetrahydropentalene)]zirconiumdichloride,
[1-(hexamethyldicyclopentafluorene-10'-yl)(5-adamantane-1-yl-1-iso-propyl-3-tert-butyl-1,2,3,4-tetrahydropentalene)]zirconiumdichloride,
[1-(fluorene-9'-yl)(3,5-tert-butyl-1-ethyl-1,2,3,4-tetrahydropentalene)]zirconiumdichloride,
[1-(2',7'-di-tert-butylfluorene-9'-yl)(3,5-tert-butyl-1-ethyl-1,2,3,4-tetrahydropentalene)]zirconiumdichloride,
[1-(3',6'-di-tert-butylfluorene-9'-yl)(3,5-tert-butyl-1-ethyl-1,2,3,4-tetrahydropentalene)]zirconiumdichloride,
[1-(3',6-di-(1-adamantyl)-fluorene-9'-yl)(3,5-tert-butyl-1-ethyl-1,2,3,4-tetrahydropentalene)]zirconiumdichloride,
[1-(3',6'-di-tert-butyl-2',7'-dimethylfluorene-9'-yl)(3,5-tert-butyl-1-ethyl-1,2,3,4-tetrahydropentalene)]zirconiumdichloride
[1-(octamethylfluorene-12'-yl)(3,5-tert-butyl-1-ethyl-1,2,3,4-tetrahydropentalene)]zirconiumdichloride,
[1-(hexamethyldicyclopentafluorene-10'-yl)(3,5-tert-butyl-1-ethyl-1,2,3,4-tetrahydropentalene)]zirconiumdichloride,
[1-(fluorene-9'-yl)(3,5-tert-butyl-1-iso-propyl-1,2, 3,4-tetrahydropentalene)]zirconiumdichloride,
[1-(2',7'-di-tert-butylfluorene-9'-yl)(3,5-tert-butyl-1-iso-propyl-1,2,3,4-tetrahydropentalene)]zirconiumdichloride,
[1-(3',6'-di-tert-butylfluorene-9'-yl)(3,5-tert-butyl-1-iso-propyl-1,2,3,4'-tetrahydropentalene)]zirconiumdichloride,
[1-(3,6-di-(1-adamantyl)-fluorene-9'-yl)(3,5-tert-butyl-1-iso-propyl-1,2,3,4-tetrahydropentalene)]zirconiumdichloride,
[1-(3',6'-di-tert-butyl-2',7'-dimethylfluorene-9'-yl)(3,5-tert-butyl-1-iso-propyl-1,2,3,4-tetrahydropentalene)]zirconiumdichloride,
[1-(octamethylfluorene-12'-yl)(3,5-tert-butyl-1-iso-propyl-1,2,3,4-tetrahydropentalene)]zirconiumdichloride,
[1-(hexamethyldicyclopentafluorene-10'-yl)(3,5-tert-butyl-1-iso-propyl-1,2,3,4-tetrahydropentalene)]zirconiumdichloride,
[1-(fluorene-9'-yl)(5-tert-butyl-1-methyl-3-cyclohexyl-1,2, 3,4-tetrahydropentalene)]zirconiumdichloride,
[1-(2',7'-di-tert-butylfluorene-9'-yl)(5-tert-butyl-1-methyl-3-cylohexyl-1,2,3,4-tetrahydropentalene)]zirconiumdichloride,
[1-(3',6'-di-tert-butylfluorene-9'-yl)(5-tert-butyl-1-methyl-3-cylohexyl-1,2,3,4-tetrahydropentalene)]zirconiumdichloride,
[1-(3',6-di-(1-adamantyl)-fluorene-9'-yl)(5-tert-butyl-1-methyl-3-cylohexyl-1,2,3,4-tetrahydropentalene)]zirconiumdichloride,
[1-(3',6'-di-tert-butyl-2',7'-dimethylfluorene-9'-yl)(5-tert-butyl-1-methyl-3-cylohexyl-1,2,3,4-tetrahydropentalene)]zirconiumdichloride,
[1-(octamethylfluorene-12'-yl)(5-tert-butyl-1-methyl-3-cylohexyl-1,2,3,4-tetrahydropentalene)]zirconiumdichloride,
[1-(hexamethyldicyclopentafluorene-10'-yl)(5-tert-butyl-1-methyl-3-cylohexyl-1,2,3,4-tetrahydropentalene)]zirconiumdichloride,
[1-(fluorene-9'-yl)(5-adamantane-1-yl-1-iso-propyl-3-cylohexyl-1,2,3,4-tetrahydropentalene)]zirconiumdichloride,
[1-(2',7'-di-tert-butylfluorene-9'-yl)(5-adamantane-1-yl-1-iso-propyl-3-cylohexyl-1,2,3,4-tetrahydropentalene)]zirconiumdichloride,
[1-(3',6'-di-tert-butylfluorene-9'-yl)(5-adamantane-1-yl-1-iso-propyl-3-cylohexyl-1,2,3,4-tetrahydropentalene)]zirconiumdichloride
[1-(3',6'-di-(1-adamantyl)-fluorene-9'-yl)(5-adamantane-1-yl-1-iso-propyl-3-cylohexyl-1,2,3,4-tetrahydropentalene)]zirconiumdichloride,
[1-(3',6'-di-tert-butyl-2',7'-dimethylfluorene-9'-yl)(5-adamantane-1-yl-1-iso-propyl-3-cylohexyl-1,2,3,4-tetrahydropentalene)]zirconiumdichloride,
[1-(octamethylfluorene-12'-yl)(5-adamantane-1-yl-1-iso-propyl-3-cylohexyl-1,2,3,4-tetrahydropentalene)]zirconiumdichloride,
[1-(hexamethyldicyclopentafluorene-10'-yl)(5-adamantane-1-yl-1-iso-propyl-3-cylohexyl-1,2,3,4-tetrahydropentalene)]zirconiumdichloride,
[1-(fluorene-9'-yl)(5-tert-butyl-1-ethyl-3-cylohexyl-1,2,3,4-tetrahydropentalene)]zirconiumdichloride,
[1-(2',7'-di-tert-butylfluorene-9'-yl)(5-tert-butyl-1-ethyl-3-cylohexyl-1,2,3,4-tetrahydropentalene)]zirconiumdichloride,
[1-(3',6'-di-tert-butylfluorene-9'-yl)(5-tert-butyl-1-ethyl-3-cylohexyl-1,2,3,4-tetrahydropentalene)]zirconiumdichloride,
[1-(3',6'-di-(1-adamantyl)-fluorene-9'-yl)(5-tert-butyl-1-ethyl-3-cylohexyl-1,2,3,4-tetrahydropentalene)]zirconiumdichloride,

[1-(3',6'-di-tert-butyl-2',7'-dimethylfluorene-9'-yl)(5-tert-butyl-1-ethyl-3-cylohexyl-1,2,3,4-tetrahydropentalene)]zirconiumdichloride,
[1-(octamethylfluorene-12'-yl)(5-tert-butyl-1-ethyl-3-cylohexyl-1,2,3,4-tetrahydropentalene)]zirconiumdichloride,
[1-(hexamethyldicyclopentafluorene-10'-yl)(5-tert-butyl-1-ethyl-3-cylohexyl-1,2,3,4-tetrahydropentalene)]zirconiumdichloride,
[1-(fluorene-9'-yl)(5-tert-butyl-1-iso-propyl-3-cylohexyl-1,2,3,4-tetrahydropentalene)]zirconiumdichloride,
[1-(2',7'-di-tert-butylfluorene-9'-yl)(5-tert-butyl-1-iso-propyl-3-cylohexyl-1,2,3,4-tetrahydropentalene)]zirconiumdichloride,
[1-(3',6'-di-tert-butylfluorene-9'-yl)(5-tert-butyl-1-iso-propyl-3-cylohexyl-1,2,3,4-tetrahydropentalene)]zirconiumdichloride,
[1-(3',6'-di-(1-adamantyl)-fluorene-9'-yl)(5-tert-butyl-1-iso-propyl-3-cylohexyl-1,2,3,4-tetrahydropentalene)]zirconiumdichloride,
[1-(3',6'-di-tert-butyl-2',7'-dimethylfluorene-9'-yl)(5-tert-butyl-1-iso-propyl-3-cylohexyl-1,2,3,4-tetrahydropentalene)]zirconiumdichloride,
[1-(octamethylfluorene-12'-yl)(5-tert-butyl-1-iso-propyl-3-cylohexyl-1,2,3,4-tetrahydropentalene)]zirconiumdichloride,
[1-(hexamethyldicyclopentafluorene-10'-yl)(5-tert-butyl-1-iso-propyl-3-cylohexyl-1,2,3,4-tetrahydropentalene)]zirconiumdichloride,
[1-(fluorene-9'-yl)(5-tert-butyl-1-methyl-3-(3-cyclohexenyl)-1,2,3,4-tetrahydropentalene)]zirconiumdichloride,
[1-(2',7'-di-tert-butylfluorene-9'-yl)(5-tert-butyl-1-methyl-3-(3-cyclohexenyl)-1,2,3,4-tetrahydropentalene)]zirconiumdichloride,
[1-(3',6'-di-tert-butylfluorene-9'-yl)(5-tert-butyl-1-methyl-3-(3-cyclohexenyl)-1,2,3,4-tetrahydropentalene)]zirconiumdichloride,
[1-(3',6'-di-(1-adamantyl)-fluorene-9'-yl)(5-tert-butyl-1-methyl-3-(3-cyclohexenyl)-1,2,3,4-tetrahydropentalene)]zirconiumdichloride,
[1-(3',6'-di-tert-butyl-2',7'-dimethylfluorene-9'-yl)(5-tert-butyl-1-methyl-3-(3-cyclohexenyl)-1,2,3,4-tetrahydropentalene)]zirconiumdichloride,
[1-(octamethylfluorene-12'-yl)(5-tert-butyl-1-methyl-3-(3-cyclohexenyl)-1,2,3,4-tetrahydropentalene)]zirconiumdichloride,
[1-(hexamethyldicyclopentafluorene-10'-yl)(5-tert-butyl-1-methyl-3-(3-cyclohexenyl)-1,2,3,4-tetrahydropentalene)]zirconiumdichloride,
[1-(fluorene-9'-yl)(5-adamantane-1-yl-1-iso-propyl-3-(3-cyclohexenyl)-1,2,3,4-tetrahydropentalene)]zirconiumdichloride,
[1-(2',7'-di-tert-butylfluorene-9'-yl)(5-adamantane-1-yl-1-iso-propyl-3-(3-cyclohexenyl)-1,2,3,4-tetrahydropentalene)]zirconiumdichloride,
[1-(3',6'-di-tert-butylfluorene-9'-yl)(5-adamantane-1-yl-1-iso-propyl-3-(3-cyclohexenyl)-1,2,3,4-tetrahydropentalene]zirconiumdichloride,
[1-(3',6-di-(1-adamantyl)-fluorene-9'-yl)(5-adamantane-1-yl-1-iso-propyl-3-(3-cyclohexenyl)-1,2,3,4-tetrahydropentalene)]zirconiumdichloride,
[1-(3',6'-di-tert-butyl-2',7'-dimethylfluorene-9'-yl)(5-adamantane-1-yl-1-iso-propyl-3-(3-cyclohexenyl)-1,2,3,4-tetrahydropentalene) ]zirconiumdichloride,
[1-(octamethylfluorene-12'-yl)(5-adamantane-1-yl-1-iso-propyl-3-(3-cyclohexenyl)-1,2,3,4-tetrahydropentalene)]zirconiumdichloride,
[1-(hexamethyldicyclopentafluorene-10'-yl)(5-adamantane-1-yl-1-iso-propyl-3-(cyclohexenyl)-1,2,3,4-tetrahydropentalene)]zirconiumdichloride,
[1-(fluorene-9'-yl)(5-tert-butyl-1-ethyl-3-(3-cyclohexenyl)-1, 2, 3,4-tetrahydropentalene)]zirconiumdichloride,
[1-(2',7'-di-tert-butylfluorene-9'-yl)(5-tert-butyl-1-ethyl-3-(3-cyclohexenyl)-1,2,3,4-tetrahydropentalene)]zirconiumdichloride,
[1-(3',6'-di-tert-butylfluorene-9'-yl)(5-tert-butyl-1-ethyl-3-(3-cyclohexenyl)-1,2,3,4-tetrahydropentalene)]zirconiumdichloride,
[1-(3',6-di-(1-adamantyl)-fluorene-9'-yl)(5-tert-butyl-1-ethyl-3-(3-cyclohexenyl)-1,2,3,4-tetrahydropentalene)]zirconiumdichloride,
[1-(3',6'-di-tert-butyl-2',7'-dimethylfluorene-9'-yl)(5-tert-butyl-1-ethyl-3-(3-cyclohexenyl)-1,2,3,4-tetrahydropentalene)]zirconiumdichloride,
[1-(octamethylfluorene-12'-yl)(5-tert-butyl-1-ethyl-3-(3-cyclohexenyl)-1,2,3,4-tetrahydropentalene)]zirconiumdichloride,
[1-(hexamethyldicyclopentafluorene-10'-yl)(5-tert-butyl-1-ethyl-3-(3-cyclohexenyl)-1,2,3,4-tetrahydropentalene)]zirconiumdichloride,
[1-(fluorene-9'-yl)(5-tert-butyl-1-iso-propyl-3-(3-cyclohexenyl)-1,2,3,4-tetrahydropentalene)]zirconiumdichloride,
[1-(2',7'-di-tert-butylfluorene-9'-yl)(5-tert-butyl-1-iso-propyl-3-(3-cyclohexenyl)-1,2,3,4-tetrahydropentalene)]zirconiumdichloride,
[1-(3',6'-di-tert-butylfluorene-9'-yl)(5-tert-butyl-1-iso-propyl-3-(3-cyclohexenyl)-1,2,3,4-tetrahydropentalene)]zirconiumdichloride,
[1-(3',6'-di-(1-adamantyl)-fluorene-9'-yl)(5-tert-butyl-1-iso-propyl-3-(3-cyclohexenyl)-1,2,3,4-tetrahydropentalene)]zirconiumdichloride,
[1-(3',6'-di-tert-butyl-2',7'-dimethylfluorene-9'-yl)(5-tert-butyl-1-iso-propyl-3-(3-cyclohexenyl)-1,2,3,4-tetrahydropentalene)]zirconiumdichloride,
[1-(octamethylfluorene-12'-yl)(5-tert-butyl-1-iso-propyl-3-(3-cyclohexenyl)-1,2,3,4-tetrahydropentalene)]zirconiumdichloride,
[1-(hexamethyldicyclopentafluorene-10'-yl)(5-tert-butyl-1-iso-propyl-3-(3-cyclohexenyl)-1,2,3,4-tetrahydropentalene)]zirconiumdichloride,
[1-(fluorene-9'-yl)(5-tert-butyl-1-methyl-3-(bicyclo[2.2.1]hepta-5-ene-2-yl)-1,2,3,4-tetrahydropentalene)]zirconiumdichloride,
[1-(2',7'-di-tert-butylfluorene-9'-yl)(5-tert-butyl-1-methyl-3-(bicyclo[2.2.1]hepta-5-ene-2-yl)-1,2,3,4-tetrahydropentalene)]zirconiumdichloride,
[1-(3',6'-di-tert-butylfluorene-9'-yl)(5-tert-butyl-1-methyl-3-(bicyclo[2.2.1]hepta-5-ene-2-yl)-1,2,3,4-tetrahydropentalene)]zirconiumdichloride,
[1-(3',6'-di-(1-adamantyl)-fluorene-9'-yl)(5-tert-butyl-1-methyl-3-(bicyclo[2.2.1]hepta-5-ene-2-yl)-1,2,3,4-tetrahydropentalene)]zirconiumdichloride,
[1-(3',6'-di-tert-butyl-2',7'-dimethylfluorene-9'-yl)(5-tert-butyl-1-methyl-3-(bicyclo[2.2.1]hepta-5-ene-2-yl)-1,2,3,4-tetrahydropentalene)]zirconiumdichloride,
[1-(octamethylfluorene-12'-yl)(5-tert-butyl-1-methyl-3-(bicyclo[2.2.1]hepta-5-ene-2-yl)-1,2,3,4-tetrahydropentalene)]zirconiumdichloride,
[1-(hexamethyldicyclopentafluorene-10'-yl)(5-tert-butyl-1-methyl-3-(bicyclo[2.2.1]hepta-5-ene-2-yl)-1,2,3,4-tetrahydropentalene)]zirconiumdichloride,
[1-(fluorene-9'-yl)(5-adamantane-1-yl-1-iso-propyl-3-(bicyclo[2.2.1]hepta-5-ene-2-yl)-1,2,3,4-tetrahydropentalene)]zirconiumdichloride,

[1-(2',7'-di-tert-butylfluorene-9'-yl)(5-adamantine-1-yl-1-iso-propyl-3-(bicyclo[2.2.1]hepta-5-ene-2-yl)-1,2,3,4-tetrahydropentalene)]zirconiumdichloride,

[1-(3',6'-di-tert-butylfluorene-9'-yl)(5-adamantane-1-yl-1-iso-propyl-3-(bicyclo[2.2.1]hepta-5-ene-2-yl)-1,2,3,4-tetrahydropentalene)]zirconiumdichloride,

[1-(3',6'-di-(1-adamantyl)-fluorene-9'-yl)(S-adamantane-1-yl-1-iso-propyl-3-(bicyclo[2.2.1]hepta-5-ene-2-yl)-1,2,3,4-tetrahydropentalene)]zirconiumdichloride,

[1-(3',6'-di-tert-butyl-2',7'-dimethylfluorene-9'-yl)(5-adamantane-1-yl-1-iso-propyl-3-(bicyclo[2.2.1]hepta-5-ene-2-yl)-1,2,3,4-tetrahydropentalene)]zirconiumdichloride,

[1-(octamethylfluorene-12'-yl)(5-adamantane-1-yl-1-iso-propyl-3-(bicyclo[2.2.1]hepta-5-ene-2-yl)-1,2,3,4-tetrahydropentalene)]zirconiumdichloride,

[1-(hexamethyldicyclopentafluorene-10'-yl)(5-adamantane-1-yl-1-iso-propyl-3-(bicyclo[2.2.1]hepta-5-ene-2-yl)-1,2,3,4-tetrahydropentalene)]zirconiumdichloride,

[1-(fluorene-9'-yl)(5-tert-butyl-1-iso-propyl-3-(bicyclo[2.2.1]hepta-5-ene-2-yl)-1,2,3,4-tetrahydropentalene)]zirconiumdichloride,

[1-(2',7'-di-tert-butylfluorene-9'-yl)(5-tert-butyl-1-iso-propyl-3-(bicyclo[2.2.1]hepta-5-ene-2-yl)-1,2,3,4-tetrahydropentalene)]zirconiumdichloride,

[1-(3',6'-di-tert-butylfluorene-9'-yl)(5-tert-butyl-1-iso-propyl-3-(bicyclo[2.2.1]hepta-5-ene-2-yl)-1,2,3,4-tetrahydropentalene)]zirconiumdichloride,

[1-(3',6-di-(1-adamantyl)-fluorene-9'-yl)(5-tert-butyl-1-iso-propyl-3-(bicyclo[2.2.1]hepta-5-ene-2-yl)-1,2,3,4-tetrahydropentalene)]zirconiumdichloride,

[1-(3',6'-di-tert-butyl-2',7'-dimethylfluorene-9'-yl)(5-tert-butyl-1-iso-propyl-3-(bicyclo[2.2.1]hepta-5-ene-2-yl)-1,2,3,4-tetrahydropentalene)]zirconiumdichloride,

[1-(octamethylfluorene-12'-yl)(5-tert-butyl-1-iso-propyl-3-(bicyclo[2.2.1]hepta-5-ene-2-yl)-1,2,3,4-tetrahydropentalene)]1 zirconiumdichloride,

[1-(hexamethyldicyclopentafluorene-10'-yl)(5-tert-butyl-1-iso-propyl-3-(bicyclo[2.2.1]hepta-5-ene-2-yl)-1,2,3,4-tetrahydropentalene)]zirconiumdichloride,

[8-(fluorene-9'-yl)(3,3b,4,5,6,7,7a,8-octahydrocyclopenta[a]indene)]zirconiumdichloride,

[8-(2',7'-di-tert-butylfluorene-9'-yl)(3,3b,4,5,6,7,7a,8-octahydrocyclopenta[a]indene)]zirconiumdichloride,

[8-(3',6'-di-tert-butylfluorene-9'-yl)(3,3b,4,5,6,7,7a,8-octahydrocyclopenta[a]indene)]zirconiumdichloride,

[8-(3',6'-di-(1-adamantyl)-fluorene-9'-yl)(3,3b,4,5,6,7,7a,8-octahydrocyclopenta[a]indene)]zirconiumdichloride,

[8-(3',6'-di-tert-butyl-2',7'-dimethylfluorene-9'-yl)(3,3b,4,5,6,7,7a,8-octahydrocyclopenta[a]indene)]zirconiumdichloride,

[8-(octamethylfluorene-12'-yl)(3,3b,4,5,6,7,7a,8-octahydrocyclopenta[a]indene)]zirconiumdichloride,

[8-(hexamethyldicyclopentafluorene-10'-yl)(3,3b,4,5,6,7,7a,8-octahydrocyclopenta[a]indene)]zirconiumdichloride,

[8-(fluorene-9'-yl)(2-tert-butyl-8-methyl-3,3b,4,5,6,7,7a,8-octahydrocyclopenta[a]indene)]zirconiumdichloride,

[8-(2',7'-di-tert-butylfluorene-9'-yl)(2-tert-butyl-8-methyl-3,3b,4,5,6,7,7a,8-octahydrocyclopenta[a]indene)]zirconiumdichloride,

[8-(3',6'-di-tert-butylfluorene-9'-yl)(2-tert-1-butyl-8-methyl-3,3b,4,5,6,7,7a,8-octahydrocyclopenta[a]indene)]zirconiumdichloride,

[8-(3',6'-di-(1-adamantyl)-fluorene-9'-yl)(2-tert-butyl-8-methyl-3,3b,4,5,6,7,7a,8-octahydrocyclopenta[a]indene)]zirconiumdichloride,

[8-(3',6'-di-tert-butyl-2',7'-dimethylfluorene-9'-yl)(2-tert-butyl-8-methyl-3,3b,4,5,6,7,7a,8-octahydrocyclopenta[a]indene)]zirconiumdichloride,

[8-(octamethylfluorene-12'-yl)(2-tert-butyl-8-methyl-3,3b,4,5,6,7,7a,8-octahydrocyclopenta[a]indene)]zirconiumdichloride,

[8-(hexamethyldicyclopentafluorene-10'-yl)(2-tert-butyl-8-methyl-3,3b,4,5,6,7,7a,8-octahydrocyclopenta[a]indene)]zirconiumdichloride,

[8-(fluorene-9'-yl)(2-tert-butyl-8-iso-propyl-3,3b,4,5,6,7,7a,8-octahydrocyclopenta[a]indene)]zirconiumdichloride,

[8-(2',7'-di-tert-butylfluorene-9'-yl)(2-tert-butyl-8-iso-propyl-3,3b,4,5,6,7,7a,8-octahydrocyclopenta[a]indene)]zirconiumdichloride,

[8-(3',6'-di-tert-butylfluorene-9'-yl)(2-tert-butyl-8-iso-propyl-3,3b,4,5,6,7,7a,8-octahydrocyclopenta[a]indene)]zirconiumdichloride,

[8-(3',6-di-(1-adamantyl)-fluorene-9'-yl)(2-tert-butyl-8-iso-propyl-3,3b,4,5,6,7,7a,8-octahydrocyclopenta[a]indene)]zirconiumdichloride,

[8-(3',6'-di-tert-butyl-2',7'-dimethylfluorene-9'-yl)(2-tert-butyl-8-iso-propyl-3,3b,4,5,6,7,7a,8-octahydrocyclopenta[a]indene)]zirconiumdichloride,

[8-(octamethylfluorene-12'-yl)(2-tert-butyl-8-iso-propyl-3,3b,4,5,6,7,7a,8-octahydrocyclopenta[a]indene)]zirconiumdichloride,

[8-(hexamethyldicyclopentafluorene-10'-yl)(2-tert-butyl-8-iso-propyl-3,3b,4,5,6,7,7a,8-octahydrocyclopenta[a]indene)]zirconiumdichloride,

[8-(fluorene-9'-yl)(2-tert-butyl-8-phenyl-3,3b,4,5,6,7,7a,8-octahydrocyclopenta[a]indene)]zirconiumdichloride,

[8-(2',7'-di-tert-butylfluorene-9'-yl)(2-tert-butyl-8-phenyl-3,3b,4,5,6,7,7a,8-octahydrocyclopenta[a]indene)]zirconiumdichloride,

[8-(3',6'-di-tert-butylfluorene-9'-yl)(2-tert-butyl-8-phenyl-3,3b,4,5,6,7,7a,8-octahydrocyclopenta[a]indene)]zirconiumdichloride,

[8-(3',6'-di-(1-adamantyl)-fluorene-9'-yl)(2-tert-butyl-8-phenyl-3,3b,4,5,6,7,7a,8-octahydrocyclopenta[a]indene)]zirconiumdichloride,

[8-(3',6'-di-tert-butyl-2',7'-dimethylfluorene-9'-yl)(2-tert-butyl-8-phenyl-3,3b,4,5,6,7,7a,8-octahydrocyclopenta[a]indene)]zirconiumdichloride,

[8-(octamethylfluorene-12'-yl)(2-tert-butyl-8-phenyl-3,3b,4,5,6,7,7a,8-octahydrocyclopenta[a]indene)]zirconiumdichloride,

[8-(hexamethyldicyclopentafluorene-10'-yl)(2-tert-butyl-8-phenyl-3,3b,4,5,6,7,7a,8-octahydrocyclopenta[a]indene)]zirconiumdichloride,

[8-(fluorene-9'-yl)(2-tert-butyl-5,8-dimethyl-3,3b,4,5,6,7,7a,8-octahydrocyclopenta[a]indene)]zirconiumdichloride,

[8-(2',7'-di-tert-butylfluorene-9'-yl)(2-tert-butyl-5,8-dimethyl-3,3b,4,5,6,7,7a,8-octahydrocyclopenta[a]indene)]zirconiumdichloride

[8-(3',6'-di-tert-butylfluorene-9'-yl)(2-tert-butyl-5,8-dimethyl-3,3b,4,5,6,7,7a,8-octahydrocyclopenta[a]indene)]zirconiumdichloride,

[8-(3',6'-di-(1-adamantyl)-fluorene-9'-yl)(2-tert-butyl-5,8-dimethyl-3,3b,4,5,6,7,7a,8-octahydrocyclopenta[a]indene)]zirconiumdichloride,

[8-(3',6'-di-tert-butyl-2',7'-dimethylfluorene-9'-yl)(2-tert-butyl-5, 8-dimethyl-3,3b,4,5,6,7,7a,8-octahydrocyclopenta[a]indene)]zirconiumdichloride,

[8-(octamethylfluorene-12'-yl)(2-tert-butyl-5, 8-dimethyl-3,3b,4,5,6,7,7a,8-octahydrocyclopenta[a]indene)]zirconiumdichloride,

[8-(hexamethyldicyclopentafluorene-10'-yl)(2-tert-butyl-5,
8-dimethyl-3,3b,4,5,6,7,7a,8-octahydrocyclopenta[a]indene)]zirconiumdichloride,

[8-(fluorene-9'-yl)(2-tert-butyl-8-(3-cyclohexenyl)-3,3b,4,5,
6,7,7a,8-octahydrocyclopenta[a]indene)]zirconiumdichloride,

[8-(2',7'-di-tert-butylfluorene-9'-yl)(2-tert-butyl-8-(3-cyclohexenyl)-3,3b,4,5,6,7,7a,8-octahydrocyclopenta[a]indene)]zirconiumdichloride,

[8-(3',6'-di-tert-butylfluorene-9'-yl)(2-tert-butyl-8-(3-cyclohexenyl)-3,3b,4,5,6,7,7a,8-octahydrocyclopenta[a]indene)]zirconiumdichloride,

[8-(3',6'-di-(1-adamantyl)-fluorene-9'-yl)(2-tert-butyl-8-(3-cyclohexenyl)-3,3b,4,5,6,7,7a,8-octahydrocyclopenta[a]indene)]zirconiumdichloride,

[8-(3',6'-di-tert-butyl-2',7'-dimethylfluorene-9'-yl)(2-tert-butyl-8-(3-cyclohexenyl)-3,3b,4',5,6,7,7a,8-octahydrocyclopenta[a]indene)]zirconiumdichloride,

[8-(octamethylfluorene-12'-yl)(2-tert-butyl-8-(3-cyclohexenyl)-3,3b,4,5,6,7,7a,8-octahydrocyclopenta[a]indene)]zirconiumdichloride,

[8-(hexamethyldicyclopentafluorene-10'-yl)(2-tert-butyl-8-(3-cyclohexenyl)-3,3b,4,5,6,7,7a,8-octahydrocyclopenta[a]indene)]zirconiumdichloride,

[8-(fluorene-9'-yl)(2-(1-adamantyl)-8-methyl-3,3b,4,5,6,7,7a,8-octahydrocyclopenta[a]indene)]zirconiumdichloride,

[8-(2',7'-di-tert-butylfluorene-9'-yl)(2-(1-adamantyl)-8-methyl-3,3b,4,5,6,7,7a,8-octahydrocyclopenta[a]indene)]zirconiumdichloride,

[8-(3',6'-di-tert-butylfluorene-9'-yl)(2-(1-adamantyl)-8-methyl-3,3b,4,5,6,7,7a,8-octahydrocyclopenta[a]indene)]zirconiumdichloride,

[8-(3',6'-di-(1-adamantyl)-fluorene-9'-yl)(2-(1-adamantyl)-8-methyl-3,3b,4,5,6,7,7a,8-octahydrocyclopenta[a]indene)]zirconiumdichloride,

[8-(3',6'-di-tert-butyl-2',7'-dimethylfluorene-9'-yl)(2-(1-adamantyl)-8-methyl-3,3b,4,5,6,7,7a,8-octahydrocyclopenta[a]indene)]zirconiumdichloride,

[8-(octamethylfluorene-12'-yl)(2-(1-adamantyl)-8-methyl-3,3b,4,5,6,7,7a,8-octahydrocyclopenta[a]indene)]zirconiumdichloride,

[8-(hexamethyldicyclopentafluorene-10'-yl)(2-(1-adamantyl)-8-methyl-3,3b,4,5,6,7,7a,8-octahydrocyclopenta[a]indene)]

[8-(fluorene-9'-yl)(2-(1-adamantyl)-8-iso-propyl-3,3b,4,5,6,7,7a,8-octahydrocyclopenta[a]indene)]zirconiumdichloride,

[8-(2',7'-di-tert-butylfluorene-9'-yl)(2-(1-adamantyl)-8-iso-propyl-3,3b,4,5,6,7,7a,8-octahydrocyclopenta[a]indene)]zirconiumdichloride,

[8-(3',6'-di-tert-butylfluorene-9'-yl)(2-(1-adamantyl)-8-iso-propyl-3,3b,4,5,6,7,7a,8-octahydrocyclopenta[a]indene)]zirconiumdichloride,

[8-(3',6'-di-(1-adamantyl)-fluorene-9'-yl)(2-(1-adamantyl)-8-iso-propyl-3,3b,4,5,6,7,7a,8-octahydrocyclopenta[a]indene)]zirconiumdichloride,

[8-(3',6'-di-tert-butyl-2',7'-dimethylfluorene-9'-yl)(2-(1-adamantyl)-8-iso-propyl-3,3b,4,5,6,7,7a,8-octahydrocyclopenta[a]indene)]zirconiumdichloride,

[8-(octamethylfluorene-12'-yl)(2-(1-adamantyl)-8-iso-propyl-3,3b,4,5,6,7,7a,8-octahydrocyclopenta[a]indene)]zirconiumdichloride,

[8-(hexamethyldicyclopentafluorene-10'-yl)(2-(1-adamantyl)-8-iso-propyl-3,3b,4,5,6,7,7a,8-octahydrocyclopenta[a]indene)]zirconiumdichloride,

[7-(fluorene-9'-yl)(2,3,3a,4,7,7a-hexahydro-1H-cyclopenta[a]pentalene)]zirconiumdichloride,

[7-(2',7'-di-tert-butylfluorene-9'-yl)(2,3,3a,4,7,7a-hexahydro-1H-cyclopenta[a]pentalene)]zirconiumdichloride,

[7-(3',6'-di-tert-butylfluorene-9'-yl)(2,3,3a,4,7,7a-hexahydro-1H-cyclopenta[a]pentalene)]zirconiumdichloride,

[7-(3',6'-di-(1-adamantyl)-fluorene-9'-yl)(2,3,3a,4,7,7a-hexahydro-1H-cyclopenta[a]pentalene)]zirconiumdichloride,

[7-(3',6'-di-tert-butyl-2',7'-dimethylfluorene-9'-yl)(2,3,3a,4,7,7a-hexahydro-1H-cyclopenta[a]pentalene)]zirconiumdichloride,

[7-(octamethylfluorene-12'-yl)(2,3,3a,4,7,7a-hexahydro-1H-cyclopenta[a]pentalene)]zirconiumdichloride,

[7-(hexamethyldicyclopentafluorene-10'-yl)(2,3,3a,4,7,7a-hexahydro-1H-cyclopenta[a]pentalene)]zirconiumdichloride,

[7-(fluorene-9'-yl)(5-tert-butyl-7-methyl-2,3,3a,4,7,7a-hexahydro-1H-cyclopenta[a]pentalene)]zirconiumdichloride,

[7-(2',7'-di-tert-butylfluorene-9'-yl)(5-tert-butyl-7-methyl-2,3,3a,4,7,7a-hexahydro-1H-cyclopenta[a]pentalene)]zirconiumdichloride,

[7-(3',6'-di-tert-butylfluorene-9'-yl)(5-tert-butyl-7-methyl-2,3,3a,4,7,7a-hexahydro-1H-cyclopenta[a]pentalene)]zirconiumdichloride,

[7-(3',6'-di-(1-adamantyl)-fluorene-9'-yl)(5-tert-butyl-7-methyl-2,3,3a, 4,7,7a-hexahydro-1H-cyclopenta[a]pentalene)]zirconiumdichloride,

[7-(3',6'-di-tert-butyl-2',7'-dimethylfluorene-9'-yl)(5-tert-butyl-7-methyl-2,3, 3a,4,7,7a-hexahydro-1H-cyclopenta[a]pentalene)]zirconiumdichloride,

[7-(octamethylfluorene-12'-yl)(5-tert-butyl-7-methyl-2,3, 3a,4,7,7a-hexahydro-1H-cyclopenta[a]pentalene)]zirconiumdichloride,

[7-(hexamethyldicyclopentafluorene-10'-yl)(5-tert-butyl-7-methyl-2,3,3a,4,7,7a-hexahydro-H-cyclopenta[a]pentalene)]zirconiumdichloride,

[7-(fluorene-9'-yl)(5-tert-butyl-7-iso-propyl-2,3,3a,4,7,7a-hexahydro-1H-cyclopenta[a]pentalene)]zirconiumdichloride,

[7-(2,7'-di-tert-butylfluorene-9'-yl)(5-tert-butyl-7-iso-propyl-2,3,3a, 4,7,7a-hexahydro-1H-cyclopenta[a]pentalene)]zirconiumdichloride,

[7-(3',6'-di-tert-butylfluorene-9'-yl)(5-tert-butyl-7-iso-propyl-2,3,3a,4,7,7a-hexahydro-H-cyclopenta[a]pentalene)]zirconiumdichloride,

[7-(3',6'-di-(1-adamantyl)-fluorene-9'-yl)(5-tert-butyl-7-iso-propyl-2,3,3a,4,7,7a-hexahydro-1H-cyclopenta[a]pentalene)]zirconiumdichloride,

[7-(3',6'-di-tert-butyl-2',7'-dimethylfluorene-9'-yl)(5-tert-butyl-7-iso-propyl-2,3,3a,4,7,7a-hexahydro-1H-cyclopenta[a]pentalene)]zirconiumdichloride,

[7-(octamethylfluorene-12'-yl)(5-tert-butyl-7-iso-propyl-2,3,3a,4,7,7a-hexahydro-1H-cyclopenta[a]pentalene)]zirconiumdichloride,

[7-(hexamethyldicyclopentafluorene-10'-yl)(5-tert-butyl-7-iso-propyl-2,3,3a,4,7,7a-hexahydro-1H-cyclopenta[a]pentalene)]zirconiumdichloride,

[7-(fluorene-9'-yl)(2-tert-butyl-8-phenyl-2,3,3a,4,7,7a-hexahydro-1H-cyclopenta[a]pentalene)]zirconiumdichloride,

[7-(2',7'-di-tert-butylfluorene-9'-yl)(2-tert-butyl-8-phenyl-2,3,3a,4, 7,7a-hexahydro-1H-cyclopenta[a]pentalene)]zirconiumdichloride,

[7-(3',6'-di-tert-butylfluorene-9'-yl)(2-tert-butyl-8-phenyl-2,3,3a,4,7,7a-hexahydro-1H-cyclopenta[a]pentalene)]zirconiumdichloride,

[7-(3',6'-di-(1-adamantyl)-fluorene-9'-yl)(2-tert-butyl-8-phenyl-2,3,3a,4,7,7a-hexahydro-1H-cyclopenta[a]pentalene)]zirconiumdichloride,

[7-(3',6'-di-tert-butyl-2',7'-dimethylfluorene-9'-yl)(2-tert-butyl-8-phenyl-2,3,3a,4,7,7a-hexahydro-1H-cyclopenta[a]pentalene)]zirconiumdichloride,

[7-(octamethylfluorene-12'-yl)(2-tert-butyl-8-phenyl-2,3,3a,4,7,7a-hexahydro-1H-cyclopenta[a]pentalene)]zirconiumdichloride,

[7-(hexamethyldicyclopentafluorene-10'-yl)(2-tert-butyl-8-phenyl-2,3,3a,4,7,7a-hexahydro-1H-cyclopenta[a]pentalene)]zirconiumdichloride,

[7-(fluorene-9'-yl)(5-tert-butyl-7-cylohexyl-2,3,3a,4,7,7a-hexahydro-1H-cyclopenta[a]pentalene)]zirconiumdichloride,

[7-(2',7'-di-tert-butylfluorene-9'-yl)(5-tert-butyl-7-cylohexyl-2,3,3a,4,7,7a-hexahydro-1H-cyclopenta[a]pentalene)]zirconiumdichloride,

[7-(3',6'-di-tert-butylfluorene-9'-yl)(5-tert-butyl-7-cylohexyl-2,3,3a,4,7,7a-hexahydro-1H-cyclopenta[a]pentalene)]zirconiumdichloride,

[7-(3',6'-di-(1-adamantyl)-fluorene-9'-yl)(5-tert-butyl-7-cylohexyl-2,3,3a,4,7,7a-hexahydro-1H-cyclopenta[a]pentalene)]zirconiumdichloride,

[7-(3',6'-di-tert-butyl-2',7'-dimethylfluorene-9'-yl)(5-tert-butyl-7-cylohexyl-2,3,3a,4,7,7a-hexahydro-1H-cyclopenta[a]pentalene)]zirconiumdichloride,

[7-(octamethylfluorene-12'-yl)(5-tert-butyl-7-cylohexyl-2,3,3a,4,7,7a-hexahydro-1H-cyclopenta[a]pentalene)]zirconiumdichloride,

[7-(hexamethyldicyclopentafluorene-10'-yl)(5-tert-butyl-7-cylohexyl-2,3,3a,4,7,7a-hexahydro-1H-cyclopenta[a]pentaene)]zirconiumdichloride,

[7-(fluorene-9'-yl)(5-adamantane-1-yl-7-methyl-2,3,3a,4,7,7a-hexahydro-1H-cyclopenta[a]pentalene)]zirconiumdichloride,

[7-(2',7'-di-tert-butylfluorene-9'-yl)(5-adamantane-1-yl-7-methyl-2,3,3a,4,7,7a-hexahydro-1H-cyclopenta[a]pentalene)]zirconiumdichloride,

[7-(3',6'-di-tert-butylfluorene-9'-yl)(5-adamantane-1-yl-7-methyl-2,3,3a,4,7,7a-hexahydro-1H-cyclopenta[a]pentalene)]zirconiumdichloride,

[7-(3',6'-di-(1-adamantyl)-fluorene-9'-yl)(5-adamantane-1-yl-7-methyl-2,3,3a,4,7,7a-hexahydro-1H-cyclopenta[a]pentalene)]zirconiumdichloride,

[7-(3',6'-di-tert-butyl-2',7'-dimethylfluorene-9'-yl)(5-adamantane-1-yl-7-methyl-2,3,3a,4,7,7a-hexahydro-1H-cyclopenta[a]pentalene)]zirconiumdichloride,

[7-(octamethylfluorene-12'-yl)(5-adamantane-1-yl-7-methyl-2,3,3a,4,7,7a-hexahydro-1H-cyclopenta[a]pentalene)]zirconiumdichloride,

[7-(hexamethyldicyclopentafluorene-10'-yl)(5-adamantane-1-yl-7-methyl-2,3,3a,4,7,7a-hexahydro-1H-cyclopenta[a]pentalene)]zirconiumdichloride,

[7-(fluorene-9'-yl)(5-adamantane-1-yl-7-iso-propyl-2,3,3a,4,7,7a-hexahydro-1H-cyclopenta[a]pentalene)]zirconiumdichloride,

[7-(2',7'-di-tert-butylfluorene-9'-yl)(5-adamantane-1-yl-7-iso-propyl-2,3,3a,4,7,7a-hexahydro-1H-cyclopenta[a]pentalene)]zirconiumdichloride,

[7-(3',6'-di-tert-butylfluorene-9'-yl)(5-adamantane-1-yl-7-iso-propyl-2,3,3a,4,7,7a-hexahydro-1H-cyclopenta[a]pentalene)]zirconiumdichloride,

[7-(3',6'-di-(1-adamantyl)-fluorene-9'-yl)(5-adamantane-1-yl-7-iso-propyl-2,3,3a,4,7,7a-hexahydro-1H-cyclopenta[a]pentalene)]zirconiumdichloride,

[7-(3',6'-di-tert-butyl-2',7'-dimethylfluorene-9'-yl)(5-adamantane-1-yl-7-iso-propyl-2,3,3a,4,7,7a-hexahydro-1H-cyclopenta[a]pentalene)]zirconiumdichloride,

[7-(octamethylfluorene-12'-yl)(5-adamantane-1-yl-7-iso-propyl-2,3,3a,4,7,7a-hexahydro-1H-cyclopenta[a]pentalene)]zirconiumdichloride, and

[7-(hexamethyldicyclopentafluorene-10'-yl)(5-adamantane-1-yl-7-iso-propyl-2,3,3a,4,7,7a-hexahydro-1H-cyclopenta[a]pentalene)]zirconiumdichloride.

The transition metal compounds (I) of the invention may be titanium derivatives or hafnium derivatives of the above-mentioned compounds. The transition metal compounds [I] of the invention are not limited to the above-mentioned compounds.

The position numbers used in the nomenclature of the above compounds will be explained with reference to Formula [I-1] and Formula [I-2] illustrating exemplary enantiomers of [1-(1',1',4',4',7',7',10',10'-octamethyloctahydrodibenzo[b,h]fluoren-12'-yl)(5-tert-butyl-1-methyl-3-iso-propyl-1,2, 3,4-tetrahydropentalene)]zirconium dichloride and [8-(1',1',4',4',7',7',10',10'-octamethyloctahydrodibenzo[b,h]fluoren-12'-yl)(2-tert-butyl-8-methyl-3,3b,4,5,6,7,7a,8-octahydrocyclopenta[a]indene)]zirconium dichloride, respectively.

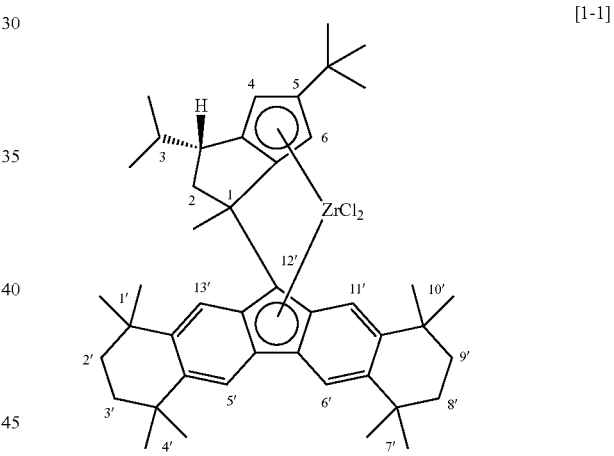

[1-1]

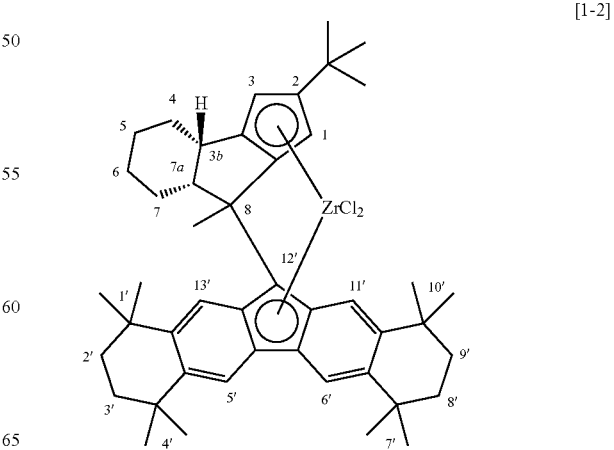

[1-2]

[Processes for Producing Transition Metal Compounds]

The transition metal compounds of the invention may be produced by known processes without limitation. In the following, an example of the processes for producing the inventive transition metal compounds [I] will be described. Enantiomers of the compounds may be produced in the similar manner.

For example, the process for producing the transition metal compound [I] of the invention includes a step (1) of preparing a pentalene compound represented by General Formula (1a). The pentalene compound (1a) may be an appropriate isomer having a steric configuration corresponding to the target transition metal compound [I].

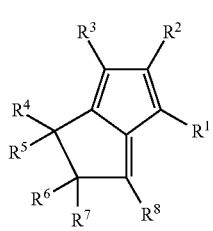

(Ia)

In Formula (1a), $R^1$, $R^3$, $R^5$, $R^6$, $R^7$ and $R^8$ are each independently a hydrogen atom, a hydrocarbon group, a hetero atom-containing hydrocarbon group, or a silicon-containing group; $R^2$ is a hydrocarbon group, a hetero atom-containing hydrocarbon group, or a silicon-containing group; $R^4$ is a hydrogen atom; and any two substituents of the substituents $R^1$ to $R^8$ except $R^4$ may be bonded to each other to form a ring. Preferred embodiments of the configurations are the same as described with respect to General Formula [I].

In an embodiment, the step (1) is followed by a step (2) in which the pentalene compound (1a) is reacted with a fluorene derivative (2a) to form a precursor compound (3a) of a transition metal compound [I], and a step (3) in which a transition metal compound [I] of the invention is obtained from the precursor compound (3a).

⟨ Step (1)⟩

For example, the pentalene compound (1a) may be synthesized by, as illustrated in Reaction [A], reacting a cyclopentadiene derivative (1a-1) with an α,β-unsaturated carbonyl compound (1a-2); or by, as illustrated in Reaction [B], reacting a cyclopentadiene derivative (1a-1) with a carbonyl compound (1a-3) and an aldehyde compound (1a-4).

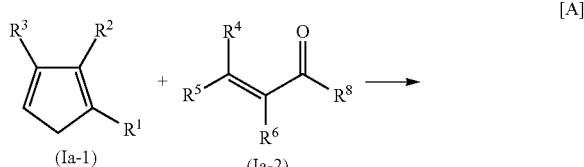

[A]

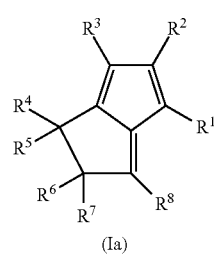

(Ia)

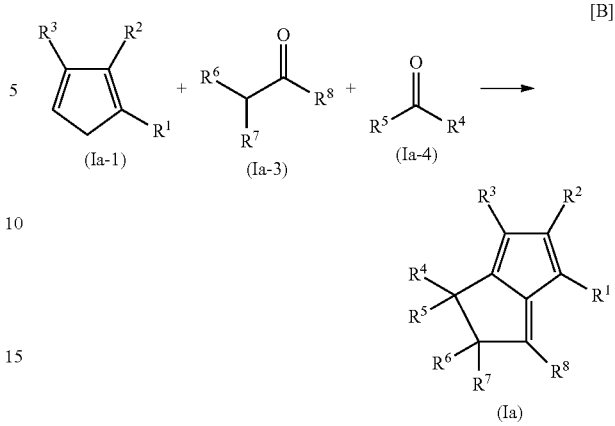

In Reaction [A], $R^1$ to $R^6$ and $R^8$ are as defined in General Formula [I], and $R^7$ is a hydrogen atom. In Reaction [B], $R^1$ to $R^8$ are as defined in General Formula [I]. Preferred embodiments of the configurations are the same as described with respect to General Formula [I]. The raw material compounds may be appropriate isomers having a steric configuration corresponding to the target pentalene compound (1a).

The cyclopentadiene derivative (1a-1), and the fluorene derivative (2a) and the precursor compound (3a) described later have isomeric forms having double bonds at different positions in the cyclopentadienyl ring. The reactions here illustrate only one exemplary form of such isomers. The cyclopentadiene derivative (1a-1), and the fluorene derivative (2a) and the precursor compound (3a) described later may be other isomers having double bonds at different positions in the cyclopentadienyl ring, or may be mixtures of such isomers.

⟨ Reaction [A]⟩

Based on Reaction [A], the pentalene compound (1a) may be produced by reacting a cyclopentadiene derivative (1a-1) with an α,β-unsaturated carbonyl compound (1a-2) under known conditions (see, for example, J. Org. Chem. 1989, 54, 4981-4982).

Alternatively, the pentalene compound (1a) may be produced based on Reaction [A] by a process (process A') in which a cyclopentadiene derivative (1a-1) is treated with a base and is allowed to undergo 1,4-addition to an α,β-unsaturated carbonyl compound (1a-2) to give a ketone or an aldehyde, which is thereafter dehydration condensed.

The base used in the process A' may be a conventional base, with examples including alkali metals such as sodium, potassium and lithium; alkali metal or alkaline earth metal salts such as potassium hydroxide, sodium hydroxide, potassium carbonate, sodium hydrogen carbonate, barium hydroxide, sodium alkoxide, potassium alkoxide, magnesium hydroxide, magnesium alkoxide, potassium hydride and sodium hydride; nitrogen-containing bases such as diethylamine, ammonia, pyrrolidine, piperidine, aniline, methylaniline, triethylamine, lithium diisopropylamide and sodium amide; organic alkali metal compounds such as butyllithium, methyllithium and phenyl lithium; and Grignard reagents such as methylmagnesium chloride, methylmagnesium bromide and phenylmagnesium chloride.

The process A' may involve a catalyst to perform the reaction more efficiently. The catalyst may be a conventional catalyst, with examples including phase transfer catalysts, specifically, crown ethers such as 18-crown-6-ether and 15-crown-5-ether; cryptands; quaternary ammonium salts such as tetrabutylammonium fluoride, methyltrioctylammonium chloride and tricaprylmethylammonium chloride; phosphonium salts such as methyltriphenylphosphonium bromide and tetrabutylphosphonium bromide; and chain polyethers. Examples further include halides of magnesium, calcium, lithium, zinc, aluminum, titanium, iron, zirconium, hafnium, boron, tin and rare earths; Lewis acids such as triflates; and acids such as acetic acid, trifluoroacetic acid, trifluoromethanesulfonic acid and para-tolylsulfonic acid. In the process A', the 1,4-addition reaction may be catalyzed by a copper halide such as copper chloride or copper iodide.

⟨ Reaction [B]⟩

In Reaction [B], a base and/or a catalyst may be added to perform the reaction more efficiently. The bases and the catalysts which may be used in Reaction [B] may be similar to those described in Reaction [A].

In Reaction [B], a cyclopentadiene derivative (1a-1) may be reacted with a carbonyl compound (1a-3) and an aldehyde compound (1a-4) simultaneously, or may be reacted with a carbonyl compound (1a-3) and an aldehyde compound (1a-4) successively in any order. The carbonyl compound (1a-3) or the aldehyde compound (1a-4) may be converted into an enolate with an agent such as lithium propylamide prior to the reaction, or the reaction may involve an enolate corresponding to the carbonyl compound (1a-3) or the aldehyde compound (1a-4) that is synthesized by a known method. Alternatively, the carbonyl compound (1a-3) and the aldehyde compound (1a-4) may be subjected to the reaction under different conditions.

The pentalene compound (1a) may be synthesized by other processes such as those described in Angew. Chem. internal. Edit. 1970, 9, 892-893, J. Am. Chem. SOC. 1985, 107, 5308-5309, and J. Org. Chem. 1990, 55, 4504-4506.

Examples of solvents which may be used in Reactions [A] and [B] include organic solvents, for example, aliphatic hydrocarbons such as pentane, hexane, heptane, cyclohexane and decalin; aromatic hydrocarbons such as benzene, toluene and xylene; ethers such as tetrahydrofuran, diethyl ether, dioxane, 1,2-dimethoxyethane, tert-butyl methyl ether and cyclopentyl methyl ether; halogenated hydrocarbons such as dichloromethane and chloroform; carboxylic acids such as formic acid, acetic acid and trifluoroacetic acid; esters such as ethyl acetate and methyl acetate; amines, nitriles or nitrogen-containing compounds such as triethylamine, pyrrolidine, piperidine, aniline, pyridine and acetonitrile; alcohols such as methanol, ethanol, n-propanol, isopropanol, n-butanol, isopropanol, ethylene glycol and methoxyethanol; amides such as N,N-dimethylformamide, N,N-dimethylacetamide, N,N-dimethylimidazolidinone and N-methylpyrrolidone; dimethyl sulfoxide; sulfur-containing compounds such as carbon disulfide; and ketones such as acetone and methyl ethyl ketone, in particular, aldehyde and ketone used as raw materials; and further include non-organic solvents such as water and ionic liquids. Mixtures of two or more of these solvents are also usable. The reaction temperature in Reactions [A] and [B] is preferably −100 to 150° C., and more preferably −40 to 120° C.

⟨ Step (2)⟩

In an embodiment, the step (1) is followed by a step (2) in which the pentalene compound (1a) is reacted with a fluorene derivative (2a) to form a precursor compound (3a) of a transition metal compound [I].

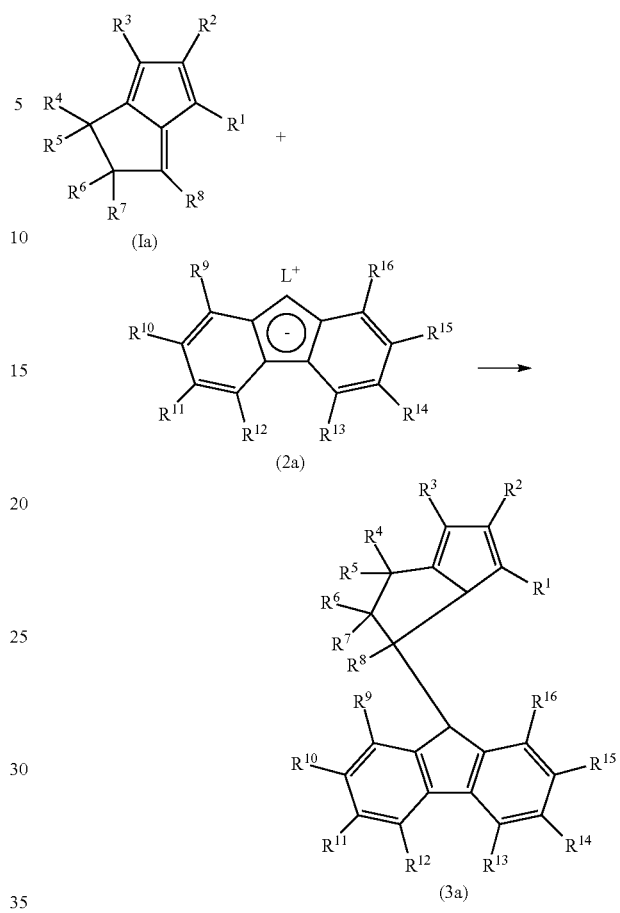

In the above reaction, $R^1$ to $R^{16}$ are as defined in General Formula [I], and L is an alkali metal or an alkaline earth metal. Examples of the alkali metals include lithium, sodium and potassium. Examples of the alkaline earth metals include magnesium and calcium.

The precursor compound (3a) can form a complex in such a manner that the hydrogen atom ($R^4$) bonded to the α-position relative to the cyclopentadiene ring comes on the same side as the central metal due to reasons such as the difference in size between $R^4$ (hydrogen atom) and $R^5$.

The fluorene derivative (2a) may be obtained by a conventional method.

Examples of organic solvents which may be used in the above reaction include aliphatic hydrocarbons such as pentane, hexane, heptane, cyclohexane and decalin; aromatic hydrocarbons such as benzene, toluene and xylene; ethers such as tetrahydrofuran, diethyl ether, dioxane, 1,2-dimethoxyethane, tert-butyl methyl ether and cyclopentyl methyl ether; halogenated hydrocarbons such as dichloromethane and chloroform; and mixtures of two or more of these solvents.

The pentalene compound (1a) and the fluorene derivative (2a) are preferably reacted in a molar ratio of 10:1 to 1:10, more preferably 2:1 to 1:2, and particularly preferably 1.2:1 to 1:1.2. The reaction temperature is preferably −100 to 150° C., and more preferably −40 to 120° C.

⟨ Step (3)⟩

An example will be described below in which a transition metal compound [I] of the invention is produced from the precursor compound (3a). The scope of the invention is not limited to this example, and the transition metal compound [I] of the invention may be produced by any known processes.

⟨Synthesis of Dialkali Metal Salt⟩

The precursor compound (3a) is brought into contact with at least one metal component selected from alkali metals, alkali metal hydrides, alkali metal alkoxides, organic alkali metals and organic alkaline earth metals, in an organic solvent to give a dialkali metal salt.

Examples of the alkali metals for use in the above reaction include lithium, sodium and potassium. Examples of the alkali metal hydrides include sodium hydride and potassium hydride. Examples of the alkali metal alkoxides include sodium methoxide, potassium ethoxide, sodium ethoxide and potassium-tert-butoxide. Examples of the organic alkali metals include methyllithium, butyllithium and phenyllithium. Examples of the organic alkaline earth metals include methylmagnesium halides, butylmagnesium halides and phenylmagnesium halides. Two or more of these metal components may be used in combination.

Examples of the organic solvents for use in the above reaction include aliphatic hydrocarbons such as pentane, hexane, heptane, cyclohexane and decalin; aromatic hydrocarbons such as benzene, toluene and xylene; ethers such as tetrahydrofuran, diethyl ether, dioxane, 1,2-dimethoxyethane, tert-butyl methyl ether and cyclopentyl methyl ether; halogenated hydrocarbons such as dichloromethane and chloroform; and mixtures of two or more of these solvents.

The precursor compound (3a) and the metal component are preferably reacted in a molar ratio (precursor compound (3a):metal component) of 1:1 to 1:20, more preferably 1:1.5 to 1:4, and particularly preferably 1:1.8 to 1:2.5. The reaction temperature is preferably −100 to 200° C., and more preferably −80 to 120° C.

Lewis bases such as tetramethylethylenediamine, and compounds described in WO 2009/072505 such as α-methylstyrene may be used to promote the reaction.

⟨Synthesis of Transition Metal Compound⟩

The dialkali metal salt obtained by the above reaction is reacted with a compound represented by General Formula (4a) in an organic solvent to give a transition metal compound [I] of the present invention.

$$MZ_k \quad (4a)$$

In Formula (4a), M is a Group IV transition metal; Zs are each independently a halogen atom, a hydrocarbon group, an anionic ligand, or a neutral ligand coordinatable with a lone electron pair; and k is an integer of 3 to 6. The atoms, groups and the like represented by M and Z are similar to M and Q, respectively, described in General Formula [I].

Examples of the compounds (4a) include titanium (III or IV) fluoride, chloride, bromide and iodide; zirconium (IV) fluoride, chloride, bromide and iodide; hafnium (IV) fluoride, chloride, bromide and iodide; and complexes of these halides with ethers such as tetrahydrofuran, diethyl ether, dioxane and 1,2-dimethoxyethane.

Examples of the organic solvents used in the above reaction include the organic solvents described in (Synthesis of dialkali metal salt). The dialkali metal salt and the compound (4a) are preferably reacted in a molar ratio of 10:1 to 1:10, more preferably 2:1 to 1:2, and particularly preferably 1.2:1 to 1:1.2. The reaction temperature is preferably −80 to 200° C., and more preferably −75 to 120° C.

⟨Other Processes⟩

In another process, the precursor compound (3a) may be reacted directly with an organometallic reagent such as tetrabenzyltitanium, tetrabenzylzirconium, tetrabenzylhafnium, tetrakis(trimethylsilylmethylene)titanium, tetrakis(trimethylsilylmethylene)zirconium, tetrakis(trimethylsilylmethylene)hafnium, dibenzyldichlorotitanium, dibenzyldichlorozirconium, dibenzyldichlorohafnium, or an amide salt of titanium, zirconium or hafnium.

The transition metal compound [I] obtained by the aforementioned reaction may be isolated and purified by methods such as extraction, recrystallization and sublimation. The transition metal compound [I] of the invention obtained by the aforementioned process may be identified by analytical methods such as proton nuclear magnetic resonance spectrometry, $^{13}C$-nuclear magnetic resonance spectrometry, mass analysis and elemental analysis.

[Olefin Polymerization Catalysts]

The olefin polymerization catalyst of the invention includes at least one transition metal compound selected from the transition metal compounds represented by General Formula [I] and enantiomers thereof (hereinafter, the transition metal compound is also written as the "transition metal compound (A)").

Preferably, the olefin polymerization catalyst of the invention further includes at least one compound (B) selected from organometallic compounds (B-1), organoaluminumoxy compounds (B-2), and compounds (B-3) capable of reacting with the transition metal compound (A) to form an ion pair (hereinafter, the compound is also written as the "compound (B)").

More preferably, the olefin polymerization catalyst of the invention further includes a carrier (C) as required.

The olefin polymerization catalyst of the invention may further include an organic compound component (D) as required.

Hereinbelow, the components other than the transition metal compound (A) will be described in detail.

⟨Compounds (B)⟩

⟨⟨Organometallic Compounds (B-1)⟩⟩

Examples of the organometallic compounds (B-1) include organometallic compounds of Group I, II, XII and XIII metals such as organoaluminum compounds represented by General Formula (B-1a), alkyl complex compounds of Group I metals and aluminum represented by General Formula (B-1b), and dialkyl compounds of Group II or XII metals represented by General Formula (B-1c).

$$Ra_mAl(ORb)_nH_pX_q \quad (B-1a):$$

In Formula (B-1a), Ra and Rb are each independently a hydrocarbon group having 1 to 15, preferably 1 to 4 carbon atoms, X is a halogen atom, $0<m\le3$, $0\le n<3$, $0\le p<3$, $0\le q<3$, and $m+n+p+q=3$. Examples of the organoaluminum compounds (B-1a) include trialkylaluminums such as trimethylaluminum, triethylaluminum and triisobutylaluminum; dialkylaluminum hydrides such as diisobutylaluminum hydride; and tricycloalkylaluminums.

$$M2AlRa_4 \quad (B-1b):$$

In Formula (B-1b), M2 is Li, Na or K, and Ra is a hydrocarbon group having 1 to 15, preferably 1 to 4 carbon atoms. Examples of the alkyl complex compounds (B-1b) include $LiAl(C_2H_5)_4$ and $LiAl(C_7H_{15})_4$.

$$RaRbM3 \quad (B-1c):$$

In Formula (B-1c), Ra and Rb are each independently a hydrocarbon group having 1 to 15, preferably 1 to 4 carbon atoms, and M3 is Mg, Zn or Cd. Examples of the compounds (B-1c) include dimethylmagnesium, diethylmagnesium, di-n-butylmagnesium, ethyl-n-butylmagnesium, diphenylmagnesium, dimethylzinc, diethylzinc, di-n-butylzinc and diphenylzinc.

Of the organometallic compounds (B-1), the organoaluminum compounds (B-1a) are preferred.

The organometallic compounds (B-1) may be used singly, or two or more may be used in combination.

⟪ ⟪ (Organoaluminum-Oxy Compounds (B-2)) ⟫

For example, the organoaluminum-oxy compounds (B-2) may be conventional aluminoxanes, or may be organoaluminum-oxy compounds described in JP-A-H02-78687 which are insoluble or negligibly soluble in benzene. For example, the conventional aluminoxanes may be prepared by the following processes (1) to (4), and are usually obtained as a solution in a hydrocarbon solvent.

(1) An organoaluminum compound such as trialkylaluminum is added to a hydrocarbon medium suspension of a compound containing adsorbed water or a salt containing water of crystallization, for example, magnesium chloride hydrate, copper sulfate hydrate, aluminum sulfate hydrate, nickel sulfate hydrate or cerous chloride hydrate, thereby reacting the organoaluminum compound with the adsorbed water or the water of crystallization.

(2) Water, ice or water vapor is allowed to act directly on an organoaluminum compound such as trialkylaluminum in a medium such as benzene, toluene, diethyl ether or tetrahydrofuran.

(3) An organoaluminum compound such as trialkylaluminum is reacted with an organotin oxide such as dimethyltin oxide or dibutyltin oxide in a medium such as decane, benzene or toluene.

(4) An organoaluminum such as trialkylaluminum is reacted with an organic compound having a carbon-oxygen bond such as a tertiary alcohol, a ketone or a carboxylic acid, and the resultant compound is non-hydrolytically converted by thermal decomposition or the like.

The aluminoxane may contain a small amount of organometallic components. After the solvent or the unreacted organoaluminum compound is removed by distillation from the recovered solution of the aluminoxane, the residue may be redissolved in a solvent or suspended in a poor solvent for the aluminoxane.

Specific examples of the organoaluminum compounds used in preparing the aluminoxanes include the organoaluminum compounds mentioned above as the organoaluminum compounds (B-1a). Of those compounds, trialkylaluminums and tricycloalkylaluminums are preferred, and trimethylaluminum is particularly preferred.

Examples of the organoaluminum-oxy compounds (B-2) further include modified methylaluminoxanes. The modified methylaluminoxanes are aluminoxanes prepared from trimethylaluminum and an alkylaluminum other than trimethylaluminum. Such compounds are generally called MMAOs. The MMAOs may be prepared by methods described in U.S. Pat. No. 4,960,878 and U.S. Pat. No. 5,041,584. Further, aluminoxanes in which R is an isobutyl group are commercially produced from trimethylaluminum and triisobutylaluminum by manufacturers such as Toso Finechem Corporation, the compounds being sold under the trade names of MMAO and TMAO.

These MMAOs are aluminoxanes that are improved in solubility in solvents and in storage stability. Specifically, such aluminoxanes are characterized in that they are dissolved in aliphatic hydrocarbons or alicyclic hydrocarbons in contrast to the aforementioned aluminoxanes which are insoluble or negligibly soluble in benzene.

Examples of the organoaluminum-oxy compounds (B-2) further include boron-containing organoaluminum-oxy compounds, halogen-containing aluminoxanes described in WO 2005/066191 and WO 2007/131010, and ionic aluminoxanes described in WO 2003/082879.

The compounds (B-2) may be used singly, or two or more may be used in combination.

⟪ ⟪ Compounds (B-3) Capable of Reacting with Transition Metal Compound (A) to Form Ion Pair⟫ ⟫

Examples of the compounds (B-3) capable of reacting with the transition metal compound (A) to form an ion pair (hereinafter, also written as "ionic compounds (B-3)") include Lewis acids, ionic compounds, borane compounds and carborane compounds described in, for example, JP-A-H01-501950, JP-A-H01-502036, JP-A-H03-179005, JP-A-H03-179006, JP-A-H03-207703, JP-A-H03-207704 and U.S. Pat. No. 5,321,106. Examples further include heteropoly compounds and isopoly compounds.

Preferred ionic compounds (B-3) are compounds represented by General Formula (B-3a).

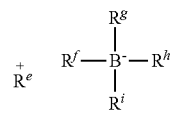

(8-3a)

Examples of $R^{e+}$ in Formula (B-3a) include $H^+$, carbenium cations, oxonium cations, ammonium cations, phosphonium cations, cycloheptyltrienyl cations and ferrocenium cations having transition metals. $R^f$ to $R^i$ are each independently an organic group, and preferably an aryl group.

Examples of the carbenium cations include trisubstituted carbenium cations such as triphenylcarbenium cation, tris(methylphenyl)carbenium cation and tris(dimethylphenyl)carbenium cation.

Examples of the ammonium cations include trialkylammonium cations such as trimethylammonium cation, triethylammonium cation, tri(n-propyl)ammonium cation, triisopropylammonium cation, tri(n-butyl)ammonium cation and triisobutylammonium cation; N,N-dialkylanilinium cations such as N,N-dimethylanilinium cation, N,N-diethylanilinium cation and N,N-2,4,6-pentamethylanilinium cation; and dialkylammonium cations such as diisopropylammonium cation and dicyclohexylammonium cation.

Examples of the phosphonium cations include triarylphosphonium cations such as triphenylphosphonium cation, tris(methylphenyl)phosphonium cation and tris(dimethylphenyl)phosphonium cation.

For example, $R^{e+}$ is preferably a carbenium cation or an ammonium cation, and particularly preferably triphenylcarbenium cation, N,N-dimethylanilinium cation or N,N-diethylanilinium cation.

Examples of the carbenium salts include triphenylcarbenium tetraphenylborate, triphenylcarbenium tetrakis(pentafluorophenyl)borate, triphenylcarbenium tetrakis(3,5-ditrifluoromethylphenyl)borate, tris(4-methylphenyl)carbenium tetrakis(pentafluorophenyl)borate and tris(3,5-dimethylphenyl)carbenium tetrakis(pentafluorophenyl)borate.

Examples of the ammonium salts include trialkyl-substituted ammonium salts, N,N-dialkylanilinium salts and dialkylammonium salts.

Examples of the trialkyl-substituted ammonium salts include triethylammonium tetraphenylborate, tripropylammonium tetraphenylborate, tri(n-butyl)ammonium tetraphenylborate, trimethylammonium tetrakis(p-tolyl)borate, trimethylammonium tetrakis(o-tolyl)borate, tri(n-butyl)

ammonium tetrakis(pentafluorophenyl)borate, triethylammonium tetrakis(pentafluorophenyl)borate, tripropylammonium tetrakis(pentafluorophenyl)borate, tripropylammonium tetrakis(2,4-dimethylphenyl)borate, tri(n-butyl)ammonium tetrakis(3,5-dimethylphenyl)borate, tri(n-butyl)ammonium tetrakis(4-trifluoromethylphenyl)borate, tri(n-butyl)ammonium tetrakis(3,5-ditrifluoromethylphenyl)borate, tri(n-butyl)ammonium tetrakis(o-tolyl)borate, dioctadecylmethylammonium tetraphenylborate, dioctadecylmethylammonium tetrakis(p-tolyl)borate, dioctadecylmethylammonium tetrakis(o-tolyl)borate, dioctadecylmethylammonium tetrakis(pentafluorophenyl)borate, dioctadecylmethylammonium tetrakis(2,4-dimethylphenyl)borate, dioctadecylmethylammonium tetrakis(3,5-dimethylphenyl)borate, dioctadecylmethylammonium tetrakis(4-trifluoromethylphenyl)borate, dioctadecylmethylammonium tetrakis(3,5-ditrifluoromethylphenyl)borate, and dioctadecylmethylammonium.

Examples of the N,N-dialkylanilinium salts include N,N-dimethylanilinium tetraphenylborate, N,N-dimethylanilinium tetrakis(pentafluorophenyl)borate, N,N-dimethylanilinium tetrakis(3,5-ditrifluoromethylphenyl)borate, N,N-diethylanilinium tetraphenylborate, N,N-diethylanilinium tetrakis(pentafluorophenyl)borate, N,N-diethylanilinium tetrakis(3,5-ditrifluoromethylphenyl)borate, N,N-2,4,6-pentamethylanilinium tetraphenylborate, and N,N-2,4,6-pentamethylanilinium tetrakis(pentafluorophenyl)borate.

Examples of the dialkylammonium salts include di(1-propyl)ammonium tetrakis(pentafluorophenyl)borate, and dicyclohexylammonium tetraphenylborate.

Further, ionic compounds disclosed by the present applicant (for example, JP-A-2004-51676) may also be used as the ionic compounds (B-2) without limitation.

The ionic compounds (B-2) may be used singly, or two or more may be used in combination.

⟨Carriers (C)⟩

Examples of the carriers (C) include inorganic or organic compounds in the form of granular or fine particulate solid. It is preferable to use the transition metal compound (A) supported on the carrier (C).

⟨⟨Inorganic Compounds⟩⟩

Preferred inorganic compounds as the carriers (C) are porous oxides, inorganic chlorides, clays, clay minerals and ion-exchangeable layered compounds.

Examples of the porous oxides include oxides such as $SiO_2$, $Al_2O_3$, $MgO$, $ZrO_2$, $TiO_2$, $B_2O_3$, $CaO$, $ZnO$, $BaO$ and $ThO_2$, and complexes and mixtures containing these oxides. For example, natural or synthetic zeolites, $SiO_2$—$MgO$, $SiO_2$—$Al_2O_3$, $SiO_2$—$TiO_2$, $SiO_2$—$V_2O_5$, $SiO_2$—$Cr_2O_3$ and $SiO_2$—$TiO_2$—$MgO$ may be used. Of these, porous oxides containing $SiO_2$ and/or $Al_2O_3$ as a main component are preferable.

The porous oxides have different properties depending on types and production processes. The carriers that are preferably used in the invention preferably have a particle diameter of 1 to 300 μm, more preferably 3 to 100 μm; a specific surface area of 50 to 1300 m²/g, more preferably 200 to 1200 m²/g; and a pore volume of 0.3 to 3.0 cm³/g, more preferably 0.5 to 2.0 cm³/g. Where necessary, the carriers may be used after being dried and/or calcined at 100 to 1000° C., preferably 150 to 700° C. The shapes of the particles are not particularly limited, but spherical particles are particularly preferable.

Examples of the inorganic chlorides include $MgCl_2$, $MgBr_2$, $MnCl_2$ and $MnBr_2$. The inorganic chlorides may be used as such or may be used after being crushed with a ball mill or an oscillating mill. Further, the inorganic chlorides may be dissolved in solvents such as alcohols and be precipitated as fine particles with precipitating agents.

The clays are usually composed of clay minerals as main components. The ion-exchangeable layered-compounds are compounds having a crystal structure in which planes formed by bonds such as ionic bonds are stacked in parallel on top of one another with a weak bond strength, and in which the ions contained therein are exchangeable. Most clay minerals are ion-exchangeable layered compounds. The clays, the clay minerals and the ion-exchangeable layered compounds are not limited to natural products but may be synthetic products. Examples of such clays, clay minerals and ion-exchangeable layered compounds include clays, clay minerals and ion crystalline compounds having layered crystal structures such as hexagonal closest packed structures, antimony structures, $CdCl_2$ structures and $CdI_2$ structures.

Examples of the clays and the clay minerals include kaolin, bentonite, kibushi clay, gairome clay, allophane, hisingerite, pyrophyllite, mica, montmorillonite, vermiculite, chlorite, palygorskite, kaolinite, nacrite, dickite, halloysite, pectolite and taeniolite.

Examples of the ion-exchangeable layered compounds include crystalline acid salts of polyvalent metals such as $\alpha\text{-Zr}(HAsO_4)_2 \cdot H_2O$, $\alpha\text{-Zr}(HPO_4)_2$, $\alpha\text{-Zr}(KPO_4)_2 \cdot 3H_2O$, $\alpha\text{-Ti}(HPO_4)_2$, $\alpha\text{-Ti}(HAsO_4)_2 \cdot H_2O$, $\alpha\text{-Sn}(HPO_4)_2 \cdot H_2O$, $\gamma\text{-Zr}(HPO_4)_2$, $\gamma\text{-Ti}(HPO_4)_2$ and $\gamma\text{-Ti}(NH_4PO_4)_2 \cdot H_2O$.

It is also preferable that the clays and the clay minerals be subjected to chemical treatments. Any chemical treatments may be used, with examples including a surface treatment to remove impurities on the surface and a treatment to modify the crystal structure of the clay. Specific examples of the chemical treatments include acid treatments, alkali treatments, salt treatments and organic treatments.

Utilizing the ion exchange properties, the spaces between the layers in the ion-exchangeable layered compounds may be enlarged by exchanging the exchangeable ions between the layers with other larger and bulkier ions. Such bulky ions serve as columns to support the layered structures and are generally called pillars. The introduction of other substances between layers of layered compounds is called intercalation.

Examples of the guest compounds to be intercalated include cationic inorganic compounds such as $TiCl_4$ and $ZrCl_4$; metal alkoxides such as $Ti(OR)_4$, $Zr(OR)_4$, $PO(OR)_3$ and $B(OR)_3$ (R is a hydrocarbon group or the like); and metal hydroxide ions such as $[Al_{13}O_4(OH)_{24}]^{7+}$, $[Zr_4(OH)_{14}]^{2+}$ and $[Fe_3O(OCOCH_3)_6]^+$. These compounds may be used singly, or two or more may be used in combination. The intercalation of the above compounds may be carried out in the presence of polymers obtained by hydrolysis of metal alkoxides such as $Si(OR)_4$, $Al(OR)_3$ and $Ge(OR)_4$ (R is a hydrocarbon group or the like) or in the presence of colloidal inorganic compounds such as $SiO_2$.

Examples of the pillars include oxides produced by intercalation of the above metal hydroxide ions between layers followed by thermal dehydration.

Of the carriers (C), porous oxides containing $SiO_2$ and/or $Al_2O_3$ as a main component are preferable. The clays and the clay minerals are also preferable, and montmorillonite, vermiculite, pectolite, taeniolite and synthetic mica are particularly preferable.

⟨⟨Organic Compounds⟩⟩

Examples of the organic compounds as the carriers (C) include granular or fine particulate solids having a particle diameter in the range of 5 to 300 μm. Specific examples include (co)polymers produced from an α-olefin having 2 to 14 carbon atoms such as ethylene, propylene, 1-butene or 4-methyl-1-pentene as a main component; (co)polymers produced from vinylcyclohexane or styrene as a main component; and modified products of these polymers.

⟨Organic Compound Components (D)⟩

In the invention, the organic compound component (D) is used as required to improve polymerization performance and to enhance properties of the obtainable polymers. Examples of the organic compounds (D) include alcohols, phenolic compounds, carboxylic acids, phosphorus compounds, amides, polyethers and sulfonate salts.

⟨Use and Sequence of Addition of Components⟩

In the olefin polymerization, the components may be used and added in appropriately selected manners and orders. For example, the components may be used and added as described below. In the following, the transition metal compound (A), the compound (B), the carrier (C) and the organic compound component (D) are also written as "components (A) to (D)".

(1) The component (A) alone is added to a polymerization reactor.

(2) The component (A) and the component (B) are added to a polymerization reactor in any order.

(3) A catalyst component in which the component (A) is supported on the component (C), and the component (B) are added to a polymerization reactor in any order.

(4) A catalyst component in which the component (B) is supported on the component (C), and the component (A) are added to a polymerization reactor in any order.

(5) A catalyst component in which the component (A) and the component (B) are supported on the component (C) is added to a polymerization reactor.

In the methods (2) to (5), two or more of the catalyst components may be brought into contact with each other beforehand. In the methods (4) and (5) in which the component (B) is supported, an unsupported component (B) may be added in any order as required. In this case, the components (B) may be the same as or different from each other. Further, an olefin may be prepolymerized on the solid catalyst component in which the component (A) is supported on the component (C), and the solid catalyst component in which the component (A) and the component (B) are supported on the component (C). Furthermore, an additional catalyst component may be supported on the prepolymerized solid catalyst component.

[Olefin Polymer Production Processes]

The olefin polymer production process of the present invention includes a step of polymerizing one, or two or more olefins in the presence of the inventive olefin polymerization catalyst. Here, the term "polymerization" is used as a collective term including homopolymerization and copolymerization. Further, the meaning of the phrase "olefins are polymerized in the presence of the olefin polymerization catalyst" includes embodiments in which olefins are polymerized while the components of the olefin polymerization catalyst are added to the polymerization reactor in an appropriate manner as described in the methods (1) to (5) above.

Preferably, propylene and optionally at least one olefin A selected from ethylene and α-olefins having 4 to 30 carbon atoms are polymerized in the presence of the inventive olefin polymerization catalyst to produce an olefin polymer including propylene-derived structural units in the range of 50 to 100 mol %, preferably 55 to 100 mol %, more preferably 80 to 100 mol %, and particularly preferably 90 to 100 mol % (wherein the total of the content of structural units derived from propylene and the content of structural units derived from the olefin(s) A is 100 mol %).

In the invention, the polymerization may be carried out by any of liquid-phase polymerization methods such as solution polymerization and suspension polymerization, and gas-phase polymerization methods. Examples of inert hydrocarbon solvents used in the liquid-phase polymerization methods include aliphatic hydrocarbons such as propane, butane, pentane, hexane, heptane, octane, decane, dodecane and kerosine; alicyclic hydrocarbons such as cyclopentane, cyclohexane and methylcyclopentane; aromatic hydrocarbons such as benzene, toluene and xylene; and halogenated hydrocarbons such as ethylene chloride, chlorobenzene and dichloromethane. The inert hydrocarbon solvents may be used singly, or two or more may be used in combination. A so-called bulk polymerization method may be used in which the liquefied olefin supplied to the polymerization itself is used as the solvent.

In the polymerization of olefins using the olefin polymerization catalyst of the invention, the components that form the olefin polymerization catalyst may be used in the following amounts. In the olefin polymerization catalyst of the invention, the contents of the components may be controlled as described below.

The component (A) is usually used in an amount of $10^{-10}$ to $10^{-2}$ mol, and preferably $10^{-8}$ to $10^{-3}$ mol per liter of the reaction volume. The component (B-1) may be used in such an amount that the molar ratio [(B-1)/M] of the component (B-1) to all the transition metal atoms (M) in the component (A) is usually 1 to 50,000, preferably 10 to 20,000, and particularly preferably 50 to 10,000. The component (B-2) may be used in such an amount that the molar ratio [Al/M] of the aluminum atoms in the component (B-2) to all the transition metal atoms (M) in the component (A) is usually 10 to 5,000, and preferably 20 to 2,000. The component (B-3) may be used in such an amount that the molar ratio [(B-3)/M] of the component (B-3) to all the transition metal atoms (M) in the component (A) is usually 1 to 1000, and preferably 1 to 200.

When the component (C) is used, the amount thereof may be preferably such that the weight ratio [(A)/(C)] of the component (A) to the component (C) is 0.0001 to 1, more preferably 0.0005 to 0.5, and still more preferably 0.001 to 0.1.

When the component (D) is used, the amount thereof may be such that, when the component (B) is the component (B-1), the molar ratio [(D)/(B-1)] is usually 0.01 to 10, and preferably 0.1 to 5; when the component (B) is the component (B-2), the molar ratio [(D)/(B-2)] is usually 0.005 to 2, and preferably 0.01 to 1; and when the component (B) is the component (B-3), the molar ratio [(D)/(B-3)] is usually 0.01 to 10, and preferably 0.1 to 5.

In the production process of the invention, the olefin polymerization temperature is usually −50 to +200° C., and preferably 0 to 180° C.; and the polymerization pressure is usually atmospheric pressure to 10 MPaG, and preferably atmospheric pressure to 5 MPaG. The polymerization reaction may be carried out batchwise, semi-continuously or continuously. The polymerization may be carried out in two or more stages under different reaction conditions. The molecular weight of the obtainable olefin polymers may be adjusted by hydrogen and so on in the polymerization system, by controlling the polymerization temperature, or by controlling the amount of the component (B) used.

The production process of the invention can produce olefin polymers such as propylene polymers which have high stereoregularity and high molecular weight and which may be easily crystallized into a β-phase, in such a manner that high catalytic activity is maintained even under industrially advantageous high-temperature conditions. Under such high-temperature conditions, the polymerization temperature is usually 40° C. or above, preferably 40 to 200° C., more preferably 45 to 150° C., and particularly preferably 50 to 150° C. (In other words, the polymerization temperature is particularly preferably a temperature at which industrial production is feasible.)

In particular, hydrogen is a preferred additive which may enhance the polymerization activity of the catalyst and may increase or decrease the molecular weight of polymers. When hydrogen is added to the system, the amount thereof is appropriately about 0.00001 to 100 NL per 1 mol of the olefin. The hydrogen concentration in the system may be controlled by adjusting the amount of hydrogen supplied, or also by performing a reaction in the system which generates or consumes hydrogen, by separating hydrogen with use of a membrane, or by discharging part of the gas containing hydrogen out of the system.

Olefin polymers synthesized by the inventive production process may be subjected to known post treatment steps such as catalyst deactivation step, residual catalyst removal step and drying step as required.

⟨ Olefins⟩

The olefin supplied to the polymerization reaction in the inventive production process is preferably propylene. Where necessary, at least one olefin A selected from ethylene and α-olefins having 4 to 30 carbon atoms may be used in combination with propylene.

The olefin A which may be used together with propylene is more preferably at least one selected from ethylene and α-olefins having 4 to 20 carbon atoms, and is particularly preferably at least one selected from ethylene and α-olefins having 4 to 10 carbon atoms.

Examples of the α-olefins include linear or branched α-olefins. Examples of the linear or branched α-olefins include 1-butene, 2-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene and 1-eicosene.

The polymerization may be performed in the presence of at least one selected from cyclic olefins, polar group-containing olefins, hydroxyl-terminated vinyl compounds and aromatic vinyl compounds in the reaction system. Further, the polymerization may involve polyenes. Additional monomers such as vinylcyclohexane may be copolymerized without departing from the spirit of the invention.

Examples of the cyclic olefins include cyclopentene, cycloheptene, norbornene, 5-methyl-2-norbornene, tetracyclododecene and 2-methyl-1,4,5,8-dimethano-1,2,3,4,4a,5,8,8a-octahydronaphthalene.

Examples of the polar group-containing olefins include α,β-unsaturated carboxylic acids such as acrylic acid, methacrylic acid, fumaric acid, maleic anhydride, itaconic acid, itaconic anhydride and bicyclo(2,2,1)-5-heptene-2,3-dicarboxylic anhydride, and metal salts thereof such as sodium salts, potassium salts, lithium salts, zinc salts, magnesium salts, calcium salts and aluminum salts;

α,β-unsaturated carboxylate esters such as methyl acrylate, ethyl acrylate, n-propyl acrylate, isopropyl acrylate, n-butyl acrylate, isobutyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate;

vinyl esters such as vinyl acetate, vinyl propionate, vinyl caproate, vinyl caprate, vinyl laurate, vinyl stearate and vinyl trifluoroacetate; and unsaturated glycidyls such as glycidyl acrylate, glycidyl methacrylate and itaconic acid monoglycidyl ester.

Examples of the hydroxyl-terminated vinyl compounds include linear hydroxyl-terminated vinyl compounds such as hydroxylated-1-butene, hydroxylated-1-pentene, hydroxylated-1-hexene, hydroxylated-1-octene, hydroxylated-1-decene, hydroxylated-1-undecene, hydroxylated-1-dodecene, hydroxylated-1-tetradecene, hydroxylated-1-hexadecene, hydroxylated-1-octadecene and hydroxylated-1-eicosene; and branched hydroxyl-terminated vinyl compounds such as hydroxylated-3-methyl-1-butene, hydroxylated-3-methyl-1-pentene, hydroxylated-4-methyl-1-pentene, hydroxylated-3-ethyl-1-pentene, hydroxylated-4,4-dimethyl-1-pentene, hydroxylated-4-methyl-1-hexene, hydroxylated-4,4-dimethyl-1-hexene, hydroxylated-4-ethyl-1-hexene and hydroxylated-3-ethyl-1-hexene.

Examples of the aromatic vinyl compounds include styrene; mono- or polyalkylstyrenes such as o-methylstyrene, m-methylstyrene, p-methylstyrene, o,p-dimethylstyrene, o-ethylstyrene, m-ethylstyrene and p-ethylstyrene; functional group-containing styrene derivatives such as methoxystyrene, ethoxystyrene, vinylbenzoic acid, methyl vinylbenzoate, vinyl benzyl acetate, hydroxystyrene, o-chlorostyrene, p-chlorostyrene and divinylbenzene; 3-phenylpropylene, 4-phenylpropylene and a-methylstyrene.

The polyenes are preferably selected from dienes and trienes. In a preferred embodiment, the polyene is used in the range of 0.0001 to 1 mol % relative to all the olefins supplied to the polymerization reaction.

Examples of the dienes include α,ω-nonconjugated dienes such as 1,4-pentadiene, 1,5-hexadiene, 1,4-hexadiene, 1,4-octadiene, 1,5-octadiene, 1,6-octadiene, 1,7-octadiene and 1,9-decadiene; nonconjugated dienes such as ethylidenenorbornene, vinylnorbornene, dicyclopentadiene, 7-methyl-1,6-octadiene and 4-ethylidene-8-methyl-1,7-nonadiene; and conjugated dienes such as butadiene and isoprene. Of these, the α,ω-nonconjugated dienes and dienes having a norbornene skeleton are preferred.

Examples of the trienes include nonconjugated trienes such as 6,10-dimethyl-1,5,9-undecatriene, 4,8-dimethyl-1,4,8-decatriene, 5,9-dimethyl-1,4,8-decatriene, 6,9-dimethyl-1,5,8-decatriene, 6,8,9-trimethyl-1,5,8-decatriene, 6-ethyl-10-methyl-1,5,9-undecatriene, 4-ethylidene-1,6-octadiene, 7-methyl-4-ethylidene-1,6-octadiene, 4-ethylidene-8-methyl-1,7-nonadiene (EMND), 7-methyl-4-ethylidene-1,6-nonadiene, 7-ethyl-4-ethylidene-1,6-nonadiene, 6,7-dimethyl-4-ethylidene-1,6-octadiene, 6,7-dimethyl-4-ethylidene-1,6-nonadiene, 4-ethylidene-1, 6-decadiene, 7-methyl-4-ethylidene-1,6-decadiene, 7-methyl-6-propyl-4-ethylidene-1,6-octadiene, 4-ethylidene-1,7-nonadiene, 8-methyl-4-ethylidene-1,7-nonadiene and 4-ethylidene-1,7-undecanediene; and conjugated trienes such as 1,3,5-hexatriene. Of these, nonconjugated trienes having a double bond at an end, 4,8-dimethyl-1,4,8-decatriene and 4-ethylidene-8-methyl-1,7-nonadiene (EMND) are preferable.

The dienes or trienes may be used singly, or two or more may be used in combination. Further, the dienes and the trienes may be used in combination. Of the polyenes, the α,ω-nonconjugated dienes and the polyenes having a norbornene skeleton are preferred.

It is more preferable that at least one olefin A used together with propylene be at least one selected from ethylene, 1-butene, 1-hexene, 4-methyl-1-pentene and 1-octene. Still more preferably, at least one olefin A is ethylene. The most preferred copolymerization is the copolymerization of propylene with ethylene.

Propylene and at least one optional olefin A selected from ethylene and α-olefins having 4 to 30 carbon atoms are used in such amounts that the propylene:olefin(s) A ratio (by mol) is usually 1:10 to 5000:1, and preferably 1:5 to 1000:1.

[Olefin Polymers]

The olefin polymers of the invention may be obtained by polymerizing one, or two or more olefins in the presence of the aforementioned olefin polymerization catalyst of the invention. Preferably, the olefin polymers may be obtained by polymerizing propylene and optionally at least one olefin A selected from ethylene and α-olefins having 4 to 30 carbon atoms.

In an embodiment, the olefin polymer of the invention is a propylene polymer containing propylene-derived structural units in the range of 50 to 100 mol %, preferably 55 to 100 mol %, more preferably 80 to 100 mol %, and particularly preferably 90 to 100 mol %. The propylene polymer contains structural units derived from the olefin(s) A except propylene in the total content of 0 to 50 mol %, preferably 0 to 45 mol %, more preferably 0 to 20 mol %, and particularly preferably 0 to 10 mol %. Here, the total of the content of structural units derived from propylene and the content of structural units derived from the olefin(s) A is 100 mol %. The polymers may contain other structural units without departing from the spirit of the invention. The contents of these units may be determined by nuclear magnetic resonance spectroscopy or, in the case where there is a reference substance, by a method such as infrared spectroscopy.

Particularly preferred polymers are propylene homopolymers, propylene/ethylene copolymers, propylene/1-butene copolymers, propylene/ethylene/l-butene copolymers, propylene/1-octene polymers, propylene/1-hexene polymers, propylene/4-methyl-1-pentene polymers, propylene/ethylene/1-octene polymers, propylene/ethylene/1-hexene polymers and propylene/ethylene/4-methyl-1-pentene polymers. The polymers may be impact copolymers obtained by mixing or continuously producing two or more of these polymers.

Of the olefin polymers of the invention having the structural units described above, the most preferred polymers are propylene polymers substantially consisting of propylene-derived structural units, and propylene/ethylene copolymers substantially consisting of propylene-derived structural units and ethylene-derived structural units. The term "substantially" means that the propylene polymers contain 95 wt % or more of propylene-derived structural units and the propylene/ethylene copolymers contain propylene-derived structural units and ethylene-derived structural units in a total amount of 95 wt % or more.

In the olefin polymers of the invention, the weight-average molecular weight measured by gel permeation chromatography (GPC) is preferably 10,000 to 1,000,000, more preferably 80,000 to 500,000, and particularly preferably 90,000 to 400,000. The ratio of the weight-average molecular weight (Mw) to the number-average molecular weight (Mn), namely, the molecular weight distribution (Mw/Mn) is preferably 1.0 to 8.0, more preferably 1.5 to 5.0, and particularly preferably 1.8 to 3.5.

In the olefin polymer of the invention, the intrinsic viscosity [η] is preferably 0.1 to 12 dl/g, more preferably 0.5 to 10 dl/g, and more preferably 0.7 to 8 dl/g.

In the olefin polymer of the invention, the stereoregularity of the propylene-derived structural units is preferably isotactic. More preferably, the meso pentad fraction (mmmm) measured by $^{13}$C-NMR is not less than 70%, still more preferably not less than 80%, further preferably not less than 90%, and particularly preferably not less than 97%.

In the olefin polymer of the invention, the proportion of regioerrors due to 2,1-insertions of propylene monomers (hereinafter, also written as "2,1-insertion fraction"), and the proportion of regioerrors due to 1,3-insertions (hereinafter, also written as "1,3-insertion fraction") in all the propylene structural units measured by $^{13}$C-NMR spectroscopy are each preferably not more than 0.5 mol %, more preferably not more than 0.2 mol %, and particularly preferably not more than 0.1 mol %.

Details of the measurements of these properties are described in Examples.

With the aforementioned configurations and properties, the olefin polymers of the invention exhibit high heat resistance and high mechanical properties such as high rigidity and high strength.

[Propylene Polymers]

The novel propylene polymer of the invention preferably has a meso pentad fraction (mmmm) measured by $^{13}$C-NMR of 97.0% to 99.5%, more preferably 97.5% to 99.5%, and particularly preferably 97.5% to 99.0%. Any mmmm that is below the lower limit may result in insufficient heat resistance and rigidity. If the mmmm exceeds the upper limit, problems may be encountered such as difficult formation of a β-phase during crystallization, and poor process-ability.

In the propylene polymer of the invention, the total of the proportion of regioerrors due to 2,1-insertions of propylene monomers (hereinafter, also written as "2,1-insertion fraction"), and the proportion of regioerrors due to 1,3-insertions (hereinafter, also written as "1,3-insertion fraction") in all the propylene structural units measured by $^{13}$C-NMR spectroscopy is preferably 0.01 mol % to 0.06 mol %, and more preferably 0.01 mol % to 0.05 mol %. As long as the total of the 2,1-insertion fraction and the 1,3-insertion fraction is in the above range, any of the 2,1-insertion fraction and the 1,3-insertion fraction may be substantially below the detection limit, namely, less than 0.01 mol %. If the total of the 2,1-insertion fraction and the 1,3-insertion fraction is less than the lower limit or exceeds the upper limit, problems may be encountered such as difficult formation of a β-phase during crystallization, poor process-ability, and decreases in heat resistance and rigidity.

The melting point of the inventive propylene polymer may be measured by differential scanning calorimetry (DSC). In general, the measurement of the melting point of a highly stereoregular polypropylene by DSC under conditions described in, for example, JIS K7121, gives a single peak assigned to an α-phase. While a large number of melting peaks are observed at times in the case of, for example, a polypropylene having low stereoregularity, a polypropylene containing a large proportion of regioerrors, or a polypropylene having an extremely low-molecular weight, it is known that Ziegler-Natta-catalyzed stereoregular polypropylenes having mmmm of 95% or more show a single peak that is observed (see Polymer, 1993, Volume 34, Number 19, pp. 4083 to 4088).

In a preferred embodiment, the propylene polymer of the invention has the specific stereoregularity (mmmm) and the specific proportion of regioerrors (the total of the 2,1-insertion fraction and the 1,3-insertion fraction). Consequently, in spite of the fact that the polymer has very high stereoregularity, the polymer is free from special structures such as branched structures and exhibits a melting peak assigned to a β-phase in addition to the melting peak assigned to an α-phase. Specifically, the propylene polymer according to a preferred embodiment of the invention shows one or more melting peaks assigned to α-phases in the range of 160° C. and above, preferably 160° C. to 190° C., more preferably 160° C. to 175° C., and particularly preferably 160° C. to 170° C., and also shows one or more melting peaks assigned to β-phases in the range of 140° C. to less than 160° C.

The novel propylene polymer of the invention preferably has a weight-average molecular weight (Mw), a molecular weight distribution (Mw/Mn) and an intrinsic viscosity [η] in the ranges described in [Olefin polymers].

Details of the measurements of these properties are described in Examples.

The novel propylene polymers of the invention substantially consist of propylene-derived structural units, but may include comonomer-derived structural units without departing from the spirit of the invention. The term "substantially" means that the propylene polymers contain 95 wt % or more of propylene-derived structural units. Examples of the comonomers include the olefins described in [Olefin polymer production processes].

For example, the propylene polymers having the aforementioned configurations and properties may be obtained by polymerizing propylene and optionally a comonomer (for example, at least one olefin A selected from ethylene and α-olefins having 4 to 30 carbon atoms) in the presence of the inventive olefin polymerization catalyst described hereinabove. Detailed polymerization conditions are as described in [Olefin polymer production processes].

After synthesized by the aforementioned process, the propylene polymers of the invention may be subjected to known post treatment steps such as catalyst deactivation step, residual catalyst removal step and drying step as required.

The primary structure of the inventive propylene polymer is controlled to the specific structure described above. Consequently, the propylene polymer of the invention exhibits high heat resistance and high mechanical properties such as high rigidity and high strength, and is also easily crystallized into a β-phase.

To increase the amount of a β-phase formed in the inventive propylene polymer, a β-phase nucleator may be added to the polymer. Examples of the β-phase nucleators include amide compounds, tetraoxaspiro compounds, quinacridones, nano-scale size iron oxides, alkali metal or alkaline earth metal carboxylate salts such as potassium 1,2-hydroxystearate, magnesium benzoate and magnesium succinate, aromatic sulfonic compounds such as sodium benzenesulfonate and sodium naphthalenesulfonate, di- or triesters of dibasic or tribasic carboxylic acids, phthalocyanine pigments such as phthalocyanine blue, binary compounds composed of a component a that is an organic dibasic acid and a component b that is an oxide, a hydroxide or a salt of a Group IIA metal of the periodic table, and compositions composed of cyclic phosphorus compounds and magnesium compounds.

[Shaped Articles]

The shaped articles of the invention include the aforementioned olefin polymers or propylene polymers. The olefin polymers or the propylene polymers may be shaped into desired articles such as films, sheets, sealants, blow molded articles, injection stretch blow molded articles, injection molded articles and fibers by various shaping methods such as injection molding, extrusion, injection stretch blow molding, blow molding and casting.

The propylene polymers of the invention (propylene polymers obtained by the inventive production processes or the novel propylene polymers) may be shaped into articles containing β-phases and thereafter the β-phase may be transitioned into α-phase by methods such as stretching. Alternatively, the propylene polymers may be directly shaped into articles free from β-phase.

The olefin polymers or the propylene polymers of the invention may contain various additives such as antioxidants, UV absorbers, antistatic agents, nucleators, lubricants, flame retardants, antiblocking agents, colorants, inorganic or organic fillers and various synthetic resins as required.

EXAMPLES

The present invention will be described in further detail based on Examples hereinbelow. However, the scope of the invention is not limited to such Examples.

[Property Measurement Methods]

Ethylene Content in Propylene/Ethylene Copolymers

With a Fourier transform infrared spectrophotometer FT/IR-610 manufactured by JASCO Corporation, a propylene/ethylene copolymer was analyzed to determine the area near 1155 cm$^{-1}$ ascribed to the lateral vibration of the methyl group of propylene, and the absorbance near 4325 cm$^{-1}$ ascribed to the overtone absorption due to the C—H stretching vibration. From the ratio of these parameters, the ethylene content in the copolymer was calculated with reference to a calibration curve. The calibration curve had been prepared using samples standardized by $^{13}$C-NMR.

Intrinsic Viscosity ([η])

With automated kinetic viscometer VMR-053PC and a modified Ubbelohde capillary viscometer manufactured by RIGO CO., LTD., the specific viscosity ηsp at 135° C. in decalin was measured. The intrinsic viscosity ([η]) was calculated using the following equation.

$[\eta]=\eta sp/\{C(1+K\cdot\eta sp)\}$ ($C$: solution concentration [g/dl], $K$: constant)

MFR

The MFR was measured at 230° C. under 2.16 kg load in accordance with ASTM D 1238.

Weight-Average Molecular Weight (Mw) and Number-Average Molecular Weight (Mn)

With Alliance GPC 2000 manufactured by Waters, 500 μl of a 0.1 wt. % sample solution was pumped at a flow rate of 1.0 ml/min to measure the weight-average molecular weight (Mw) and the number-average molecular weight (Mn). Standard polystyrenes manufactured by TOSO CORPORATION were used. The molecular weights of propylene homopolymers and propylene/ethylene copolymers were appropriately converted into molecular weights of propylene homopolymers by a universal calibration method. In the calculation, the Mark-Houwink coefficients were K=2.42×10$^{-4}$ and α=0.707 (see C. M. L. Atkinson, R. Dietz, Makromol. Chem., 177, 213 (1976)).

Separation columns: two TSKgel GMH6-HT columns and two TSKgel GMH6-HTL columns (each 7.5 mm in inner diameter and 300 mm in length)

Column temperature: 140° C.

Mobile phase: o-dichlorobenzene

Detector: differential refractometer (containing 0.025 wt % dibutylhydroxytoluene)

Melting Point (Tm) and Crystallization Temperature (Tc) of Propylene Homopolymers The melting point (Tm) and the crystallization temperature (Tc) of propylene homopolymers were measured with Diamond DSC manufactured by Perkin Elmer Co., Ltd. in the following manner. A sample was melted at 230° C. and was formed into a sheet. Approximately 5 mg of the sheet sample was packed into a sample pan of B014-3021/B700-1014 manufactured by Perkin Elmer Co., Ltd.

In a nitrogen atmosphere, the sample was heated to 230° C., held at the temperature for 10 minutes, and cooled to 30° C. at 10° C./min. The crystallization temperature (Tc) was calculated from the peak top of the crystallization peak observed during this process. Next, the sample was held at 30° C. for 1 minute in a nitrogen atmosphere, and heated to 230° C. at 10° C./min. The melting point (Tm) was calculated from the peak top of the crystal melting peak observed during this process. In the case where a plurality of crystal melting peaks were observed, the peak at the highest temperature was assigned to the melting of an α-phase, and a peak at a lower temperature was assigned to the melting of a β-phase.

Stereoregularity (mmmm and Regioirregularity) of Polypropylenes

The meso pentad fraction (mmmm), and the regioirregularity due to 2,1-insertions and 1,3-insertions were calculated by $^{13}$C-NMR spectroscopy. In the $^{13}$C-NMR spectroscopy, 50 mg of the sample was dissolved in 0.6 ml of a 4/1 mixture solvent including o-dichlorobenzene and deuterated benzene (o-dichlorobenzene/deuterated benzene by volume), and the solution was analyzed on nuclear magnetic resonance apparatus A500 manufactured by JEOL Ltd. under conditions of 120° C., 45° pulse, 5.5 sec repetition time and 16000 scans. The reference chemical shift was 21.59 ppm assigned to the mmmm of the methyl groups. The 2,1-insertion fraction: F(2,1)×100 (mol %), the 1,3-insertion fraction: F(1,3)×100 (mol %), and the meso pentad fraction (mmmm): F(mmmm)×100(%) were calculated using the following equations, respectively. The detection limit was 0.01%.

$$F(2,1) = \frac{[\{I(R1) + I(R2)\} \div 2]}{[I(CH3) + I(R1) + I(R2) + \{I(A1) + I(A3)\} \div 2 + \{I(C1) + I(C3)\} \div 2]}$$

$$F(1,3) = \frac{[\{I(S1) + I(S2)\} \div 4]}{[I(CH3) + \{I(S1) + I(S2)\} \div 4]}$$

$$F(mmmm) = \frac{1(mmmm)}{(1(mmmm) + 1(mmmr) + 1(rmmr) + 1(mmrr) + 1(rmrr) + 1(rmrm) + 1(mmrm) + 1(rrrr) + 1(mrrr) + 1(A1) - [(A3) - \{1(C1) + 1(C2)\} \div 2 + 1(mrrm))}$$

The letter symbols in the above formulae have the following definitions.

I (X) indicates the integral of a methyl peak at 19 to 22 ppm assigned to X. I (CH$_3$) indicates the total area of methyl peaks at 19 to 22 ppm. R1 and R2 represent peaks assigned to 2,1-insertions in structures (R) illustrated below. While the following assignments assume that the polymer is an erythro isomer, assignments may be made in the similar manner in the case of a threo isomer. S1 and S2 represent peaks assigned to 1,3-insertions in structures (S) illustrated below. A1, A3, C1, C2 and C3 represent peaks assigned to polymer terminal structures (A and C) illustrated below.

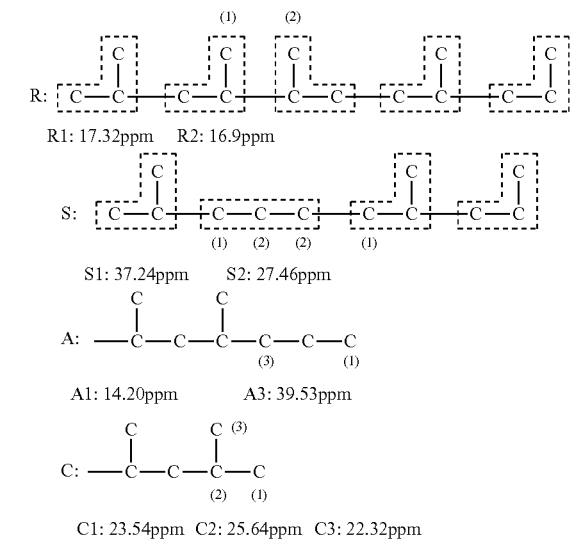

Other peaks were assigned with reference to A. Zambelli, D. E. Dorman, A. I. Richard Brewster and F. A. Bovey, Macromolecules, Vol. 6, No. 6, 925 (1973).

Analysis of Crystal Structures of Propylene Homopolymers

A 2 mg piece of a compression molded sheet of a propylene homopolymer was heated at 230° C. for 10 minutes and was thereafter cooled to 30° C. at a rate of 5° C./min, thereby preparing a sample. The sample was analyzed by wide-angle X-ray diffractometry at room temperature with use of Beamline BL03XU of the Large-scale synchrotron radiation facility Spring-8. The measurement was performed with an X-ray having a wavelength of 1 Å. In the diffraction pattern, the results were converted into 1.54 Å.

The β-phase fraction (Kβ) was calculated using the following equation (see Turner Jones, A.; Aizlewood, J. M.; Beckett, D. R., Makromol. Chem. 75 (1964) 134-158).

$$K_\beta = H_{300}{}^\beta / (H_{110}{}^\alpha + H_{040}{}^\alpha + H_{130}{}^\alpha + H_{300}{}^\beta)$$

Here, $H\alpha_{110}$, $H\alpha_{040}$ and $H\alpha_{130}$ indicate the intensities of peaks assigned to the (110), (040) and (130) reflections of an α-phase, respectively, and $H\beta_{300}$ indicates the intensity of a peak assigned to the (300) reflection of a β-phase.

Measurement of Zirconium Content in Supported Catalysts

The zirconium content in supported catalysts was measured with an ICP emission spectrophotometer (ICPS-8100) manufactured by Shimadzu Corporation. The sample was wet decomposed with sulfuric acid and nitric acid. A prescribed amount of the sample liquid (which had been filtered and diluted as required) was analyzed, and the zirconium content was determined based on a calibration curve prepared with standard samples having known concentrations.

Identification of Structures and Purities of Compounds and Catalysts

The structures and purities of compounds and catalysts obtained in Examples and Comparative Examples were determined by methods such as nuclear magnetic resonance (NMR, GSH-270 manufactured by JEOL Ltd.), field desorption mass spectrometry (FD-MS, SX-102A manufactured by JEOL Ltd.) and gas chromatography mass spectrometry (GC-MS, HP6890/HP5973 manufactured by Hewlett-Packard or GC-17A/GCMS-QP5050A manufactured by Shimadzu Corporation). The steric structures of metallocene compounds were determined by comparing a spectrum obtained by $^1$H-NMR measurement to theoretical spectra calculated with respect to various stereoisomers.

Unless otherwise mentioned, all examples were carried out in a dry nitrogen atmosphere using a dried solvent.

1,1,4,4,7,7,10,10-Octamethyl-2,3,4,7,8,9,10,12-octahydro-1H-dibenzo[b,h]fluorene was synthesized in accordance with Examples described in WO 2001/27124. Hereinbelow, 1,1,4,4,7,7,10,10-octamethyl-2,3,4,7,8,9,10,12-octahydro-1H-dibenzo[b,h]fluorene will be written as "octamethylfluorene".

Synthesis of Transition Metal Compounds

[Example 1A] Synthesis of (1-octamethylfluoren-12'-yl-5-tert-butyl-3-isopropyl-1-methyl-1,2,3,4-tetrahydropentalene)zirconium dichloride (Catalyst A)

(1) 5-Tert-butyl-1-isopropyl-3-methyl-1,2-dihydropentalene: In a nitrogen atmosphere, a 100 ml three-necked flask was loaded with 50 ml of methanol, 2.54 g of tert-butylcyclopentadiene, 5.2 ml of pyrrolidine and 2.1 ml of isobutyl aldehyde in an ice water bath. The mixture was stirred at room temperature for 4 hours and at 40° C. for 1.5 hours. After the addition of 2.1 ml of additional isobutyl aldehyde, the mixture was stirred at room temperature for 18 hours and at 70° C. for 7 hours. 7.0 ml of acetone was added, and reaction was performed at 70° C. for 17 hours. Further, 10 ml of acetone was added, and the mixture was stirred at 70° C. for 6 hours. The reaction solution was poured into 150 ml of 0.5 M hydrochloric acid. The organic layer was separated. The aqueous layer was extracted with 150 ml of hexane. The obtained extract was combined with the previously separated organic layer, and the combined organic layer was washed with a saturated aqueous sodium hydrogen carbonate solution, water and a brine. The liquid was dried with magnesium sulfate, and the solvent was evaporated. The residue was purified by column chromatography to afford the title compound. The amount obtained was 0.96 g, and the yield was 21%.

(2) 1-Octamethylfluoren-12'-yl-5-tert-butyl-3-isopropyl-1-methyl-1,2,3,4-tetrahydropentalene: In a nitrogen atmosphere, a 100 ml three-necked flask was loaded with 1.54 g of octamethylfluorene and 30 ml of tert-butyl methyl ether. In an ice water bath, 2.60 ml of a 1.59 M hexane solution of n-butyllithium was added dropwise over a period of 12 minutes. The mixture was stirred at room temperature for 2 hours and at 40° C. for 2 hours. 15 ml of a tert-butyl methyl ether solution of 0.96 g of 5-tert-butyl-1-isopropyl-3-methyl-1,2-dihydropentalene was added at −12° C. over a period of 30 minutes. The mixture was stirred at room temperature for 21 hours. The resultant reaction solution was added to 100 ml of 0.1 N hydrochloric acid. The organic layer was separated. The aqueous layer was extracted with 80 ml of hexane. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was washed with methanol to afford the title compound. The amount obtained was 1.48 g, and the yield was 62%.

The compound was identified to be the target compound based on the results of the FD-MS measurement. FD-MS: m/Z=602.5 (M$^+$).

$^1$H-NMR showed that the compound was a mixture of isomers.

(3) Catalyst A: In a nitrogen atmosphere, a 30 ml Schlenk flask was loaded with 0.699 g of 1-(octamethylfluorene-12'-yl)-5-tert-butyl-3-isopropyl-1-methyl-1,2,3,4-tetrahydropentalene, 0.140 g of a-methylstyrene, 10 g of hexane, and 1.15 ml of cyclopentyl methyl ether. In an oil bath at 26° C., 1.45 ml of a 1.65 M hexane solution of n-butyllithium was added dropwise over a period of 15 minutes. The mixture was stirred at 70° C. for 4 hours and was cooled in an ice/acetone bath. The liquid was degassed by evacuating the system for 5 minutes, and the pressure was returned to normal pressure with nitrogen. After the addition of 0.293 g of zirconium tetrachloride, reaction was performed for 17.5 hours while gradually returning the temperature to room temperature. The solvent was evaporated, and soluble components were extracted with hexane. The insolubles were removed by filtration, and the insolubles were washed with hexane. The solution obtained was concentrated and was recrystallized in hexane. The solid was filtered and was dried under reduced pressure to afford the target compound. The amount obtained was 0.189 g, and the yield was 21.4%.

The compound was identified to be the target compound based on the results of the $^1$H-NMR and FD-MS measurements.

$^1$H-NMR (270 MHz, CDCl$_3$, with reference to TMS): δ 7.98 (s, 1H), 7.90 (s, 1H), 7.66 (s, 1H), 7.42 (s, 1H), 6.22 (d, 1H), 5.26 (d, 1H), 3.74-3.67 (m, 1H), 3.00-2.91 (m, 1H), 2.62-2.54 (m, 1H), 2.31 (s, 3H), 1.80-1.68 (m, 9H), 1.55 (s, 3H), 1.42 (s, 3H), 1.40 (s, 3H), 1.39 (s, 3H), 1.28 (s, 3H), 1.27 (s, 3H), 1.25 (s, 3H), 1.09 (s, 9H), 1.04 (d, 3H), 1.01 (d, 3H).

FD-MS: m/Z=762.3 (M$^+$)

[Example 2A] Synthesis of (1-octamethylfluoren-12'-yl-5-tert-butyl-3-cyclohexyl-1-methyl-1,2,3,4-tetrahydropentalene)zirconium dichloride (Catalyst B)

(1) 5-Tert-butyl-1-cyclohexyl-3-methyl-1,2-dihydropentalene: In a nitrogen atmosphere, a 100 ml three-necked flask was loaded with 30 ml of cyclopentyl methyl ether and 3.0 g of tert-butylcyclopentadiene. In an ice water bath, 15.5 ml of a 1.65 M hexane solution of n-butyllithium was added dropwise to the solution over a period of 40 minutes. The mixture was stirred at room temperature for 1 hour. In an ice water bath, 2.95 g of cyclohexane carboxyaldehyde was added dropwise over a period of 15 minutes, and the mixture was stirred at room temperature for 23.5 hours. Further, in an ice water bath, 1.57 g of cyclohexane carboxyaldehyde was added, and the mixture was stirred at room temperature for 2.5 hours. 5.2 ml of pyrrolidine and 4.0 ml of acetone were added, and the mixture was stirred at 80° C. for 14.5 hours. 50 ml of 2 N hydrochloric acid was poured into the reaction solution. The organic layer was separated. The aqueous layer was extracted with 100 ml of hexane. The obtained extract was combined with the previously separated organic layer, and the combined organic layer was washed with a saturated aqueous sodium hydrogen carbonate solution, water and a brine. The liquid was dried with magnesium sulfate, and the solvent was evaporated. Acetone and methanol were added to the residue. The mixture was cooled to −12° C. and was stirred for 1 hour. The solid precipitated was filtered and was dried under reduced pressure to afford the title compound. The amount obtained was 1.4 g, and the yield was 22%.

The compound was identified to be the target compound based on the results of the $^1$H-NMR measurement.

$^1$H-NMR (270 MHz, CDCl$_3$, with reference to TMS): δ 5.98 (s, 1H), 5.86 (s, 1H), 3.01 (dd, 2H), 2.77-2.63 (m, 2H), 2.13 (s, 3H), 1.91 (m, 1H), 1.80-1.60 (m, 4H), 1.35-0.96 (m+s, 15H).

(2) 1-Octamethylfluoren-12'-yl-5-tert-butyl-3-cyclohexyl-1-methyl-1,2,3,4-tetrahydropentalene: In a nitrogen atmosphere, a 100 ml three-necked flask was loaded with 0.881 g of octamethylfluorene, 22.2 g of cyclohexane and 0.55 ml of cyclopentyl methyl ether. In an ice water bath, 1.45 ml of a 1.65 M hexane solution of n-butyllithium was added dropwise over a period of 10 minutes. The mixture was stirred at room temperature for 1 hour and at 50° C. for 2.5 hours. After the addition of 18.5 g of cyclohexane, 19.90 g of a cyclohexane solution of 0.64 g of 5-tert-butyl-1-cyclohexyl-3-methyl-1,2-dihydropentalene was added over a period of 10 minutes. The mixture was stirred at room temperature for 18 hours and at 80° C. for 7 hours. Thereafter, 60 ml of 0.11 N hydrochloric acid was added to the reaction solution. The organic layer was separated. The aqueous layer was extracted with 100 ml of hexane. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was purified by column chromatography and was washed with hexane to afford the title compound. The amount obtained was 0.70 g, and the yield was 48%.

The compound was identified to be the target compound based on the results of the FD-MS measurement. FD-MS: m/Z=642.5 (M$^+$).

$^1$H-NMR showed that the compound was a mixture of isomers.

(3) Catalyst (B): In a nitrogen atmosphere, a 30 ml Schlenk flask was loaded with 0.684 g of 1-octamethylfluorene-12'-yl-5-tert-butyl-3-cyclohexyl-1-methyl-1,2,3,4-tetrahydropentalene, 0.254 g of a-methylstyrene, 16 g of cyclohexane, and 1.25 ml of cyclopentyl methyl ether. In an oil bath at 28° C., 1.30 ml of a 1.65 M hexane solution of n-butyllithium was added dropwise over a period of 10 minutes. The mixture was stirred at 70° C. for 5 hours and was cooled in an ice/acetone bath. The liquid was degassed by evacuating the system for 5 minutes, and the pressure was returned to normal pressure with nitrogen. After the addition of 0.269 g of zirconium tetrachloride, the acetone bath was removed and reaction was performed at room temperature for 15.5 hours. The solvent was evaporated, and soluble components were extracted with hexane. The insolubles were removed by filtration, and the insolubles were washed with hexane. The solution obtained was concentrated and was recrystallized in hexane. The solid was filtered and was dried under reduced pressure to afford the target compound. The amount obtained was 0.071 g, and the yield was 8.3%.

The compound was identified to be the target compound based on the results of the $^1$H-NMR and FD-MS measurements.

$^1$H-NMR (270 MHz, CDCl$_3$, with reference to TMS): δ 7.97 (s, 1H), 7.90 (s, 1H), 7.63 (s, 1H), 7.43 (s, 1H), 6.23 (d, 1H), 5.26 (d, 1H), 3.709 (1H, dd), 2.914 (m, 1H), 2.604 (1H, dd), 2.30 (s, 1H), 1.78-1.1.13 (m, 32H), 1.09 (s, 9H).

FD-MS: m/Z=802.3 (M$^+$).

[Example 3A] Synthesis of (1-octamethylfluoren-12'-yl-5-tert-butyl-3-(cyclohex-3-enyl)-1-methyl-1,2,3,4-tetrahydropentalene zirconium dichloride (Catalyst C)

(1) 5-Tert-butyl-1-(cyclohex-3-enyl)-3-methyl-1,2-dihydropentalene: In a nitrogen atmosphere, a 100 ml three-necked flask was loaded with 30 ml of cyclopentyl methyl ether and 2.5 g of tert-butylcyclopentadiene. In an ice water bath, 13.0 ml of a 1.65 M hexane solution of n-butyllithium was added dropwise to the solution over a period of 45 minutes. The mixture was stirred at room temperature for 2 hours. In an ice water bath, 2.6 g of 3-cyclohexenyl carboxyaldehyde was added dropwise over a period of 10 minutes, and the mixture was stirred at room temperature for 20 hours. Further, 0.47 g of 3-cyclohexenyl carboxyaldehyde was added, and the mixture was stirred at room temperature for 5 hours. Furthermore, 0.94 g of 3-cyclohexenyl carboxyaldehyde was added, and the mixture was stirred at room temperature for 2 hours. 5.2 ml of pyrrolidine and 4.0 ml of acetone were added, and the mixture was stirred at 80° C. for 17 hours. 44 ml of 2 N hydrochloric acid and 50 ml of water were poured into the reaction solution. The organic layer was separated. The aqueous layer was extracted with 150 ml of hexane. The obtained extract was combined with the previously separated organic layer, and the combined organic layer was washed with a saturated aqueous sodium hydrogen carbonate solution, water and a brine. The liquid was dried with magnesium sulfate, and the solvent was evaporated. The residue was purified by column chromatography to afford the title compound. The amount obtained was 1.4 g, and the yield was 26%.

The compound was identified to be the target compound based on the results of the $^1$H-NMR measurement.

$^1$H-NMR (270 MHz, CDCl$_3$, with reference to TMS): δ 6.00 (d, 1H), 5.88 (m, 1H), 5.74-5.67 (m, 2H), 3.14-2.66 (m, 4H), 2.77-2.63 (m, 2H), 2.14 (s, 3H), 2.08-1.60 (m, 4H), 1.22 (s, 9H).

(2) 1-Octamethylfluoren-12'-yl-5-tert-butyl-3-(cyclohex-3-enyl)-1-methyl-1,2,3,4-tetrahydropentalene: In a nitrogen atmosphere, a 100 ml three-necked flask was loaded with 1.61 g of octamethylfluorene, 30 ml of cyclohexane and 1.0 ml of cyclopentyl methyl ether. In an ice water bath, 2.65 ml of a 1.65 M hexane solution of n-butyllithium was added dropwise over a period of 10 minutes. The mixture was stirred at 50° C. for 4 hours. 15 ml of a cyclohexane solution of 1.4 g of 5-tert-butyl-1-(cyclohex-3-enyl)-3-methyl-1,2-dihydropentalene was added over a period of 10 minutes. The mixture was stirred at 50° C. for 15.5 hours and at 80° C. for 5.5 hours. Thereafter, 50 ml of 0.1 N hydrochloric acid was added to the reaction solution. The organic layer was separated. The aqueous layer was extracted with 100 ml of hexane. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was washed with hexane to afford the title compound. The amount obtained was 1.69 g, and the yield was 64%.

The compound was identified to be the target compound based on the results of the FD-MS measurement. FD-MS: m/Z=640.5 (M$^+$).

$^1$H-NMR showed that the compound was a mixture of isomers.

(3) Catalyst (C): In a nitrogen atmosphere, a 30 ml Schlenk flask was loaded with 0.800 g of 1-octamethylfluorene-12'-yl-5-tert-butyl-3-(cyclohex-3-enyl)-1-methyl-1,2,3,4-tetrahydropentalene, 0.301 g of α-methylstyrene, 16 g of cyclohexane, and 1.45 ml of cyclopentyl methyl ether. In an oil bath at 28° C., 1.5 ml of a 1.65 M hexane solution of n-butyllithium was added dropwise over a period of 10 minutes. The mixture was stirred at 70° C. for 5 hours and was cooled in an ice/acetone bath. The liquid was degassed by evacuating the system for 5 minutes, and the pressure was returned to normal pressure with nitrogen. After the addition of 0.269 g of zirconium tetrachloride, the acetone bath was removed and reaction was performed at room temperature for 17 hours. The solvent was evaporated, and soluble components were extracted with hexane. The insolubles were removed by filtration, and the insolubles were washed with hexane. The solution obtained was concentrated and was recrystallized in hexane. The solid was filtered and was dried under reduced pressure to afford the target compound. The amount obtained was 0.123 g, and the yield was 12.3%.

The compound was identified to be the target compound based on the results of the $^1$H-NMR and FD-MS measurements.

$^1$H-NMR (270 MHz, CDCl$_3$, with reference to TMS): δ 7.98 (s, 1H), 7.90 (s, 1H), 7.64 (s, 1H), 7.43 (s, 1H), 6.25-6.21 (m, 1H), 5.70 (m, 1H), 5.27 (m, 1H), 3.77-3.74 (m, 1H), 3.07-2.99 (m, 1H), 2.69-2.60 (m, 1H), 2.30 (s, 3H), 2.1-1.25 (m, 42H), 1.09 (s, 9H).

FD-MS: m/Z=800.3 (M$^+$).

[Example 4A] Synthesis of (1-octamethylfluoren-12'-yl-3,5-di-tert-butyl-1-methyl-1,2,3,4-tetrahydropentalene)zirconium dichloride (Catalyst D)

(1) 1,5-Di-tert-butyl-3-methyl-1,2-dihydropentalene: In a nitrogen atmosphere, a 100 ml three-necked flask was loaded with 50 ml of cyclopentyl methyl ether and 2.5 g of tert-butylcyclopentadiene. In an ice water bath, 13.2 ml of a 1.57 M hexane solution of n-butyllithium was added dropwise to the solution over a period of 40 minutes. The mixture was stirred at room temperature for 2 hours. In an ice water bath, 2.02 g of pivalaldehyde was added dropwise over a period of 3 minutes, and the mixture was stirred at room temperature for 3 hours. 8.3 ml of pyrrolidine and 6.0 ml of acetone were added, and the mixture was stirred at 80° C. for 16 hours. The reaction solution was poured into 100 ml of 1.1 N hydrochloric acid. The organic layer was separated. The aqueous layer was extracted with 100 ml of hexane. The obtained extract was combined with the previously separated organic layer, and the combined organic layer was washed with a saturated aqueous sodium hydrogen carbonate solution, water and a brine. The liquid was dried with magnesium sulfate, and the solvent was evaporated. The resultant solid was added to a mixed solvent including ethanol and methanol, and the mixture was stirred. The solid precipitated was filtered and was dried under reduced pressure to afford the title compound. The amount obtained was 2.09 g, and the yield was 44%.

The compound was identified to be the target compound based on the results of the $^1$H-NMR measurement.

$^1$H-NMR (270 MHz, CDCl$_3$, with reference to TMS): δ 5.99 (s, 1H), 5.85 (s, 1H), 2.95-2.66 (m, 3H), 2.13 (s, 3H), 1.22 (s, 9H), 0.91 (s, 9H).

(2) 1-Octamethylfluoren-12'-yl-3,5-di-tert-butyl-1-methyl-1,2,3,4-tetrahydropentalene: In a nitrogen atmosphere, a 100 ml three-necked flask was loaded with 2.27 g of octamethylfluorene, 50 ml of cyclohexane and 1.4 ml of cyclopentyl methyl ether. In an ice water bath, 3.90 ml of a 1.57 M hexane solution of n-butyllithium was added dropwise over a period of 10 minutes. The mixture was stirred at 50° C. for 2 hours. 1.50 g of 1,5-di-tert-butyl-3-methyl-1,2-dihydropentalene was added, and the mixture was stirred at 80° C. for 17 hours. Thereafter, the reaction solution was added to 50 ml of 0.2 N hydrochloric acid. The organic layer was separated. The aqueous layer was extracted with 200 ml of hexane. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was purified by column chromatography and was washed with hexane to afford the title compound as a light yellow powder. The amount obtained was 1.91 g, and the yield was 53%.

The compound was identified to be the target compound based on the results of the FD-MS measurement. FD-MS: m/Z=616.5 (M$^+$).

$^1$H-NMR showed that the compound was a mixture of isomers.

(3) Catalyst (D): In a nitrogen atmosphere, a 30 ml Schlenk flask was loaded with 1.00 g of 1-octamethylfluoren-12'-yl-3,5-di-tert-butyl-1-methyl-1,2, 3,4-tetrahydropentalene, 0.386 g of a-methylstyrene, 16 g of cyclohexane, and 1.90 ml of cyclopentyl methyl ether. In an oil bath at 26° C., 2.10 ml of a 1.57 M hexane solution of n-butyllithium was added dropwise over a period of 10 minutes. The mixture was stirred at 70° C. for 5 hours and was cooled in an ice/acetone bath. The liquid was degassed by evacuating the system for 5 minutes, and the pressure was returned to normal pressure with nitrogen. After the addition of 0.3978 g of zirconium tetrachloride, the acetone bath was removed and reaction was performed at room temperature for 16 hours. The solvent was evaporated, and soluble components were extracted with hexane. The insolubles were removed by filtration, and the insolubles were washed with hexane. The solution obtained was concentrated and was recrystallized in hexane. The solid was filtered and was dried under reduced pressure to afford the target compound. The amount obtained was 0.423 g, and the yield was 34%.

The compound was identified to be the target compound based on the results of the $^1$H-NMR and FD-MS measurements.

$^1$H-NMR (270 MHz, CDCl$_3$, with reference to TMS): δ 7.97 (1H, s), 7.90 (1H, s), 7.67 (1H, s), 7.43 (1H, s), 6.22 (1H, d), 5.27 (1H, d), 3.58 (1H, dd), 3.08 (1H, dd), 2.63 (1H, dd), 2.31 (3H, s), 1.784-1.661 (11H, m), 1.552 (3H, s), 1.445-1.352 (3H, m), 1.30-1.28 (12H, m), 1.24 (3H, s), 1.09 (9H, s), 0.98 (9H, s).

FD-MS: m/Z=776.3 (M$^+$).

[Example 5A] Synthesis of (8-octamethylfluoren-12'-yl-(2-tert-butyl-8-methyl-3,3b,4, 5,6,7,7a,8-octahydrocyclopenta[a]indene))zirconium dichloride (Catalyst E)

(1) 2-Tert-butyl-8-methyl-3,3b,4,5,6,7,7a,8-octahydrocyclopenta[a]indene: In a nitrogen atmosphere, a 100 ml three-necked flask was loaded with 50 ml of THF and 2.5 g of tert-butylcyclopentadiene. In an ice/acetone bath, 13.0 ml of a 1.65 M hexane solution of n-butyllithium was added dropwise to the solution over a period of 40 minutes. The mixture was stirred at room temperature for 17 hours. In an ice water bath, 2.19 g of magnesium chloride was added, and the mixture was stirred at room temperature for 6.5 hours.

0.432 g of copper iodide was added. In an ice/acetone bath, 7.08 g (38.3 wt %) of a hexane solution of 1-acetylcyclohexene was added dropwise over a period of 10 minutes, and the mixture was stirred at room temperature for 19 hours. 1.3 ml of acetic acid and 5.2 ml of pyrrolidine were added, and the mixture was stirred at room temperature for 17 hours. The reaction solution was poured into 120 ml of 0.5 N hydrochloric acid. The organic layer was separated. The aqueous layer was extracted with 200 ml of hexane. The obtained extract was combined with the previously separated organic layer, and the combined organic layer was washed with water, a saturated aqueous sodium hydrogen carbonate solution and a brine. The liquid was dried with magnesium sulfate, and the solvent was evaporated. The obtained product was recrystallized in methanol to afford the title compound. The amount obtained was 0.445 g, and the yield was 9.5%.

The compound was identified to be the target compound based on the results of the $^1$H-NMR and GC-MS measurements.

$^1$H-NMR (Toluene-$d_8$): δ 6.01 (1H, s), 5.98 (1H, s), 2.88-2.73 (2H, m), 1.84 (3H, s), 1.80-1.03 (17H, m).

GC-MS: m/Z=228 ($M^+$).

(2) 8-Octamethylfluoren-12'-yl-(2-tert-butyl-8-methyl-3, 3b,4,5,6,7,7a,8-octahydrocyclopenta[a]indene): In a nitrogen atmosphere, a 30 ml Schlenk flask was loaded with 0.655 g of octamethylfluorene and 20 ml of tert-butyl methyl ether. In an ice water bath, 1.10 ml of a 1.65 M hexane solution of n-butyllithium was added dropwise over a period of 15 minutes. The mixture was stirred for 22 hours while gradually returning the temperature to room temperature. There was added 0.453 g of 2-tert-butyl-8-methyl-3,3b,4,5, 6,7,7a,8-octahydrocyclopenta[a]indene. The mixture was stirred at room temperature for 19 hours and at 50° C. for 6.5 hours. Thereafter, the reaction solution was added to 100 ml of 0.1 N hydrochloric acid. The organic layer was separated. The aqueous layer was extracted with 100 ml of hexane. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was purified by column chromatography and was washed with acetone to afford the title compound. The amount obtained was 0.50 g, and the yield was 48%.

The compound was identified to be the target compound based on the results of the FD-MS measurement. FD-MS: m/Z=614.5 ($M^+$).

$^1$H-NMR showed that the compound was a mixture of isomers.

(3) Catalyst (E): In a nitrogen atmosphere, a 30 ml Schlenk flask was loaded with 0.503 g of 8-octamethylfluoren-12'-yl-(2-tert-butyl-8-methyl-3,3b,4,5,6,7,7a,8-octahydrocyclopenta[a]indene, 0.193 g of a-methylstyrene, 13.6 g of hexane, and 0.95 ml of cyclopentyl methyl ether. In an oil bath at 25° C., 1.00 ml of a 1.65 M hexane solution of n-butyllithium was added dropwise over a period of 10 minutes. The mixture was stirred at 70° C. for 4 hours and was cooled in an ice/acetone bath. The liquid was degassed by evacuating the system for 5 minutes, and the pressure was returned to normal pressure with nitrogen. After the addition of 0.193 g of zirconium tetrachloride, the acetone bath was removed and reaction was performed at room temperature for 17 hours. The solvent was evaporated, and soluble components were extracted with hexane. The insolubles were removed by filtration, and the insolubles were washed with hexane. The solution obtained was concentrated. The supernatant was removed by decantation, and the solid was washed with hexane and was dried under reduced pressure to afford the target compound. The amount obtained was 0.057 g, and the yield was 9.0%.

The compound was identified to be the target compound based on the results of the $^1$H-NMR and FD-MS measurements.

$^1$H-NMR (270 MHz, $CDCl_3$, with reference to TMS): δ 7.99 (1H, s), 7.86 (1H, s), 7.61 (1H, s), 7.32 (1H, s), 6.16 (1H, s), 5.33 (1H, s), 3.58-3.49 (2H, m), 2.34-2.29 (1H, m), 2.20 (3H, s), 1.93-1.19 (39H, m), 1.10 (9H, s).

FD-MS: m/Z=774.3 ($M^+$).

[Comparative Example 1A] Synthesis of [3-(octamethylfluoren-12'-yl)(1, 1,3-trimethyl-5-tert-butyl-1,2, 3,3a-tetrahydropentalene)]zirconium dichloride (Catalyst a)

(1) 5-Tert-butyl-1,1,3-trimethyl-1,2-dihydropentalene: In a nitrogen atmosphere, a 200 ml three-necked flask was loaded with 4.83 g of tert-butylcyclopentadiene, 9.0 ml of 4-methylpent-3-en-2-one, 40 ml of methanol and 16.5 ml of pyrrolidine. The mixture was stirred for 43 hours under reflux. The reaction solution was poured into 250 ml of 1 N hydrochloric acid. The organic layer was separated. The aqueous layer was extracted with 200 ml of hexane. The obtained extract was combined with the previously separated organic layer, and the combined organic layer was washed with water and a brine. The liquid was dried with magnesium sulfate, and the solvent was evaporated. The residue was purified by column chromatography to afford the title compound. The purity was determined to be 86.8% by gas chromatography. The amount obtained was 5.46 g, and the yield was 59.4%.

$^1$H-NMR (270 MHz, $CDCl_3$, with reference to TMS): δ 5.87 (s, 1H), 5.79 (s, 1H), 2.94 (d, 1H), 2.10 (t, 3H), 1.27 (s, 1H), 1.21 (s, 9H).

GC-MS: m/Z=202 ($M^+$).

(2) 3-(Octamethylfluoren-12'-yl)(1,1,3-trimethyl-5-tert-butyl-1,2,3,3a-tetrahydropentalene): In a nitrogen atmosphere, a 100 ml three-necked flask was loaded with 1.58 g of octamethylfluorene and 30 ml of diethyl ether. In an ice/acetone bath, 2.7 ml of a 1.56 M hexane solution of n-butyllithium was added dropwise over a period of 15 minutes. The mixture was stirred for 25 hours while gradually increasing the temperature to room temperature. 10 ml of a diethyl ether solution of 0.95 g of 5-tert-butyl-1,1,3-trimethyl-1,2-dihydropentalene was added over a period of 5 minutes. The mixture was stirred for 56 hours under reflux. The reaction solution was poured into 100 ml of 1 N hydrochloric acid. The organic layer was separated. The aqueous layer was extracted with 75 ml of hexane two times. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was purified by column chromatography and was washed with pentane and ethanol to afford the title compound. The amount obtained was 2.02 g, and the yield was 84%.

The compound was identified to be the target compound based on the results of the $^1$H-NMR and FD-MS measurements.

¹H-NMR (270 MHz, CDCl₃, with reference to TMS): δ 7.58 (s, 1H), 7.55+7.54 (s, 1H), 7.50+7.49 (s, 1H), 6.89+6.46 (s, 1H), 6.32+5.93 (s, 1H), 3.87+3.83 (s, 1H), 3.11 (q, 1H), 2.68 (d, 1H), 1.71 (s, 3H), 1.67-1.61 (m, 8H), 1.38-1.28 (m, 27H), 1.18-0.95 (m, 11H), 0.27+0.21 (s, 3H).

FD-MS: m/Z=589 (M⁺).

(3) Catalyst (a): In a nitrogen atmosphere, a 30 ml Schlenk flask was loaded with 0.884 g of 3-(octamethylfluoren-12'-yl)(1,1,3-trimethyl-5-tert-butyl-1,2,3,3a-tetrahydropentalene) and 20 ml of hexane. In an ice/acetone bath, 2.05 ml of a 1.56 M hexane solution of n-butyllithium was added, and the mixture was stirred for 15 minutes. 0.351 g (3.12 mmol) of tert-butoxypotassium was added. The mixture was stirred for 5 hours while gradually returning the temperature to room temperature. Thereafter, the mixture was filtered to give a red purple powder. The red purple powder was washed with approximately 10 ml of hexane. The red purple powder and 30 ml of diethyl ether were added to a 30 ml Schlenk flask. After cooling in an ice/acetone bath, 0.452 g (1.94 mmol) of zirconium tetrachloride was added. The mixture was stirred for 39 hours while gradually returning the temperature to room temperature. The solvent was evaporated, and soluble components were extracted with dichloromethane. The solvent was evaporated. Hexane was added to the solid obtained, and soluble components were extracted. The hexane solution was concentrated, and a solid was precipitated, removed by decantation, and dried under reduced pressure to afford the target compound. The amount obtained was 0.248 g, and the yield was 22.2%.

The compound was identified to be the target compound based on the results of the ¹H-NMR and FD-MS measurements.

¹H-NMR (270 MHz, CDCl₃, with reference to TMS): δ 7.99 (s, 1H), 7.98 (s, 1H), 7.78 (s, 1H), 7.54 (s, 1H), 6.01 (d, 1H), 5.25 (d, 1H), 3.94 (d, 1H), 2.62 (d, 1H), 2.31 (s, 3H), 1.79-1.61 (m, 8H), 1.57 (s, 3H), 1.43 (s, 3H), 1.41 (s, 3H), 1.39 (s, 9H), 1.35 (s, 3H), 1.32 (s, 3H), 1.28 (s, 3H), 1.24 (s, 3H), 1.09 (s, 9H).

FD-MS: m/Z=748 (M⁺).

[Comparative Example 2A] Synthesis of [12-(2-tert-butyl-8-cyclohexyl-1,3b,4,5,6,7,7a,8-octahydrocyclopenta[a]inden-3b-yl)-octamethylfluorene]zirconium dichloride (Catalyst b)

(1) 2-Tert-butyl-8-cyclohexyl-4,5,6,7,7a,8-hexahydrocyclopenta[a]indene: In a nitrogen atmosphere, a 100 ml three-necked flask was loaded with 50 ml of THF and 2.5 g of tert-butylcyclopentadiene. In an ice/acetone bath, 12.6 ml of a 1.67 M hexane solution of n-butyllithium was added dropwise to the solution over a period of 35 minutes. The mixture was stirred at room temperature for 16.5 hours. In an ice/acetone bath, 2.50 g of cyclohexyl carboxyaldehyde was added dropwise over a period of 15 minutes. The mixture was stirred at room temperature for 5 hours. 8.3 ml of pyrrolidine and 6.3 ml of cyclohexanone were added, and the mixture was stirred for 18 hours under reflux. 3.5 g of Molecular Sieve 4A was added, and reaction was performed for another 118 hours. The reaction solution was poured into 120 ml of 1.1 N hydrochloric acid. The organic layer was separated. The aqueous layer was extracted with 200 ml of hexane. The obtained extract was combined with the previously separated organic layer, and the combined organic layer was washed with a saturated aqueous sodium hydrogen carbonate solution, water and a brine. The liquid was dried with magnesium sulfate, and the solvent was evaporated. Methanol was added, and the mixture was stirred. The resultant solid precipitate was filtered and was dried under reduced pressure to afford the title compound. The amount obtained was 1.66 g, and the yield was 27%.

The compound was identified to be the target compound based on the results of the ¹H-NMR measurement.

¹H-NMR (270 MHz, CDCl₃, with reference to TMS): δ 5.96 (1H, s), 5.85 (1H, s), 2.89 (1H, m), 2.70 (1H, dd), 2.37-2.09 (3H, m), 2.001-1.585 (7H, m), 1.521-0.935 (18H, m).

(2) 12-(2-Tert-butyl-8-cyclohexyl-1,3b,4,5,6,7,7a,8-octahydrocyclopenta[a]inden-3b-yl)-octamethylfluorene: In a nitrogen atmosphere, a 100 ml three-necked flask was loaded with 1.24 g of octamethylfluorene, 50 ml of cyclohexane and 0.75 ml of cyclopentyl methyl ether. In an ice water bath, 2.00 ml of a 1.67 M hexane solution of n-butyllithium was added dropwise over a period of 10 minutes. The mixture was stirred at 50° C. for 5 hours. 1.01 g of 2-tert-butyl-8-cyclohexyl-4,5,6,7,7a,8-hexahydrocyclopenta[a]indene was added, and the mixture was stirred at 80° C. for 20 hours. The reaction solution was added to 100 ml of 0.1 N hydrochloric acid. The organic layer was separated. The aqueous layer was extracted with 100 ml of hexane. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was purified by column chromatography and was recrystallized in a mixed solvent including hexane and ethanol to afford the title compound. The amount obtained was 0.84 g, and the yield was 38%.

The compound was identified to be the target compound based on the results of the FD-MS measurement. FD-MS: m/Z=682.6 (M⁺).

¹H-NMR showed that the compound was a mixture of isomers.

(3) Catalyst b: In a nitrogen atmosphere, a 30 ml Schlenk flask was loaded with 0.689 g of 12-(2-tert-butyl-8-cyclohexyl-1,3b,4,5,6,7,7a,8-octahydrocyclopenta[a]inden-3b-yl)-octamethylfluorene, 0.239 g of a-methylstyrene, 13.5 g of hexane, and 1.17 ml of cyclopentyl methyl ether. In an oil bath at 26° C., 1.23 ml of a 1.67 M hexane solution of n-butyllithium was added dropwise over a period of 10 minutes. The mixture was stirred at 70° C. for 4.5 hours and was cooled in an ice/acetone bath. The liquid was degassed by evacuating the system for 5 minutes, and the pressure was returned to normal pressure with nitrogen. After the addition of 0.239 g of zirconium tetrachloride, the acetone bath was removed and reaction was performed at room temperature for 16 hours. The solvent was evaporated, and soluble components were extracted with hexane. The insolubles were removed by filtration, and the insolubles were washed with hexane. The solution obtained was concentrated and was recrystallized in hexane. The solid was filtered and was dried under reduced pressure to afford the target compound. The amount obtained was 0.178 g, and the yield was 21%.

The compound was identified to be the target compound based on the results of the ¹H-NMR and FD-MS measurements.

¹H-NMR (270 MHz, CDCl₃, with reference to TMS): δ 8.00 (1H, s), 8.00 (1H, s), 7.76 (1H, s), 7.57 (1H, s), 6.14 (1H, d), 5.33 (1H, d), 3.74-3.61 (1H, m), 2.99-2.86 (1H, m), 2.72-2.52 (2H, m), 2.30-0.72 (58H, m).

FD-MS: m/Z=842.4 (M⁺).

[Comparative Example 3A] Synthesis of phenylmethylene(4-tert-butyl-2-isopropylcyclopentadienyl)(octamethylfluoren-12'-yl)zirconium dichloride (Catalyst c)

(1) 3-Tert-butyl-1-isopropyl-6-phenylfulvene: In a nitrogen atmosphere, a 30 ml Schlenk flask was loaded with 0.72 g of sodium ethoxide, 10 ml of ethanol, an ethanol solution of 1.7 g of tert-butyl-isopropylcyclopentadiene, and 1.2 g of benzaldehyde. The mixture was stirred at room temperature for 22 hours. The reaction solution was poured into a saturated aqueous ammonium chloride solution. The organic layer was separated. The aqueous layer was extracted with 140 ml of hexane. The obtained extract was combined with the previously separated organic layer, and the combined organic layer was washed with water and a brine. The liquid was dried with magnesium sulfate, and the solvent was evaporated. The product was purified by column chromatography to afford the title compound. The amount obtained was 2.1 g, and the yield was 79%.

The compound was identified to be the target compound based on the results of the $^1$H-NMR measurement.

$^1$H-NMR (270 MHz, CDCl$_3$, with reference to TMS): δ 7.57-7.29 (m, 5H), 7.09 (s, 1H), 6.23 (t, 1H), 6.13 (d, 1H), 2.95 (m, 1H), 1.25 (d, 6H), 1.19 (s, 9H).

(2) Phenylmethylene(4-tert-butyl-2-isopropylcyclopentadienyl)octamethylfluorene: In a nitrogen atmosphere, a 100 ml Kjeldahl flask was loaded with 2.85 g of octamethylfluorene and 30 ml of tert-butyl methyl ether. In an ice water bath, 4.6 ml of a 1.66 M hexane solution of n-butyllithium was added dropwise over a period of 20 minutes. The mixture was stirred for 21 hours while gradually increasing the temperature to room temperature. A tert-butyl methyl ether solution of 2.1 g of 3-tert-butyl-1-isopropyl-6-phenylfulvene was added over a period of 10 minutes, and the mixture was stirred at room temperature for 22 hours. The reaction solution was poured into 100 ml of 1 N hydrochloric acid. The organic layer was separated. The aqueous layer was extracted with 75 ml of hexane two times. The obtained extract was combined with the previously separated organic layer, and the combined organic layer was washed one time with a saturated aqueous sodium hydrogen carbonate solution, two times with water, and one time with a brine. The liquid was dried with magnesium sulfate, and the solvent was evaporated. The resultant solid was washed with hexane to afford the title compound. The amount obtained was 2.1 g, and the yield was 44%.

The compound was identified to be the target compound based on the results of the FD-MS measurement.

FD-MS: m/Z=638.6 (M$^+$).

(3) Catalyst c: In a nitrogen atmosphere, a 30 ml Schlenk flask was loaded with 0.81 g of phenylmethylene(4-tert-butyl-2-isopropylcyclopentadienyl)octamethylfluorene, 0.16 g (1.4 mmol) of a-methylstyrene, 13 g of hexane, and 1.5 ml of cyclopentyl methyl ether. In an oil bath at 27° C., 1.6 ml of a 1.59 M hexane solution of n-butyllithium was added dropwise over a period of 15 minutes. The mixture was stirred at 70° C. for 3.5 hours and was cooled in an ice/acetone bath. The liquid was degassed by evacuating the system for 5 minutes, and the pressure was returned to normal pressure with nitrogen. After the addition of 0.29 g of zirconium tetrachloride, reaction was performed for 2 hours. The acetone bath was then removed, and reaction was performed at room temperature for 16 hours. The solvent was evaporated, and soluble components were extracted with hexane. The insolubles were removed by filtration, and the insolubles were washed with hexane. The solution obtained was concentrated and was recrystallized in hexane. The solid was filtered and was dried under reduced pressure to afford the target compound. The amount obtained was 0.06 g, and the yield was 6%.

The compound was identified to be the target compound based on the results of the $^1$H-NMR and FD-MS measurements.

$^1$H-NMR (270 MHz, CDCl$_3$, with reference to TMS): δ 8.00 (s, 1H), 7.98 (s, 1H), 7.82-7.79 (2H), 7.54-7.43 (4H), 6.5 (s, 1H), 6.47 (s, 1H), 6.23 (d, 1H), 5.45 (d, 1H), 3.18 (m, 1H), 1.79-1.61 (m, 8H), 1.50 (s, 3H), 1.47 (s, 3H), 1.44 (s, 3H), 1.38 (s, 9H), 1.35 (d, 3H), 1.32 (s, 3H), 1.26 (s, 3H), 1.19 (d, 3H), 1.07 (s, 9H), 0.96 (s, 3H), 0.93 (s, 3H).

FD-MS: m/Z=798.3 (M$^+$).

Preparation of Silica-Supported Methylaluminoxane

A stirring rod was attached to a 100 ml three-necked flask that had been thoroughly purged with nitrogen. To the flask, 5.00 g of a silica gel (H-121 manufactured by AGC-Si Tech. Co., Ltd.) was added which had been dried at 180° C. in a nitrogen stream for 6 hours. Further, 64 ml of dehydrated toluene, and 19.5 ml of a toluene solution of methylaluminoxane (manufactured by Albemarle Corporation, 19.3 wt %) were added at room temperature. The mixture was stirred at 95° C. for 4 hours. The resultant slurry was filtered through a filter, and the powder on the filter was washed with 25 ml of dehydrated toluene three times and with 25 ml of dehydrated hexane three times. The washed powder was dried under reduced pressure for 2 hours to give a silica-supported methylaluminoxane. The Al concentration in the silica-supported methylaluminoxane was 18.0 wt %. A silica-supported methylaluminoxane having an Al concentration of 17.4 wt % was obtained in the similar manner.

Preparation of Supported Catalysts

Example 1B

A stirring rod was attached to a 100 ml three-necked flask that had been thoroughly purged with nitrogen. To the flask, 1.0018 g of the silica-supported methylaluminoxane (Al=18.0 wt %) was added. Further, 30 ml of dehydrated toluene was added at room temperature. While performing stirring, there was added 4 ml of a toluene solution which contained 23.1 mg of the catalyst A synthesized in Example 1A as a transition metal compound. The mixture was stirred for 1 hour. The resultant slurry was filtered through a filter, and the powder on the filter was washed with 10 ml of dehydrated toluene one time and with 10 ml of dehydrated hexane three times. The washed powder was dried under reduced pressure for 2 hours to give 0.9815 g of a powdery supported catalyst. The powder was mixed together with a mineral oil to form a 10.0 wt % slurry. The zirconium concentration in the supported catalyst was 0.248 wt %.

Examples 2B to 5B and Comparative Examples 1B to 3B

The procedures in Example 1B were repeated, except that the type and the amount of the silica-supported methylaluminoxane, the amount of dehydrated toluene added, and the type and the amount of the transition metal compound in Example 1B were changed as described in Table 1. The amounts of the powders obtained, and the zirconium concentrations in the supported catalysts are also described in Table 1.

catalyst prepared in Comparative Example 1B, 1.0 ml of a hexane solution of triisobutylaluminum (Al=1.0 M) and 5.0 ml of dehydrated hexane. The whole amount of the resultant

TABLE 1

| | Supported catalysts | | | | |
|---|---|---|---|---|---|
| | Ex. 1B | Ex. 2B | Ex. 3B | Ex. 4B | Ex. 5B |
| Amount of silica-supported methylaluminoxane (Al = 18.0 wt %) added | 1.0018 g | 1.0001 g | 0.9996 g | 1.0016 g | 1.0006 g |
| Amount of dehydrated toluene added | 30 ml | 30 ml | 30 ml | 30 ml | 30 ml |
| Toluene solution of transition metal compound — Transition metal compound | Metallocene compound catalyst A of Ex. 1A | Metallocene compound catalyst B of Ex. 2A | Metallocene compound catalyst C of Ex. 3A | Metallocene compound catalyst D of Ex. 4A | Metallocene compound catalyst E of Ex. 5A |
| Amount of transition metal compound | 23.1 mg | 22.7 mg | 23.1 mg | 22.4 mg | 22.4 mg |
| Amount of toluene solution | 4 ml | 4 ml | 4 ml | 4 ml | 4 ml |
| Amount of powder obtained | 0.9815 g | 0.9773 g | 0.9686 g | 0.9820 g | 0.9363 g |
| Zirconium concentration in supported catalyst | 0.248 wt % | 0.233 wt % | 0.226 wt % | 0.228 wt % | 0.246 wt % |

| | Comp. Ex. 1B | Comp. Ex. 2B | Comp. Ex. 3B |
|---|---|---|---|
| Amount of silica-supported methylaluminoxane (Al = 17.4 wt %) added | 0.980 g | 1.000 g | 1.001 g |
| Amount of dehydrated toluene added | 10 ml | 10 ml | 10 ml |
| Toluene solution of transition metal compound — Transition metal compound | Metallocene compound catalyst a of Comp. Ex. 1A | Metallocene compound catalyst b of Comp. Ex. 2A | Metallocene compound catalyst c of Comp. Ex. 3A |
| Amount of transition metal compound | 19.7 mg | 22.5 mg | 22.2 mg |
| Amount of toluene solution | 20 ml | 20 ml | 20 ml |
| Amount of powder obtained | 0.8820 g | 0.9450 g | 0.9401 g |
| Zirconium concentration in supported catalyst | 0.240 wt % | 0.210 wt % | 0.220 wt % |

Propylene Homopolymerization

Example 1c

A magnetic stirrer was placed in a 50 ml branched flask that had been thoroughly purged with nitrogen. The flask was then loaded with 0.509 g of the slurry of the supported catalyst prepared in Example 1B, 1.5 ml of a hexane solution of triisobutylaluminum (Al=1.0 M) and 5.0 ml of dehydrated hexane. The whole amount of the resultant mixture was fed into a 3,400 ml-volume SUS autoclave that had been thoroughly purged with nitrogen. Thereafter, 750 g of liquid propylene and 0.24 NL of hydrogen were supplied, and polymerization was performed at 70° C. for 40 minutes. The polymerization was terminated by cooling the autoclave and purging out propylene. The polymer obtained was dried under reduced pressure at 80° C. for 10 hours. The results are described in Table 2 and Table 3.

Examples 2c to 11c

The procedures in Example 1c were repeated, except that the type of the supported catalyst, the amount of the slurry used, the amount of hydrogen supplied and the polymerization time in Example 1c were changed as described in Table 2. The results are described in Table 2 and Table 3. The results of the analysis of the crystal structure of the polymer obtained in Example 7c are shown in FIG. 1.

Comparative Example 1c

A magnetic stirrer was placed in a 50 ml branched flask that had been thoroughly purged with nitrogen. The flask was then loaded with 0.344 g of the slurry of the supported catalyst prepared in Comparative Example 1B, 1.0 ml of a hexane solution of triisobutylaluminum (Al=1.0 M) and 5.0 ml of dehydrated hexane. The whole amount of the resultant mixture was fed into a 2,000 ml-volume SUS autoclave that had been thoroughly purged with nitrogen. Thereafter, 500 g of liquid propylene and 0.30 NL of hydrogen were supplied, and polymerization was performed at 70° C. for 40 minutes. The polymerization was terminated by cooling the autoclave and purging out propylene. The polymer obtained was dried under reduced pressure at 80° C. for 10 hours. The results are described in Table 2 and Table 3.

Comparative Example 2c

The procedures in Comparative Example 1c were repeated, except that the type of the supported catalyst, the amount of the slurry used and the amount of hydrogen supplied in Comparative Example 1c were changed as described in Table 2. The results are described in Table 2 and Table 3.

Comparative Examples 3c to 5c

The procedures in Example 1c were repeated, except that the type of the supported catalyst, the amount of the slurry used and the amount of hydrogen supplied in Example 1c were changed as described in Table 2. The results are described in Table 2 and Table 3.

Comparative Example 6c

Propylene was polymerized by the method described in Example 20b of WO 2006/025540. The transition metal compound used in Comparative Example 6c will be written as "catalyst d". The zirconium concentration in the supported catalyst was 0.232 wt %. The results obtained are described in Table 2 and Table 3.

Comparative Example 7c

Rac-dimethylsilylene bis(2-methyl-4-phenylindenyl)zirconium dichloride was synthesized in accordance with JP-A-H07-196734. This compound will be written as "catalyst e".

In a 500 ml-volume gas-flow glass polymerization reactor that had been thoroughly purged with nitrogen, 250 ml of toluene was added and was cooled to 0° C. Propylene and hydrogen were supplied at 100 L/h and 2.5 L/h, respectively, and the inside of the system was thoroughly saturated with these gases. Next, 0.25 mmol of triisobutylaluminum was added. Further, there was added a toluene solution of a mixture including 0.61 mol of the catalyst e and 0.3 mmol (in terms of Al atoms) of methylaluminoxane manufactured by Albemarle Corporation. Polymerization was performed for 10 minutes while maintaining the system at 0° C. The polymerization was terminated by adding a small amount of isobutyl alcohol. The polymerization suspension was added to 1 L of methanol containing a small amount of hydrochloric acid, and the mixture was sufficiently stirred and filtered. The polymer was washed with a large amount of methanol and was dried at 80° C. for 10 hours. The polymer obtained weighed 9.40 g, and the catalytic activity was 92.5 kg-polymer/mmol-Zr·h. The results are described in Table 2 and Table 3.

Comparative Example 8c

Propylene Polymerization Catalyzed by Magnesium Chloride-Supported Solid Titanium Catalyst (1) [1] Preparation of Solid Titanium Catalyst Component
[1-i] Preparation of Solid Component A 2 L-volume high-speed stirrer (manufactured by PRIMIX Corporation) was thoroughly purged with nitrogen and was loaded with 700 ml of purified kerosine, 10 g of commercial magnesium chloride, 24.2 g of ethanol and 3 g of EMASOL 320 (sorbitan distearate, manufactured by Kao Atlas). The temperature in the system was increased while performing stirring, and the materials were stirred at 120° C. and 800 rpm for 30 minutes. While performing stirring at high speed, the liquid was transferred to a 2 L glass flask (equipped with a stirrer) which contained 1 L of purified kerosine cooled at −10° C. through a Teflon (registered trademark) tube having an inner diameter of 5 mm. The resultant solid was filtered and was sufficiently washed with purified n-hexane. Thus, a solid-state product was obtained in which ethanol was coordinated to magnesium chloride. The solid-state product (825 mmol in terms of magnesium atoms) was suspended in 548 ml of decane, and the whole amount of the suspension was added to 2.2 L of titanium tetrachloride at −20° C. while performing stirring. The suspension was heated to 110° C. in 5.5 hours. When the temperature reached 110° C., 33.0 ml of diisobutyl phthalate was added. The mixture was stirred at 110° C. for 1.5 hours. After the completion of the 1.5-hour reaction, the solid was collected by hot filtration and was washed with decane at 100° C. and hexane at room temperature until no titanium was detected in the filtrate.

[1-ii] Preparation of Solid Titanium Catalyst Component (Contact Treatment with Polar Compound)

A 6 L glass reactor that had been thoroughly purged with nitrogen was loaded with 4.1 L of 2,4-dichlorotoluene, 123.6 ml (1124.8 mmol) of titanium tetrachloride and 15.1 ml (56.4 mmol) of diisobutyl phthalate. Next, 133.7 g of the solid component obtained in [1-i] was added. The temperature in the reactor was increased to 130° C., and stirring was performed at the temperature for 1 hour. After the 1-hour contact treatment, the solid was collected by hot filtration and was resuspended in 4.1 L of 2,4-dichlorotoluene. Further, 123.6 ml (1124.8 mmol) of titanium tetrachloride and 15.1 ml (56.4 mmol) of diisobutyl phthalate were added. The temperature was then raised and, when the temperature reached 130° C., the system was held at the temperature for 1 hour while performing stirring.

After the completion of the reaction, solid liquid separation was performed again by hot filtration. The solid obtained was washed with decane at 100° C. and hexane at room temperature until the content of 2,4-dichlorotoluene in the catalyst was decreased to 1 wt % or below. As a result, a solid titanium catalyst component was obtained which contained 1.3 wt % titanium, 20 wt % magnesium and 14.7 wt % diisobutyl phthalate. The electron donor/titanium ratio (by weight) was 11.3.

(2) Preparation of Prepolymerized Catalyst

In a 1 L autoclave that had been purged with nitrogen, 180 ml of n-heptane was added and was cooled to 0° C. Thereafter, the autoclave was loaded with 18 mmol of triethylaluminum (TEA), 2.7 mmol of diethylaminotriethoxysilane, 9.95 g of propylene and 0.9 mmol in terms of titanium atoms of the solid titanium catalyst component obtained in [1] Preparation of solid titanium catalyst component. The autoclave was then closed, and reaction was performed at 20° C. for 1 hour while performing stirring. After the completion of the polymerization, the reaction mixture was collected in a nitrogen atmosphere, and the supernatant liquid was removed by decantation. The solid was washed with heptane three times. The resultant prepolymerized catalyst was resuspended in heptane. The amount of prepolymerization was 3.0 g per 1 g of the solid titanium catalyst component.

(3) Main Polymerization

A 5 L-volume autoclave was purged with hydrogen and was loaded with 1500 g of propylene. After the temperature was increased to 60° C., 50 ml of n-heptane, 0.41 mmol of triethylaluminum, 0.081 mmol of diethylaminotriethoxysilane and 10 mg in terms of the solid catalyst component of the prepolymerized catalyst obtained in (2) Preparation of prepolymerized catalyst were mixed together, and the mixture was injected into the autoclave with hydrogen. The temperature of the autoclave was controlled to 70° C. The pressure during the polymerization was adjusted constant at 3.6 MPaG with hydrogen. The polymerization time was 1 hour. After the completion of the polymerization, the slurry containing the solid was separated by filtration into a white powder and a liquid phase. The polymer obtained as the white powder was dried. The results are described in Table 2 and Table 3.

Comparative Example 9c

F143H manufactured by Prime Polymer Co., Ltd. is a polypropylene synthesized using a magnesium chloride-supported solid titanium catalyst. F143H was analyzed in the same manner as in Examples. The results are described in Table 2 and Table 3. The results of the analysis of the crystal structure of the polymer are shown in FIG. 2.

Propylene/Ethylene Copolymerization

Example 1d

Into a 3400 ml-volume SUS autoclave that had been thoroughly purged with nitrogen, 450 g of liquid propylene was added and was heated to 55° C. while being sufficiently stirred. The autoclave inside pressure was then increased to 3.0 MPaG by supplying ethylene gas. Subsequently, a 30 ml-volume catalyst insertion pot that had been thoroughly purged with nitrogen fitted to the autoclave was loaded with a mixed solution of 4 ml of dehydrated hexane and 0.5 ml of a hexane solution of triisobutylaluminum (Al=1.0 M), and the mixed solution was injected into the autoclave with nitrogen. Subsequently, the catalyst insertion pot was loaded with a mixture of 359 mg of the slurry of the supported catalyst prepared in Example 5B and 0.5 ml of a hexane solution of triisobutylaluminum (Al=1.0 M). The mixture was injected into the autoclave with nitrogen, and thereby polymerization was initiated. After the polymerization was performed for 4.5 minutes, a small amount of methanol was added to terminate the polymerization. The polymer was deashed by being added to a large excess of methanol containing hydrochloric acid. The polymer was then filtered and was dried at 80° C. under reduced pressure for 10 hours. The results are described in Table 4.

Example 2d

The procedures in Example 1d were repeated, except that the autoclave inside pressure was changed from 3.0 MPaG to 3.5 MPaG and the amount of the slurry of the supported catalyst was changed from 359 mg to 355 mg. The results are described in Table 4.

Example 3d

The procedures in Example 1d were repeated, except that the autoclave inside pressure was changed from 3.0 MPaG to 4.0 MPaG and the amount of the slurry of the supported catalyst was changed from 359 mg to 310 mg. The results are described in Table 4.

Comparative Example 1d

Into a 2000 ml-volume SUS autoclave that had been thoroughly purged with nitrogen, 300 g of liquid propylene was added and was heated to 55° C. while being sufficiently stirred. The autoclave inside pressure was then increased to 30 kg/cm²G by supplying ethylene gas. Subsequently, a 30 ml-volume catalyst insertion pot that had been thoroughly purged with nitrogen fitted to the autoclave was loaded with a mixed solution of 4 ml of dehydrated hexane and 1 ml of a hexane solution of triisobutylaluminum (Al=1.0 M), and the mixed solution was injected into the autoclave with nitrogen. Subsequently, the catalyst insertion pot was loaded with a mixture of 339 mg of the slurry of the supported catalyst prepared in Comparative Example 1B and 1.0 ml of a hexane solution of triisobutylaluminum (Al=1.0 M). The mixture was injected into the autoclave with nitrogen, and thereby polymerization was initiated. After the polymerization was performed for 8 minutes, a small amount of methanol was added to terminate the polymerization. The polymer was deashed by being added to a large excess of methanol containing hydrochloric acid. The polymer was then filtered and was dried at 80° C. under reduced pressure for 10 hours. The results are described in Table 4.

Comparative Example 2d

The procedures in Comparative Example 1d were repeated, except that the autoclave inside pressure was changed from 30 kg/cm²G to 35 kg/cm²G, the amount of the slurry of the supported catalyst was changed from 339 mg to 340 mg, and the polymerization time was changed from 8 minutes to 4.5 minutes. The results are described in Table 4.

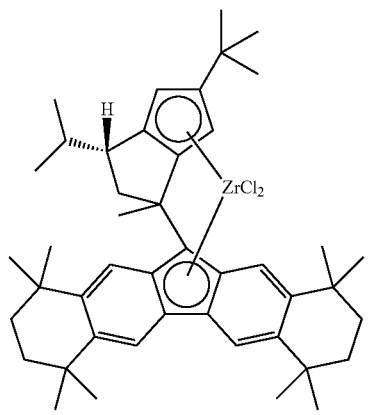

Catalyst A

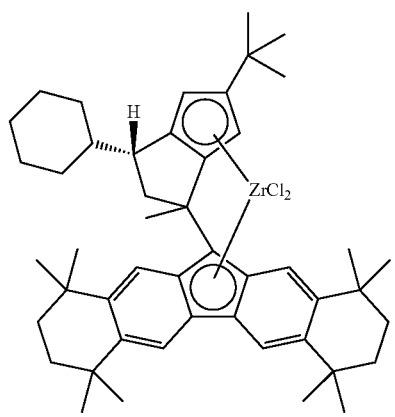

Catalyst B

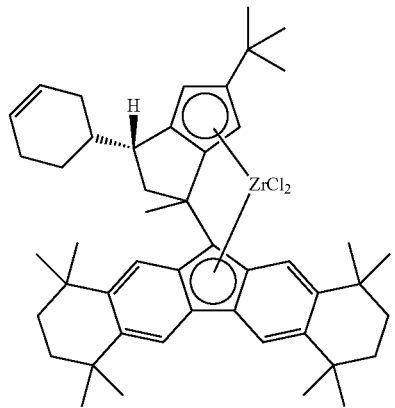

Catalyst C

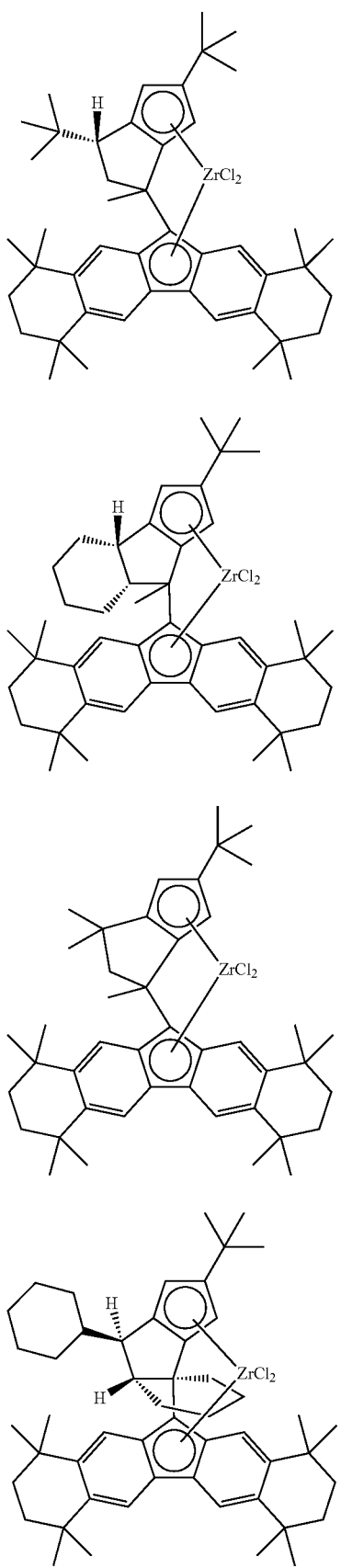
Catalyst D
Catalyst E
Catalyst a
Catalyst b
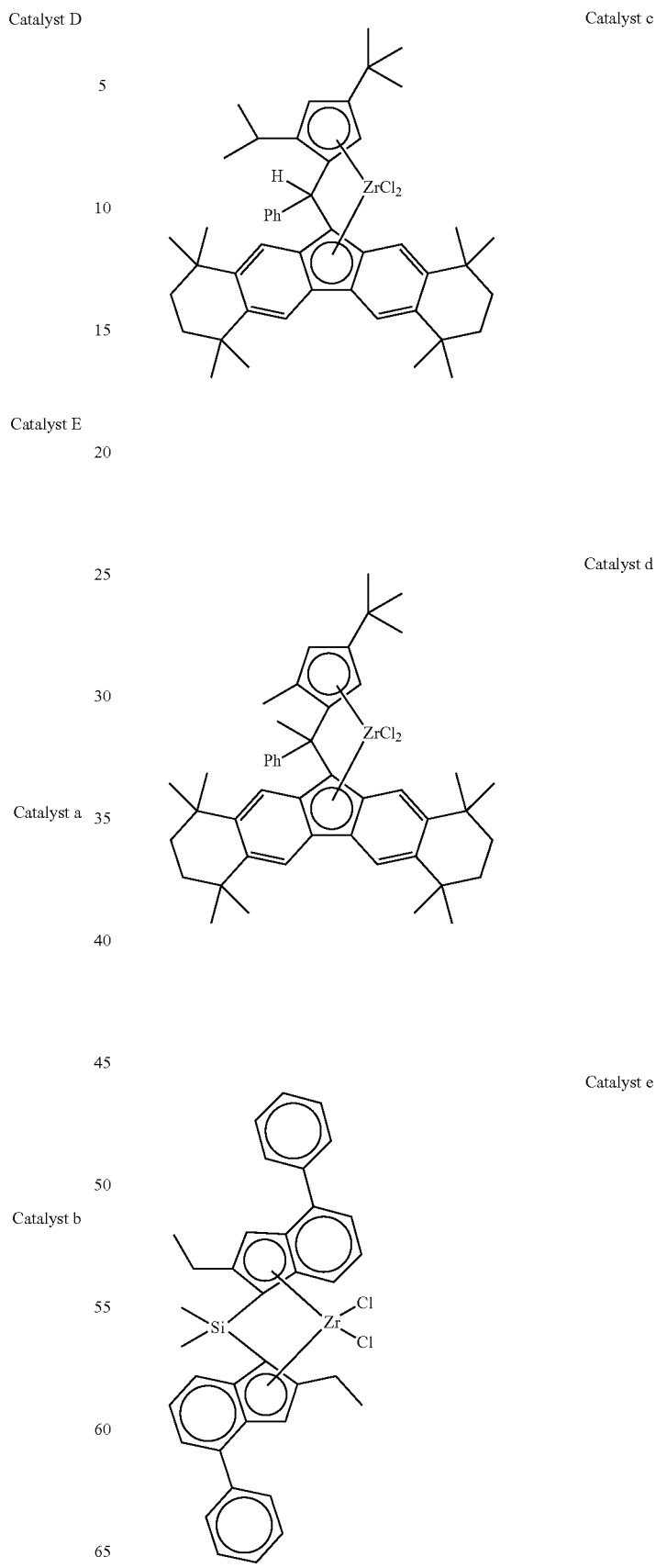
Catalyst c
Catalyst d
Catalyst e

TABLE 2

Propylene homopolymerization

| | | Slurry of supported catalyst | | | | | | |
|---|---|---|---|---|---|---|---|---|
| | Type of catalyst | Amount of slurry g | Amount of supported catalyst mg | Amount of hydrogen supplied NL | | Polymeri-zation time min | Yield amount g | Catalytic activity | |
| | | | | | mol % | | | kg/mmol-Zr/h | g/g-cat/h |
| Ex. 1c | Catalyst A | 0.509 | 50.9 | 0.24 | 0.07 | 40 | 174.3 | 189 | $5.14 \times 10^3$ |
| Ex. 2c | Catalyst A | 0.412 | 41.2 | 0.48 | 0.14 | 40 | 262.4 | 351 | $9.54 \times 10^3$ |
| Ex. 3c | Catalyst A | 0.190 | 19.0 | 1.20 | 0.37 | 60 | 356.8 | 692 | $1.88 \times 10^4$ |
| Ex. 4c | Catalyst B | 0.407 | 40.7 | 0.48 | 0.14 | 40 | 256.7 | 370 | $9.45 \times 10^3$ |
| Ex. 5c | Catalyst B | 0.263 | 26.3 | 1.28 | 0.37 | 40 | 373.8 | 834 | $2.13 \times 10^4$ |
| Ex. 6c | Catalyst C | 0.397 | 39.7 | 0.48 | 0.14 | 40 | 240.4 | 367 | $9.09 \times 10^3$ |
| Ex. 7c | Catalyst C | 0.248 | 24.8 | 1.28 | 0.37 | 40 | 373.7 | 911 | $2.26 \times 10^4$ |
| Ex. 8c | Catalyst D | 0.409 | 40.9 | 0.48 | 0.14 | 40 | 210.0 | 309 | $7.71 \times 10^3$ |
| Ex. 9c | Catalyst D | 0.248 | 24.8 | 1.28 | 0.37 | 40 | 270.9 | 656 | $1.64 \times 10^4$ |
| Ex. 10c | Catalyst E | 0.516 | 51.5 | 0.48 | 0.14 | 40 | 366.4 | 395 | $1.07 \times 10^4$ |
| Ex. 11c | Catalyst E | 0.258 | 25.8 | 1.28 | 0.37 | 40 | 400.7 | 863 | $2.33 \times 10^4$ |
| Comp. Ex. 1c | Catalyst a | 0.344 | 34.4 | 0.30 | 0.13 | 40 | 243.7 | 404 | $1.06 \times 10^4$ |
| Comp. Ex. 2c | Catalyst a | 0.198 | 19.8 | 0.60 | 0.26 | 40 | 247.5 | 713 | $1.87 \times 10^4$ |
| Comp. Ex. 3c | Catalyst c | 0.520 | 52.0 | 0.40 | 0.11 | 40 | 124.3 | 149 | $3.59 \times 10^3$ |
| Comp. Ex. 4c | Catalyst b | 0.409 | 40.9 | 0.48 | 0.14 | 40 | 129.9 | 207 | $4.76 \times 10^3$ |
| Comp. Ex. 5c | Catalyst b | 0.260 | 26.0 | 1.28 | 0.37 | 40 | 178.9 | 450 | $1.03 \times 10^4$ |
| Comp. Ex. 6c | Catalyst d | 0.340 | 34.0 | 0.60 | 0.26 | 40 | 159.5 | 276 | $7.04 \times 10^3$ |
| Comp. Ex. 7c | Catalyst e | — | — | — | — | — | — | — | — |
| Comp. Ex. 8c | Solid Ti | — | — | — | — | — | — | — | — |
| Comp. Ex. 9c | Solid Ti | — | — | — | — | — | — | — | — |

| | α phase | | β phase | | | | | |
|---|---|---|---|---|---|---|---|---|
| | Tm °C. | Tc °C. | Tm °C. | Mw ×10⁴ | Mn ×10⁴ | Mw/Mn | [η] dl/g | MFR$^{2.16}$ g/10 min |
| Ex. 1c | 162.7 | 114.3 | 148.0 | 33.3 | 14.3 | 2.34 | 2.35 | 2.2 |
| Ex. 2c | 163.0 | 114.3 | 148.2 | 22.5 | 9.00 | 2.49 | 1.82 | 8.4 |
| Ex. 3c | 161.1 | 117.2 | 147.4 | 9.95 | 4.19 | 2.38 | 1.01 | 145 |
| Ex. 4c | 163.4 | 114.8 | 148.7 | 26.1 | 11.0 | 2.37 | 1.96 | 5.5 |
| Ex. 5c | 162.1 | 116.3 | 147.7 | 12.4 | 5.70 | 2.19 | 1.19 | 67 |
| Ex. 6c | 163.6 | 118.7 | 149.4 | 25.7 | 11.2 | 2.29 | 1.97 | 5.5 |
| Ex. 7c | 162.2 | 116.8 | 148.0 | 11.5 | 5.20 | 2.19 | 1.13 | 84 |
| Ex. 8c | 162.7 | 118.3 | 148.2 | 26.5 | 10.9 | 2.44 | 1.91 | 6.3 |
| Ex. 9c | 162.1 | 116.7 | 148.0 | 13.1 | 5.90 | 2.21 | 1.15 | 77 |
| Ex. 10c | 162.3 | 114.0 | 147.4 | 28.0 | 12.2 | 2.30 | 2.13 | 3.8 |
| Ex. 11c | 162.0 | 116.4 | 147.6 | 13.8 | 6.20 | 2.22 | 1.25 | 55 |
| Comp. Ex. 1c | 157.5 | 117.2 | Nil | 14.7 | 6.30 | 2.35 | 1.37 | 38 |
| Comp. Ex. 2c | 157.3 | 118.2 | Nil | 7.49 | 3.59 | 2.09 | 0.82 | 400 |
| Comp. Ex. 3c | 147.6 | 111.5 | Nil | 4.03 | 1.81 | 2.23 | 0.51 | — |
| Comp. Ex. 4c | 156.8 | 115.8 | 144.1 | 8.20 | 3.83 | 2.14 | 0.87 | 330 |
| Comp. Ex. 5c | 154.5 | 113.1 | 142.8 | 3.26 | 1.53 | 2.12 | 0.42 | — |
| Comp. Ex. 6c | 160.3 | 119.0 | Nil | 10.6 | 4.50 | 2.36 | 1.03 | 150 |
| Comp. Ex. 7c | 161.1 | 115.0 | Nil | 57.9 | 24.9 | 2.33 | 3.30 | — |
| Comp. Ex. 8c | 162.4 | 118.7 | Nil | — | — | — | — | 319 |
| Comp. Ex. 9c | 165.6 | 113.7 | Nil | — | — | — | — | 4.0 |

TABLE 3

Propylene homopolymerization

| | | α phase | | β phase | | 2,1-insertion | 1,3-insertion | 2,1-insertion fraction + | β phase |
|---|---|---|---|---|---|---|---|---|---|
| | Type of catalyst | Tm °C. | Tc °C. | Tm °C. | mmm.n % | fraction % | fraction % | 1,3-insertion fraction % | fraction $K_β$ % |
| Ex. 2c | Catalyst A | 163.0 | 114.3 | 148.2 | 98.5 | 0.04 | Blow detection limit | 0.04 | — |
| Ex. 3c | Catalyst A | 161.1 | 117.2 | 147.4 | 98.3 | 0.02 | Blow detection limit | 0.02 | — |
| Ex. 5c | Catalyst B | 162.1 | 116.3 | 147.7 | 99.0 | 0.02 | Blow detection limit | 0.02 | — |
| Ex. 7c | Catalyst C | 162.2 | 116.8 | 148.0 | 99.0 | 0.02 | Blow detection limit | 0.02 | 0.32 |
| Ex. 9c | Catalyst D | 162.1 | 116.7 | 148.0 | 98.7 | 0.01 | Blow detection limit | 0.01 | — |
| Ex. 10c | Catalyst E | 162.3 | 114.0 | 147.4 | 98.7 | 0.03 | 0.02 | 0.05 | — |
| Ex. 11c | Catalyst E | 162.0 | 116.4 | 147.6 | 98.8 | 0.02 | Blow detection limit | 0.02 | — |
| Comp. Ex. 2c | Catalyst a | 157.3 | 118.2 | Nil | 95.6 | Blow detection limit | Blow detection limit | 0.00 | — |
| Comp. Ex. 6c | Catalyst d | 160.3 | 119.0 | Nil | 97.2 | Blow detection limit | Blow detection limit | 0.00 | — |
| Comp. Ex. 7c | Catalyst e | 161.1 | 115.0 | Nil | 98.5 | 0.10 | Blow detection limit | 0.10 | — |

TABLE 3-continued

| | | α phase | | β phase | | 2,1-insertion | 1,3-insertion | 2,1-insertion fraction + | β phase |
|---|---|---|---|---|---|---|---|---|---|
| | Type of catalyst | Tm ° C. | Tc ° C. | Tm ° C. | mmmm % | fraction % | fraction % | 1,3-insertion fraction % | fraction $K_\beta$ % |
| Comp. Ex. 8c | Solid Ti | 162.4 | 118.7 | Nil | 98.0 | Blow detection limit | Blow detection limit | 0.00 | — |
| Comp. Ex. 9c | Solid Ti | 165.6 | 113.7 | Nil | 98.0 | Blow detection limit | Blow detection limit | 0.00 | 0.01 |

Examples which involved the transition metal compounds of the invention produced propylene homopolymers having a mmmm fraction and a total of the 2,1-insertion fraction and the 1,3-insertion fraction in the aforementioned specific ranges. These results are probably ascribed to the fact that the transition metal compounds of the invention had a hydrogen atom at the α-position relative to the cyclopentadiene ring, and the hydrogen atom was present on the same side as the central metal. Probably because of this configuration, the polymers showed a melting point assigned to a β-phase.

In contrast, Comparative Examples which involved solid titanium catalysts produced propylene homopolymers in which the total of the 2,1-insertion fraction and the 1,3-insertion fraction was below the detection limit. Probably because of this, the polymers did not show a melting point assigned to a β-phase.

Comparative Example which involved the catalyst a produced a propylene homopolymer in which the total of the 2,1-insertion fraction and the 1,3-insertion fraction was below the detection limit. A main cause of this result is probably the fact that in the catalyst a, both substituents at the α-position relative to the cyclopentadiene ring were methyl groups instead of hydrogen atoms. Probably because of this configuration, the polymer did not show a melting point assigned to a β-phase.

Comparative Examples which involved the catalyst b produced propylene homopolymers which showed a melting point assigned to a β-phase. However, these polymers had a melting point assigned to an α-phase that was lower than those of the propylene homopolymers obtained in Examples. Consequently, these polymers were poor in heat resistance and rigidity, and also failed to satisfy the aforementioned specific ranges of mmmm and the total of the 2,1-insertion fraction and the 1,3-insertion fraction. Further, their molecular weights were lower than those of the propylene homopolymers obtained under the same polymerization conditions. In spite of such low molecular weights, the catalytic activity was poor. These results are probably ascribed to the fact that the catalyst b had a cyclohexane ring that was present at the α-position relative to the cyclopentadiene ring on the same side as the central metal.

TABLE 4

Propylene/ethylene copolymerization

| | | Slurry of supported catalyst | | | | | |
|---|---|---|---|---|---|---|---|
| | Type of catalyst | Amount of slurry mg | Amount of supported catalyst mg | Polymerization time min | Yield amount g | Catalytic activity | |
| | | | | | | kg/mmol-Zr/h | g/g-cat/h |
| Ex. 1d | Catalyst E | 359 | 35.9 | 4.5 | 14.8 | 203 | 5,480 |
| Ex. 2d | Catalyst E | 355 | 35.5 | 3.5 | 13.2 | 236 | 6,360 |
| Ex. 3d | Catalyst E | 310 | 31.0 | 4.0 | 15.8 | 283 | 7,650 |
| Comp. Ex. 1d | Catalyst a | 339 | 33.9 | 8.0 | 15.6 | 132 | 3,460 |
| Comp. Ex. 2d | Catalyst a | 340 | 34.0 | 4.5 | 15.3 | 229 | 6,010 |

| | Ethylene content mol % | Mw ×10$^4$ | Mw/Mn | [η] dl/g |
|---|---|---|---|---|
| Ex. 1d | 23 | 50.8 | 2.42 | 3.53 |
| Ex. 2d | 34 | 44.2 | 2.25 | 3.30 |
| Ex. 3d | 44 | 41.3 | 2.62 | 3.40 |
| Comp. Ex. 1d | 25 | 43.4 | 2.27 | 3.12 |
| Comp. Ex. 2d | 37 | 39.4 | 2.55 | 3.14 |

Examples 1d to 3d compare favorably to Comparative Examples 1d and 2d in terms of weight-average molecular weight and catalytic activity when the polymers having substantially equal ethylene contents are compared (for example, Example 1d/Comparative Example 1d, and Example 2d/Comparative Example 2d).

INDUSTRIAL APPLICABILITY

The use of the olefin polymerization catalysts including the transition metal compounds of the invention makes it possible to produce useful olefin polymers in an economically efficient manner. Thus, the transition metal compounds of the invention are highly valuable in industry.

The invention claimed is:
1. A propylene polymer having a meso pentad fraction of 97.0% to 99.5% and a total fraction of 2,1-insertions and

1,3-insertions of propylene monomers of 0.01 mol % to 0.06 mol % relative to all propylene-derived structural units as measured by $^{13}$C-NMR, wherein the propylene polymer shows one or more melting peaks assigned to α-phases in the range of 160° C. or more, and also shows one or more melting peaks assigned to β-phases in the range of 140° C. to less than 160° C.

2. A shaped article comprising the propylene polymer described in claim 1.

* * * * *